United States Patent
Jung et al.

(10) Patent No.: US 11,802,123 B2
(45) Date of Patent: *Oct. 31, 2023

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Jung Ha Lee, Daejeon (KR); Dong Hoon Lee, Daejeon (KR); Tae Yoon Park, Daejeon (KR); Boon Jae Jang, Daejeon (KR); Seong Mi Cho, Daejeon (KR); Dong Uk Heo, Daejeon (KR)

(73) Assignee: LG CHEM, LTD., Seoul (KR)

( * ) Notice: Subject to any disclaimer, the term of this patent is extended or adjusted under 35 U.S.C. 154(b) by 16 days.

This patent is subject to a terminal disclaimer.

(21) Appl. No.: 17/523,264

(22) Filed: Nov. 10, 2021

(65) Prior Publication Data

US 2022/0064153 A1 Mar. 3, 2022

Related U.S. Application Data

(63) Continuation of application No. 16/079,962, filed as application No. PCT/KR2017/010057 on Sep. 13, 2017, now Pat. No. 11,208,402.

(30) Foreign Application Priority Data

Nov. 7, 2016 (KR) .................. 10-2016-0147519
Sep. 11, 2017 (KR) .................. 10-2017-0116136

(51) Int. Cl.
*C07D 405/14* (2006.01)
*C07D 405/04* (2006.01)
(Continued)

(52) U.S. Cl.
CPC ......... *C07D 405/14* (2013.01); *C07D 405/04* (2013.01); *C07D 405/10* (2013.01);
(Continued)

(58) Field of Classification Search
CPC ............. H01L 51/0067; H01L 51/5012; H01L 51/5056; H01L 51/5072; H01L 51/0071; H01L 2251/5384; H01L 51/0073; H01L 51/5016; H01L 51/0072; H01L 51/5076; H01L 51/0052; H01L 51/0074; C07D 405/04; C07D 405/10; C07D 411/14; C07D 409/14; C07D 405/14; C09K 11/06
See application file for complete search history.

(56) References Cited

U.S. PATENT DOCUMENTS

| | | | |
|---|---|---|---|
| 9,334,260 B2 | 5/2016 | Parham et al. | |
| 9,406,892 B2 | 8/2016 | Zeng et al. | |
| 9,944,629 B2 | 4/2018 | Hattori et al. | |
| 2011/0006670 A1 | 1/2011 | Katakura et al. | |

(Continued)

FOREIGN PATENT DOCUMENTS

| | | | |
|---|---|---|---|
| JP | 2014-096595 A | 5/2014 | |
| JP | 2016-128432 A | 7/2016 | |

(Continued)

*Primary Examiner* — Gregory D Clark
(74) *Attorney, Agent, or Firm* — Bryan Cave Leighton Paisner LLP

(57) ABSTRACT

The present invention relates to a novel heterocyclic compound and an organic light emitting device comprising the same.

6 Claims, 1 Drawing Sheet

(51) Int. Cl.
*C07D 409/14* (2006.01)
*C07D 411/14* (2006.01)
*C09K 11/06* (2006.01)
*C07D 405/10* (2006.01)
*H10K 85/60* (2023.01)
*H10K 50/11* (2023.01)
*H10K 50/15* (2023.01)
*H10K 50/16* (2023.01)
*H10K 50/165* (2023.01)
*H10K 101/10* (2023.01)
*H10K 101/00* (2023.01)

(52) U.S. Cl.
CPC .......... *C07D 409/14* (2013.01); *C07D 411/14* (2013.01); *C09K 11/06* (2013.01); *H10K 85/615* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/165* (2023.02); *H10K 2101/10* (2023.02); *H10K 2101/90* (2023.02)

(56) References Cited

U.S. PATENT DOCUMENTS

| | | | |
|---|---|---|---|
| 2016/0028021 | A1* | 1/2016 | Zeng .................. C07D 405/10 252/301.16 |
| 2016/0093808 | A1 | 3/2016 | Adamovich et al. |
| 2016/0197285 | A1 | 7/2016 | Zeng et al. |
| 2016/0226001 | A1 | 8/2016 | Parham et al. |
| 2017/0186965 | A1 | 6/2017 | Parham et al. |
| 2017/0207399 | A1 | 7/2017 | Parham et al. |
| 2018/0037546 | A1 | 2/2018 | Sugino et al. |

FOREIGN PATENT DOCUMENTS

| | | |
|---|---|---|
| KR | 10-2000-0051826 A | 8/2000 |
| KR | 10-2012-0104246 A | 9/2012 |
| KR | 10-2013-0079237 A | 7/2013 |
| KR | 10-2015-0081451 A | 7/2015 |
| KR | 10-2016-0006633 A | 1/2016 |
| KR | 10-2016-0028524 A | 3/2016 |
| KR | 10-1614739 B1 | 4/2016 |
| KR | 10-2016-0054582 A | 5/2016 |
| TW | 201619152 A | 6/2016 |
| WO | 2015-169412 A1 | 11/2015 |
| WO | 2016-015810 A1 | 2/2016 |
| WO | 2016-129672 A1 | 8/2016 |

* cited by examiner

[FIG. 1]
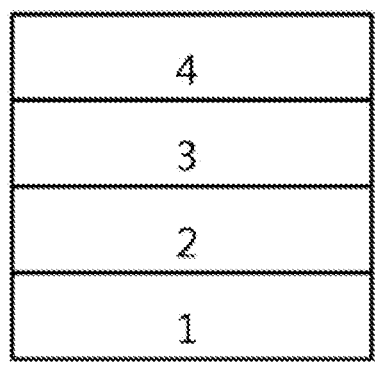
[FIG. 2]
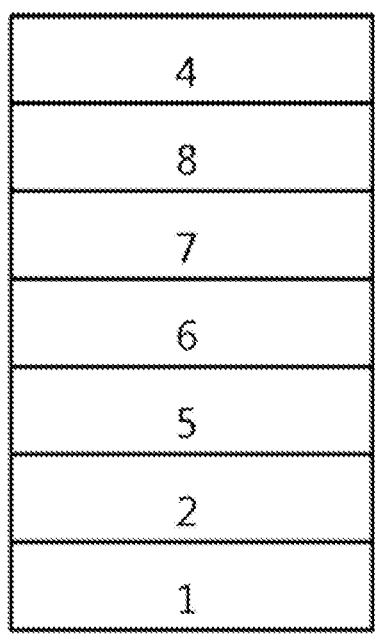

HETEROCYCLIC COMPOUND AND ORGANIC LIGHT EMITTING DEVICE COMPRISING THE SAME

CROSS-REFERENCE TO RELATED APPLICATION(S)

This application is a continuation of U.S. patent application Ser. No. 16/079,962, filed Aug. 24, 2018, which is a National Stage Application of International Application No. PCT/KR2017/010057, filed Sep. 13, 2017, and claims the benefit of Korean Patent Application No. 10-2016-0147519, filed Nov. 7, 2016 and Korean Patent Application No. 10-2017-0116136, filed Sep. 11, 2017, all of which are hereby incorporated by reference in their entirety for all purposes as if fully set forth herein.

TECHNICAL FIELD

The present invention relates to a novel heterocyclic compound and an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode to the organic material layer, and when the injected holes and the electrons meet each other, an exciton is formed, and light is emitted when the exciton falls to a ground state again.

There is a continuing demand for developing a new material for organic materials used in such organic light emitting devices.

PRIOR ART LITERATURE

Patent Literature (Patent Literature 1) Korean Patent Laid-open Publication No. 10-2000-0051826

DETAILED DESCRIPTION OF THE INVENTION

Technical Problem

It is one object of the present invention to provide a novel heterocyclic compound and an organic light emitting device comprising the same.

Technical Solution

The present invention provides a compound represented by the following Chemical Formula 1, Chemical Formula 2, or Chemical Formula 3:

[Chemical Formula 1]

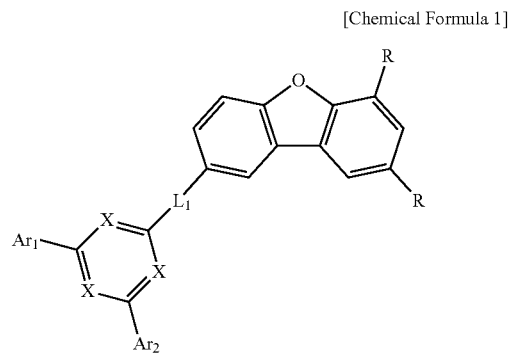

[Chemcial Formula 2]

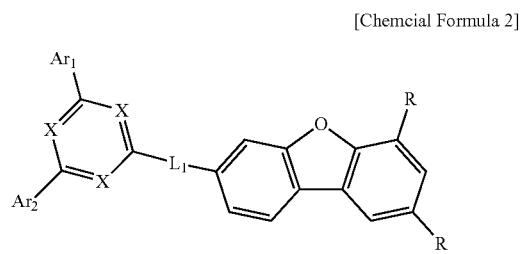

[Chemical Formula 3]

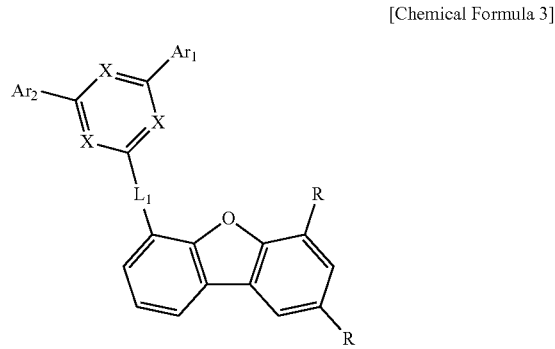

in Chemical Formulas 1 to 3, each X is independently N, or CH, $L_1$ is a single bond; or a substituted or unsubstituted $C_{6-60}$ arylene, $Ar_1$ and $Ar_2$ are each independently a substituted or unsubstituted $C_{6-60}$ aryl; or a substituted or unsubstituted $C_{2-60}$ heteroaryl containing at least one heteroatom selected from the group consisting of N, O, S and Si, R are identical to each other and are represented by -$L_2$-$Ar_3$, $L_2$ is a single bond; a substituted or unsubstituted $C_{6-60}$ arylene; or a substituted or unsubstituted $C_{2-60}$ heteroarylene containing at least one heteroatom selected from the group consisting of N, O, S and Si, Ar₃ is a substituted or unsubstituted $C_{6-60}$ aryl; or a substituted or unsubstituted $C_{2-60}$ heteroaryl containing at least one heteroatom selected from the group consisting of N, O, S and Si, provided that R is not an unsubstituted phenyl.

In addition, the present invention provides an organic light emitting device comprising a first electrode; a second electrode provided to face the first electrode; and one or more organic material layers provided between the first electrode and the second electrode, wherein one or more of the organic layers includes a compound represented by Chemical Formula 1.

Advantageous Effects

The compound represented by Chemical Formula 1 can be used as a material of an organic material layer of an organic light emitting device and can exhibit improved efficiency, a low driving voltage and/or improved lifetime characteristics of the organic light emitting device, in particular, the compound represented by Chemical Formula 1 can be used as a hole injection material, a hole transport material, a hole injection and hole transport material, a light emitting material, an electron transport material or an electron injection material.

BRIEF DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting element comprising a substrate 1, an anode 2, a hole injection layers, a hole transport layers, a light emitting layer 7, an electron transport layer 8 and a cathode 4.

DETAILED DESCRIPTION OF THE EMBODIMENTS

Hereinafter, the present invention will be described in more detail to facilitate understanding of the present invention.

The present invention provides a compound represented by the Chemical Formula 1.

In the present specification, ┆ and ⌇ means a bond connected to another substituent group, s used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl groups; an aralkenyl group; an alkylaryl group; an alkylamine group; an aralkylamine group; a heteroarylamine group; an arylamine group; an arylphosphine group; or heterocyclic group containing at least one of N, O, and S atoms, or there is no substituent group, or substitution is performed by a substituent group where two or more substituent groups of the exemplified substituent groups are connected or there is no substituent group. For example, the term "substituent group where two or more substituent groups are connected" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40 carbon atoms. Specifically, the carbonyl group may be compounds having the following structures, but is not limited thereto.

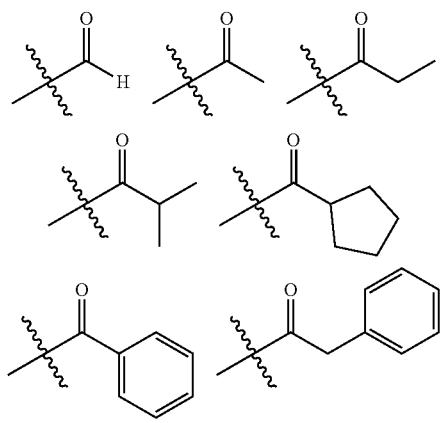

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

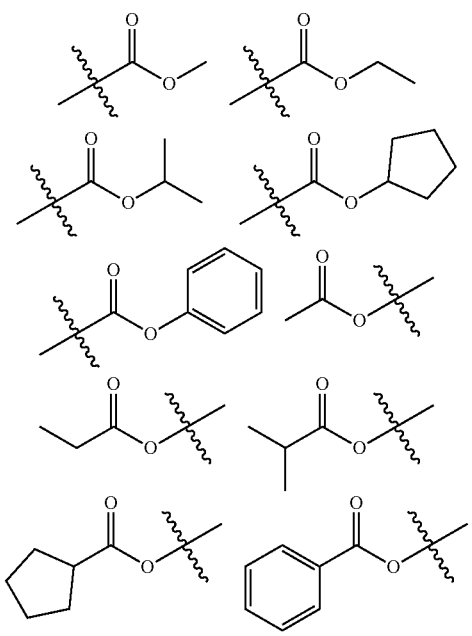

In the present specification, the number of carbon atoms in an imide group is not particularly limited but is preferably 1 to 25. Specifically, the imide group may be compounds having the following structures, but is not limited thereto.

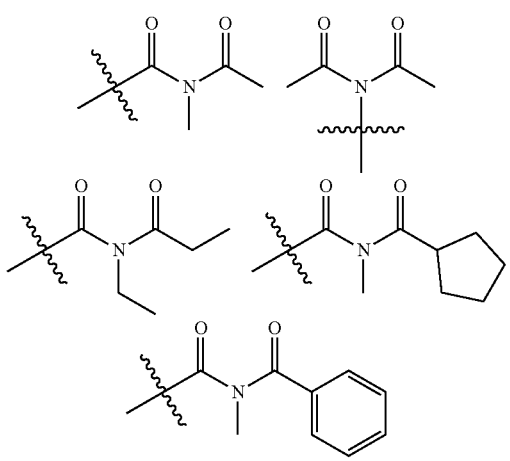

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, an alkyl group may be a straight chain or a branched chain, and the number of carbon atoms thereof is not particularly limited but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methyl hexyl, 5-methyl hexyl, and the like, but are not limited thereto.

In the present specification, the alkenyl group may be a straight chain or a branched chain, and the number of carbon atoms thereof is not particularly limited but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group may be substituted, and two substituent groups may be bonded to each other to form a spiro structure. In the case where the fluorenyl group is substituted,

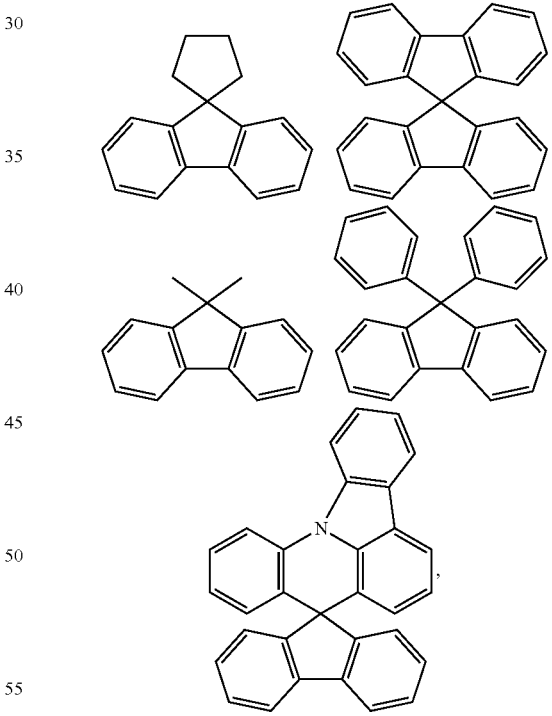

and the like can be formed. However, the structure is not limited thereto.

In the present specification, the heterocyclic group is a heterocyclic group containing one or more of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group, in the present specification, the heteroaryl in the heteroarylamines can be applied to the aforementioned description of the heterocyclic group, in the present specification, the alkenyl group in the aralkenyl group is the same as the aforementioned examples of the alkenyl group. In the present specification, the aforementioned description of the aryl group may be applied except that the arylene is a divalent group, in the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups, in the present specification, the aforementioned description of the heterocyclic group can be applied, except that the heterocycle is not a monovalent group but formed by combining two substituent groups.

Preferably, the Chemical Formula 1 is represented by the following Chemical Formula 1-1:

[Chemical Formula 1-1]

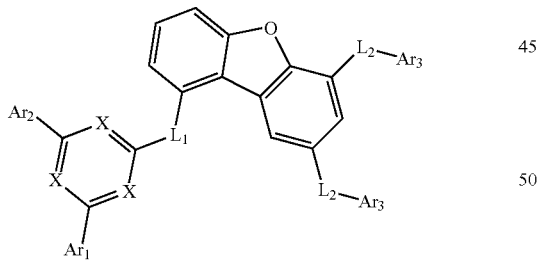

Preferably, all of X are N.

Preferably, $L_1$ is a single bond; or phenylene.

Preferably, $Ar_1$ and $Ar_2$ are each independently phenyl, or biphenylyl.

Preferably, $L_2$ is a single bond; or phenylene.

Preferably, $Ar_3$ is a $C_{6-60}$ aryl unsubstituted or substituted with one or more deuterium, or one or more cyano; or a $C_{2-60}$ heteroaryl containing at least one heteroatom selected from the group consisting of N, O, S and Si, which is substituted with one or more deuterium, or one or more cyano.

Preferably, $Ar_3$ is any one selected from the group consisting of:

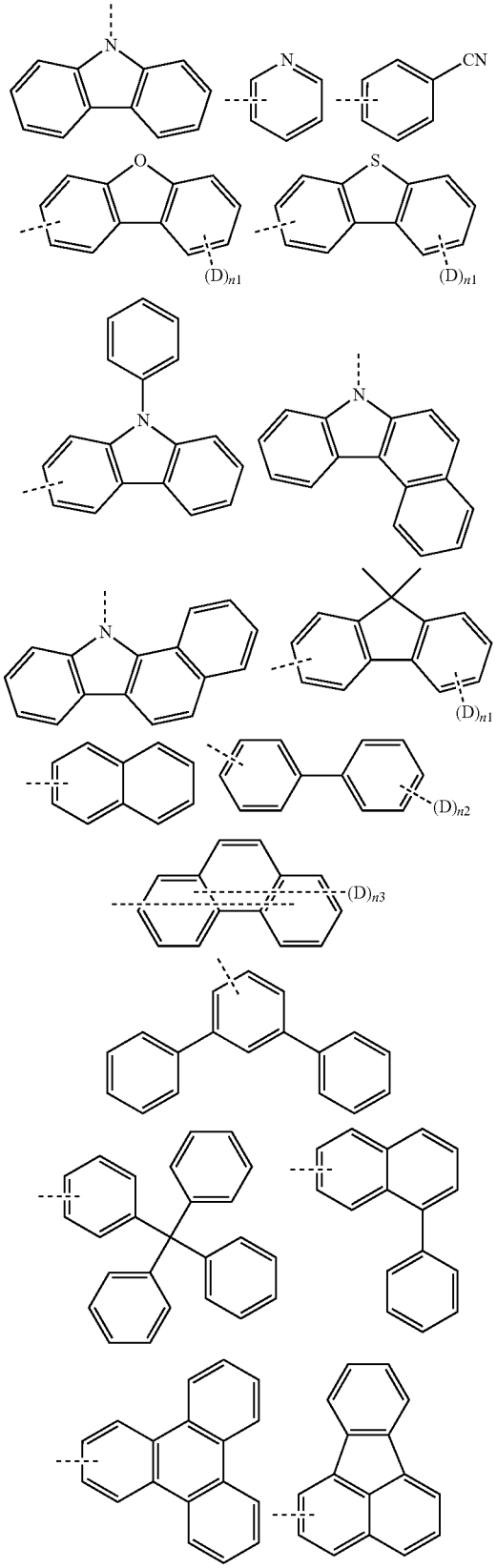

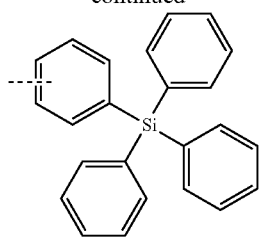

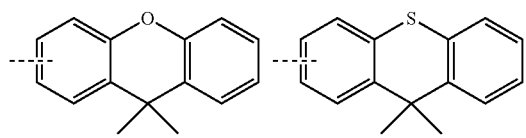

wherein, n1 is an integer of 0 to 4, n2 is an integer of 0 to 5, and n3 is an integer of 0 to 9.

Preferably, R is phenyl substituted with cyano, biphenylyl unsubstituted or substituted with one to five deuterium, naphthyl, phenanthrenyl unsubstituted or substituted with one to five deuterium, dimethylfluorenyl substituted with one to five deuterium, benzofuranyl substituted with one to five deuterium, benzothiophenyl, carbazolyl, pyridinephenyl, 9,9-dimethyl-xanthenyl, or 9,9-dimethyl-thioxanthenyl.

Preferably, the compound represented by the Chemical Formula 1 can be selected from the group consisting of the following compounds:

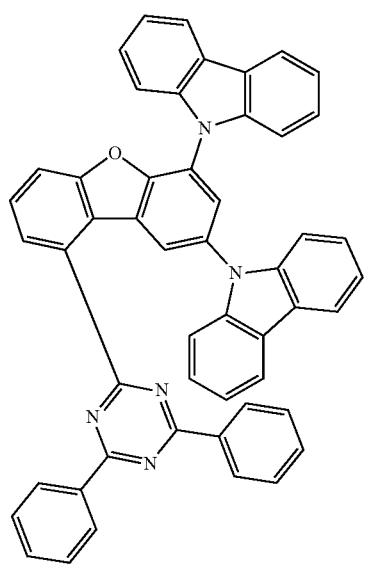

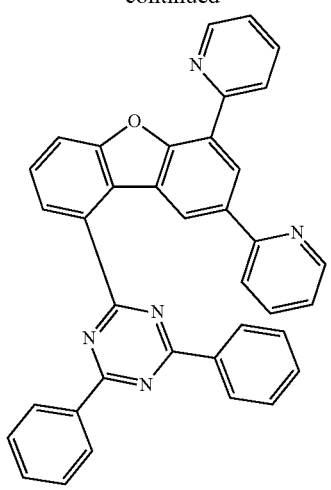

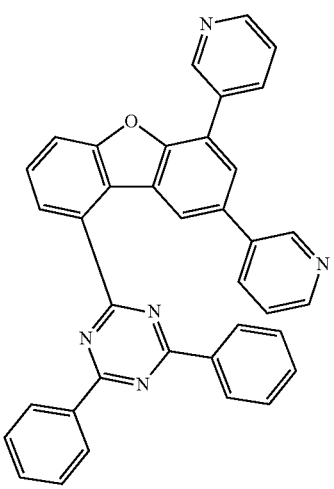

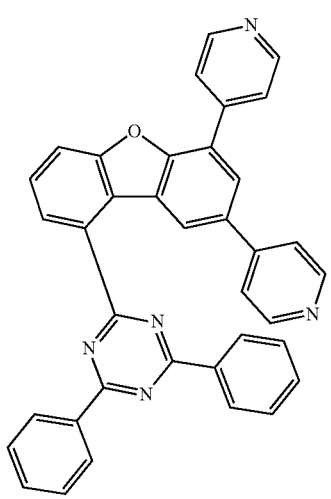

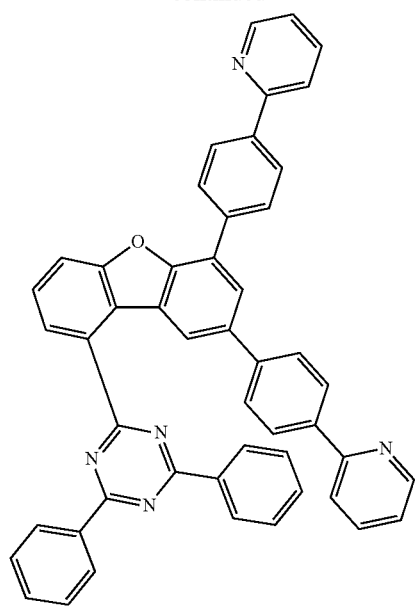
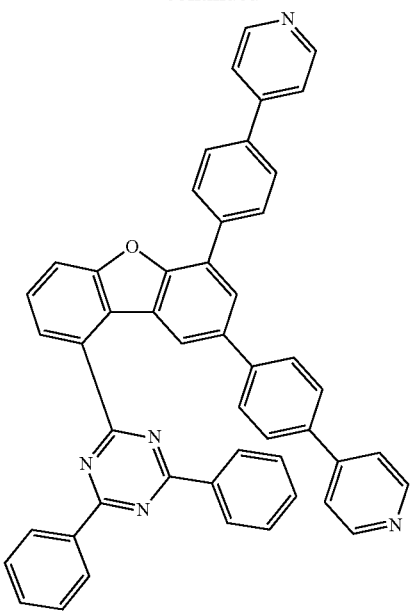
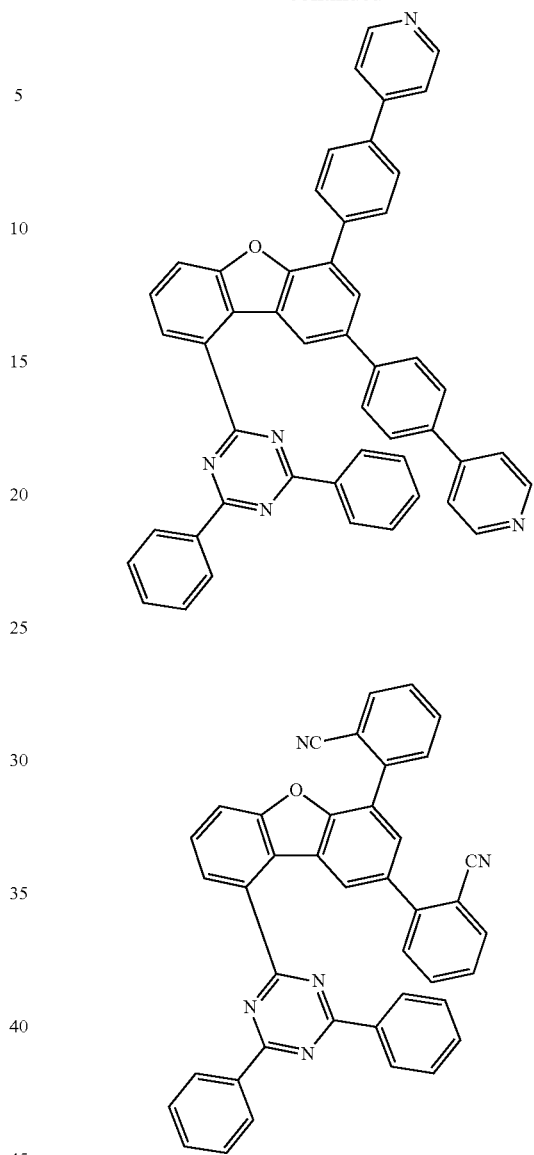
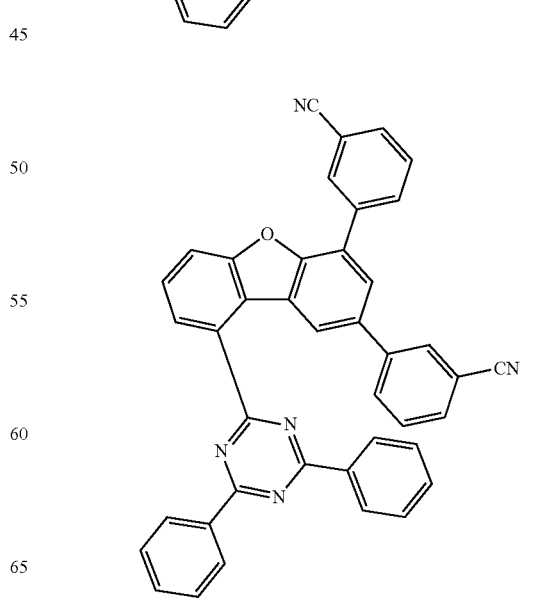

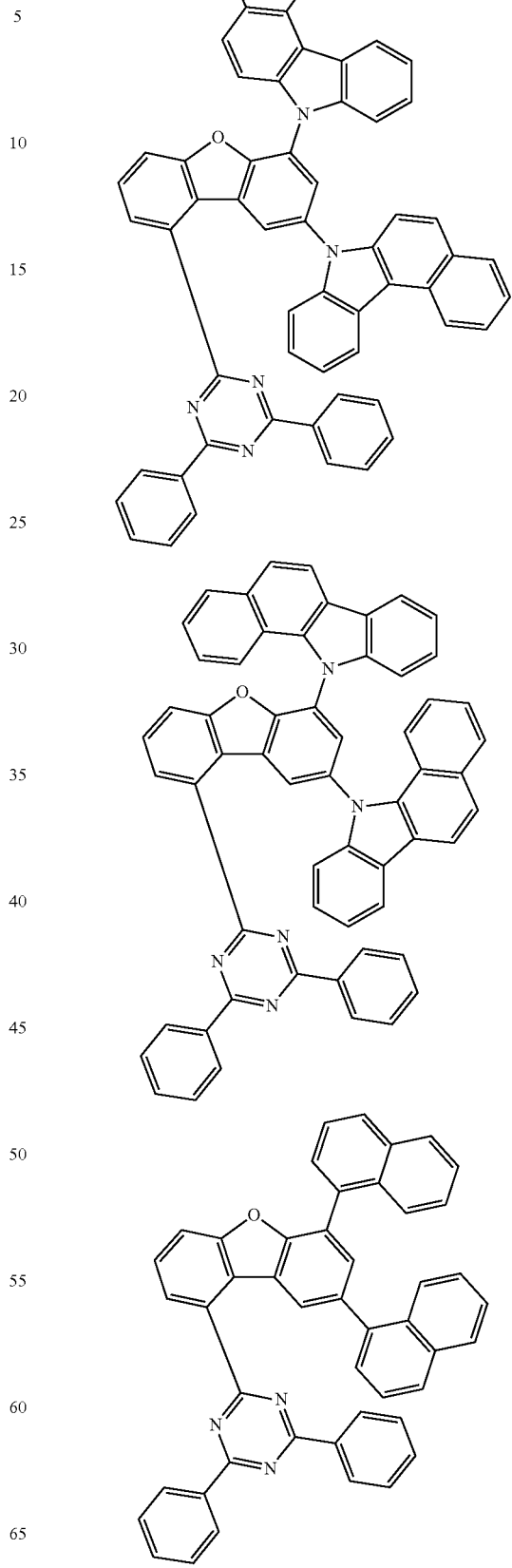

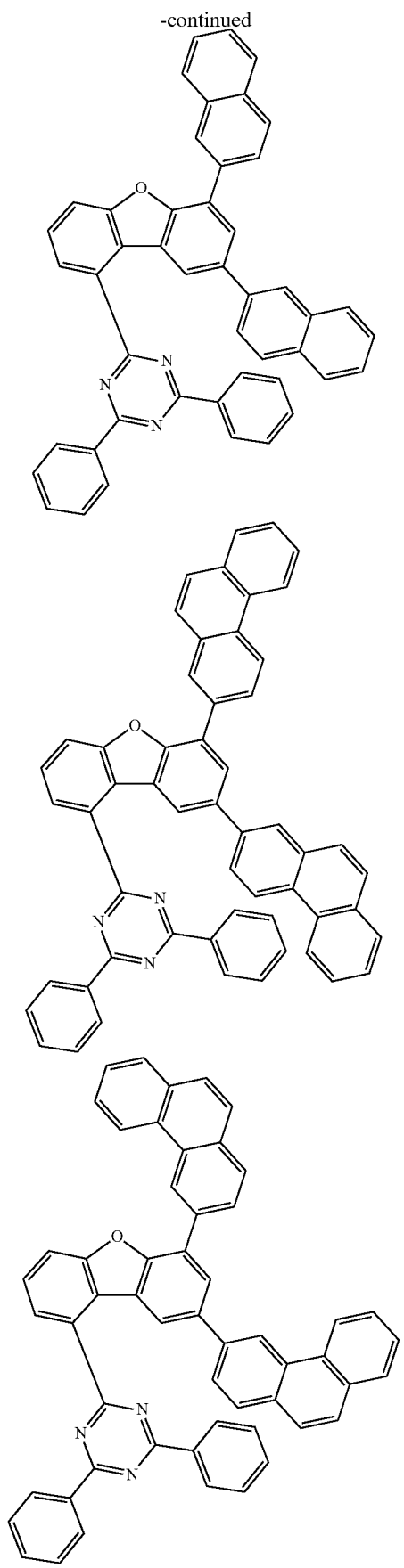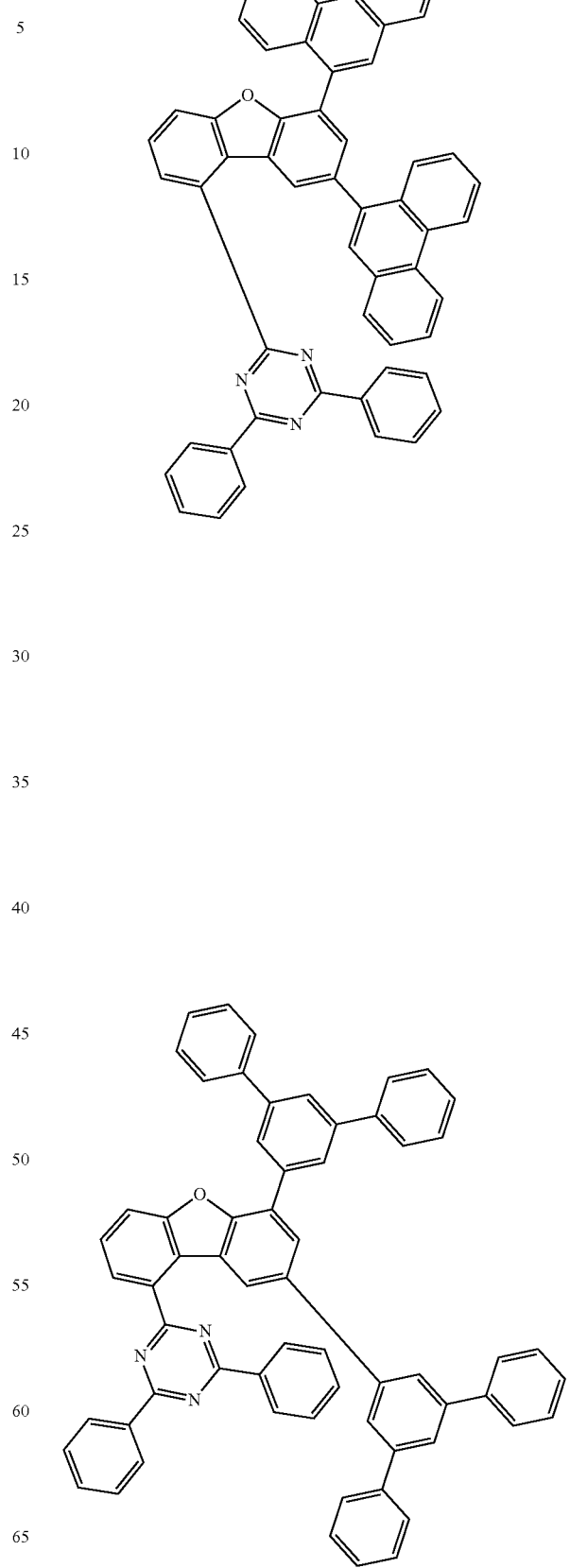

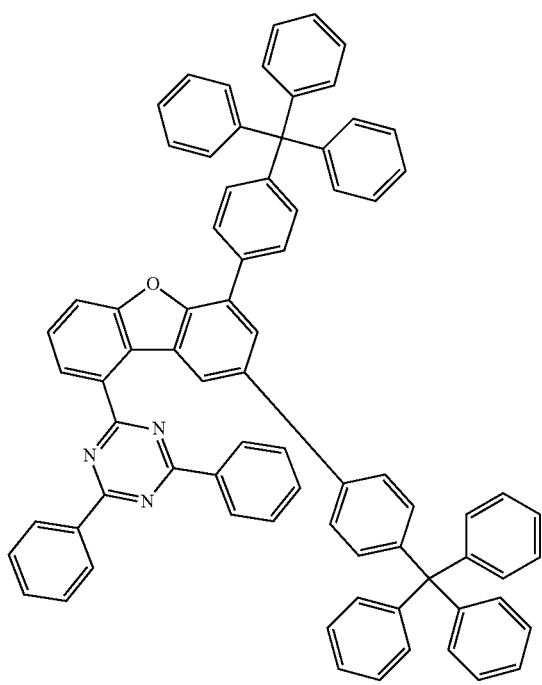
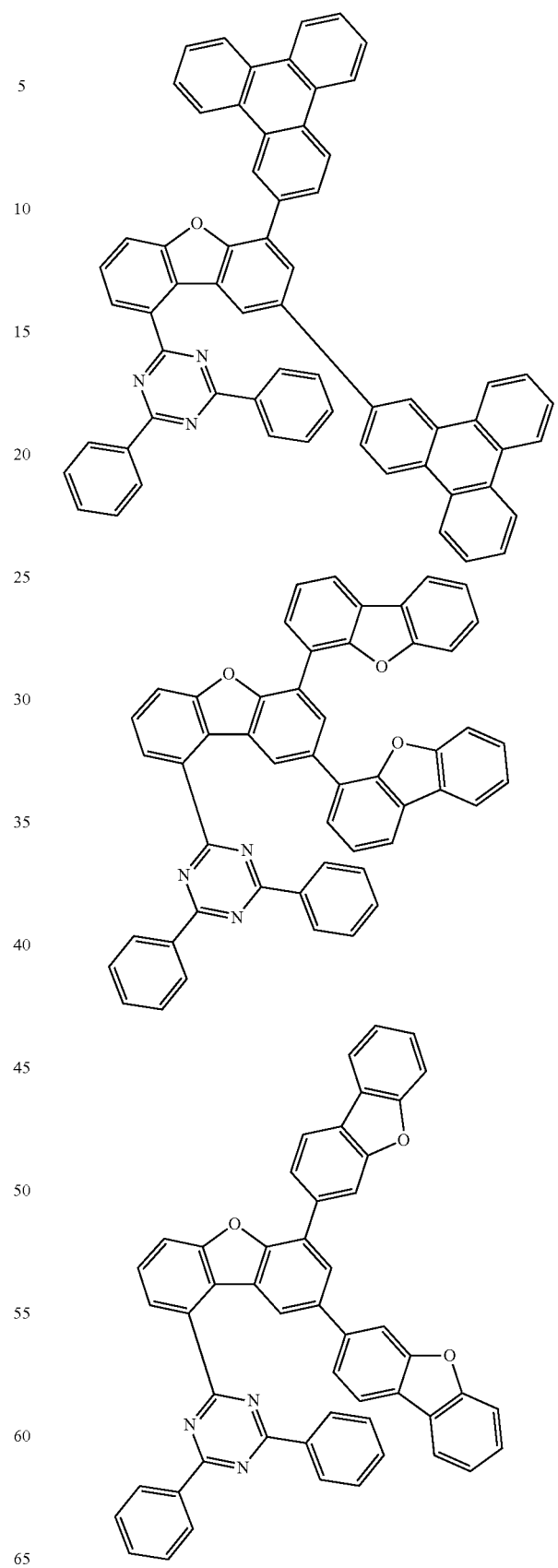

-continued
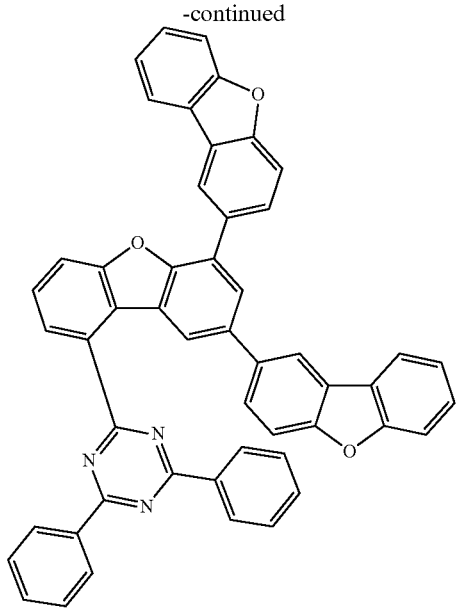
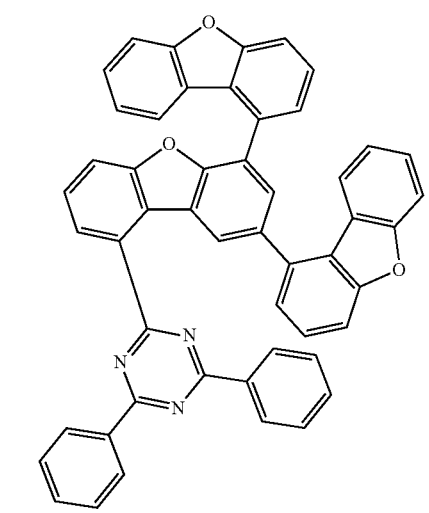
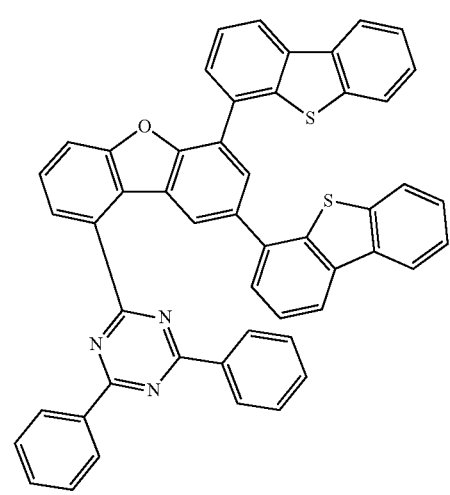
-continued
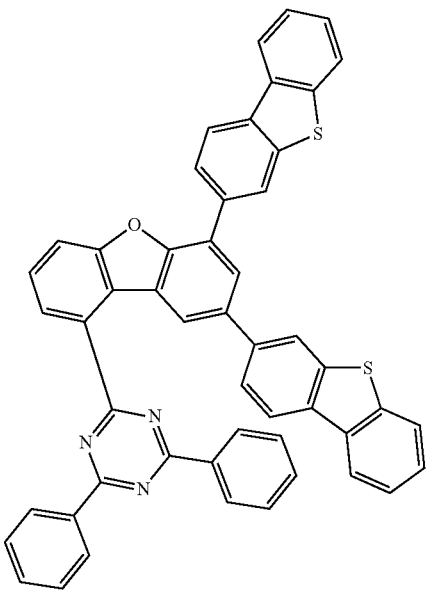
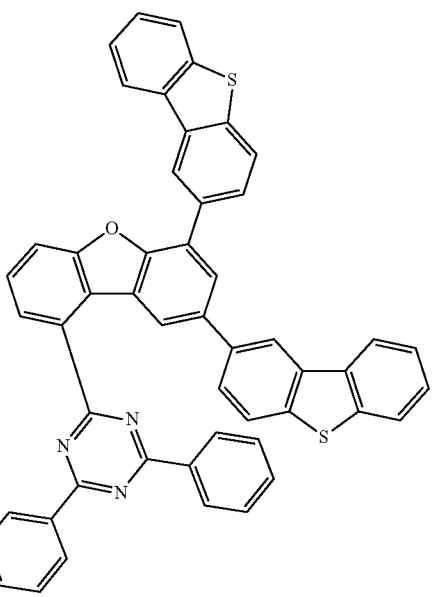
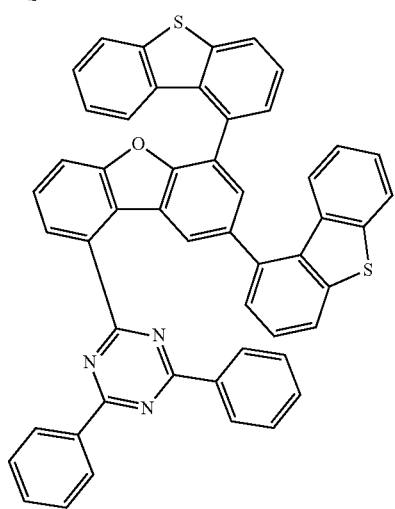

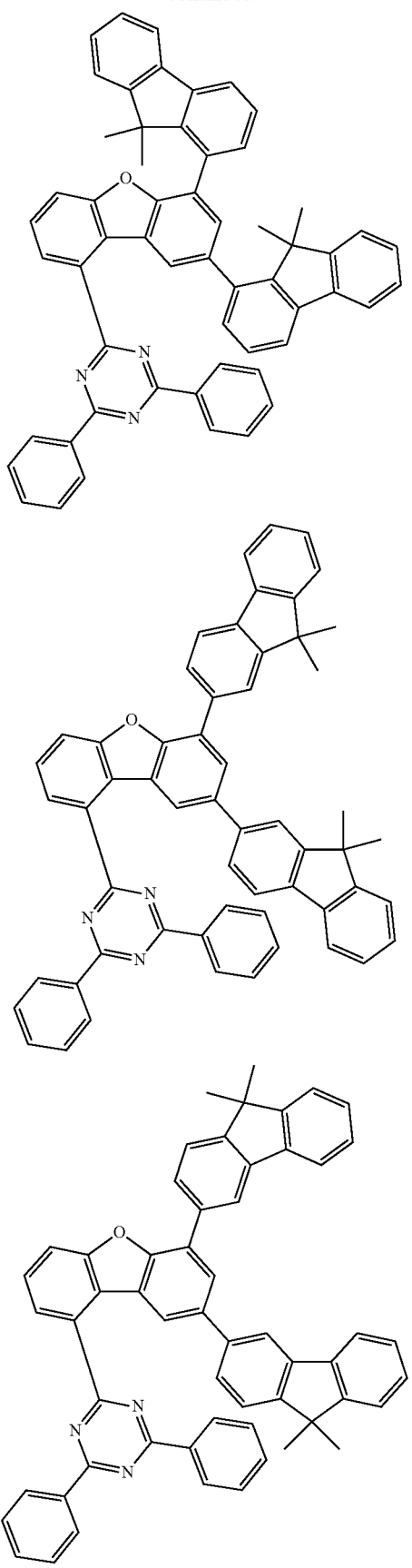 [SMILES: CC1(C)c2ccccc2-c2cccc(-c3cc(-c4cccc5c4C(C)(C)c4ccccc4-5)c4oc5cccc(-c6nc(-c7ccccc7)nc(-c7ccccc7)n6)c5c4c3)c21 ; CC1(C)c2ccccc2-c2ccc(-c3cc(-c4ccc5c(c4)C(C)(C)c4ccccc4-5)c4oc5cccc(-c6nc(-c7ccccc7)nc(-c7ccccc7)n6)c5c4c3)cc21 ; CC1(C)c2ccccc2-c2cc(-c3cc(-c4ccc5c(c4)-c4ccccc4C5(C)C)c4oc5cccc(-c6nc(-c7ccccc7)nc(-c7ccccc7)n6)c5c4c3)ccc21]
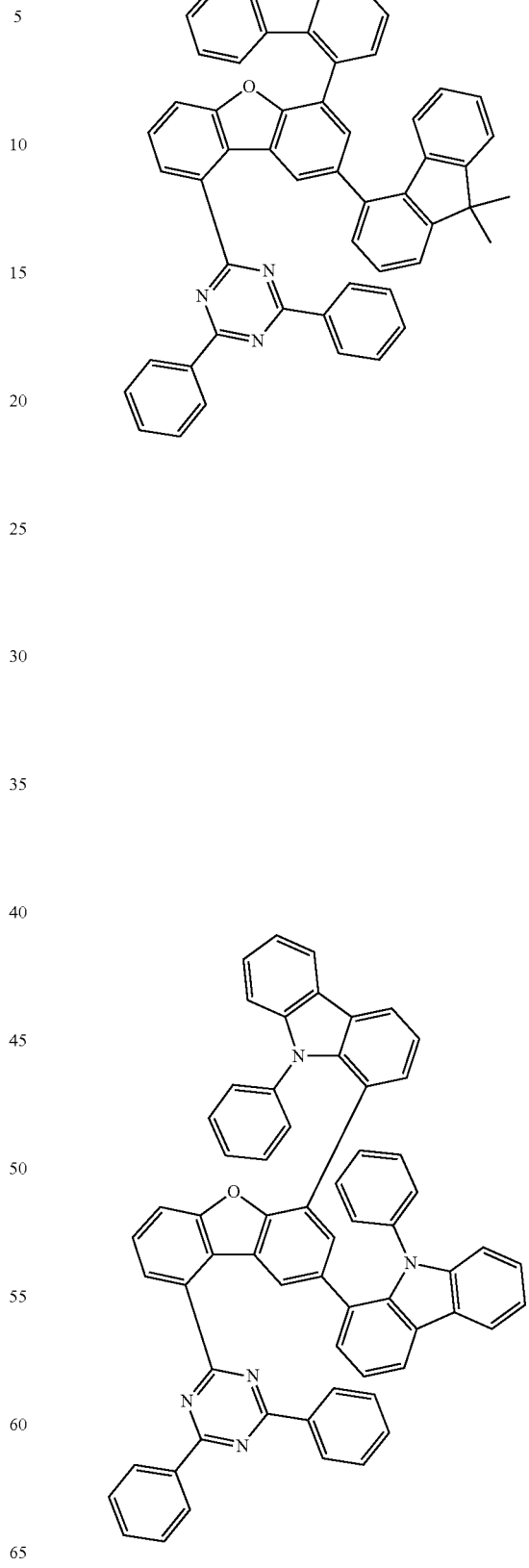

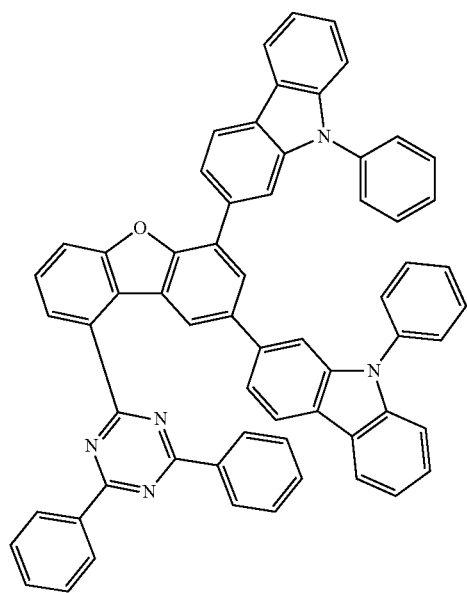
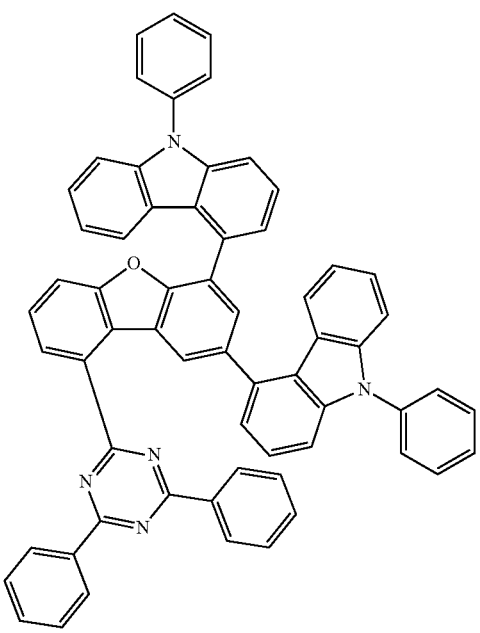
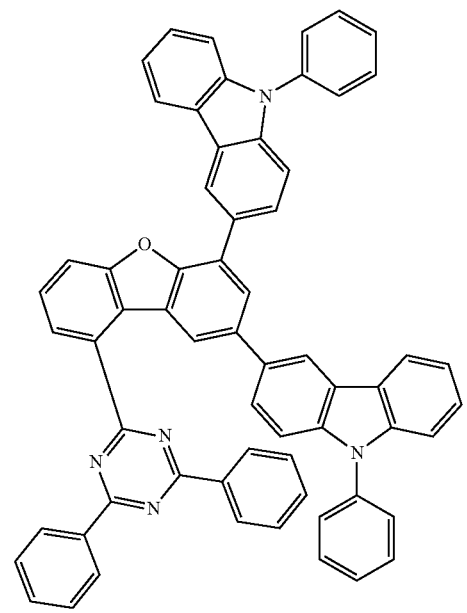
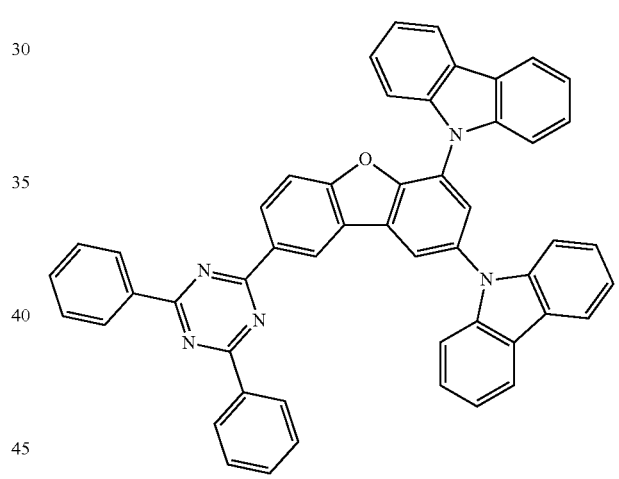
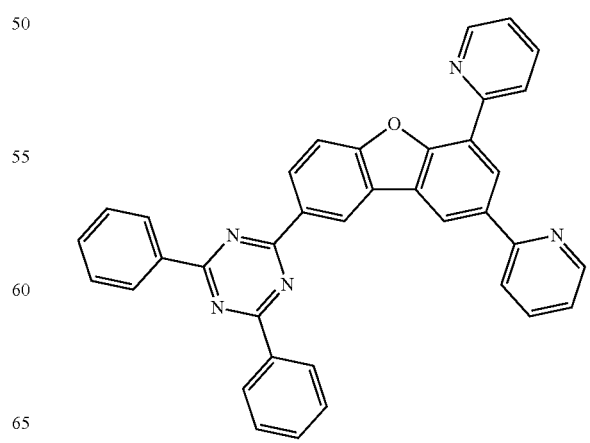

-continued
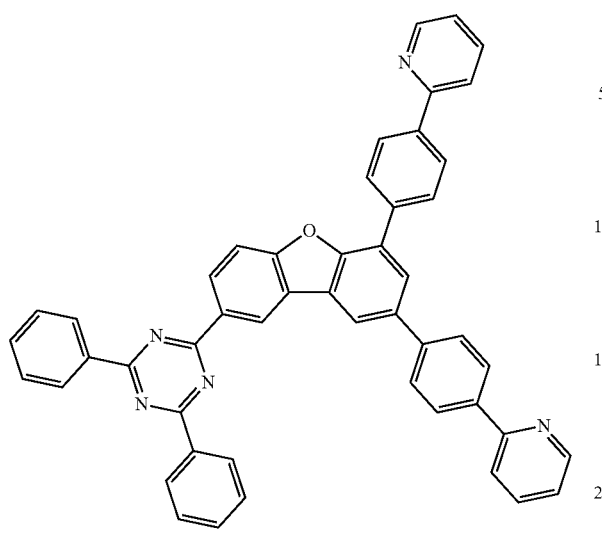
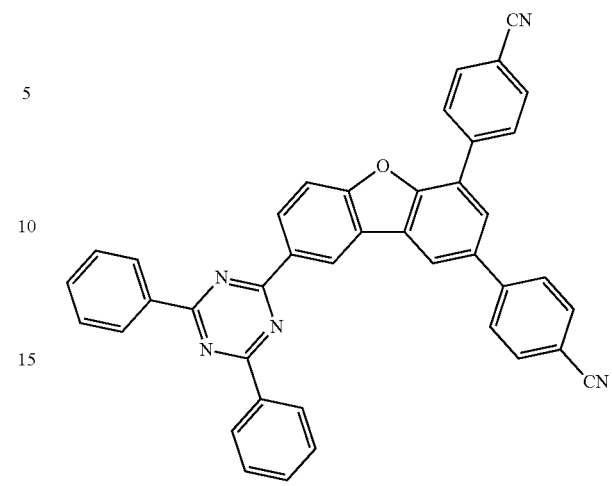
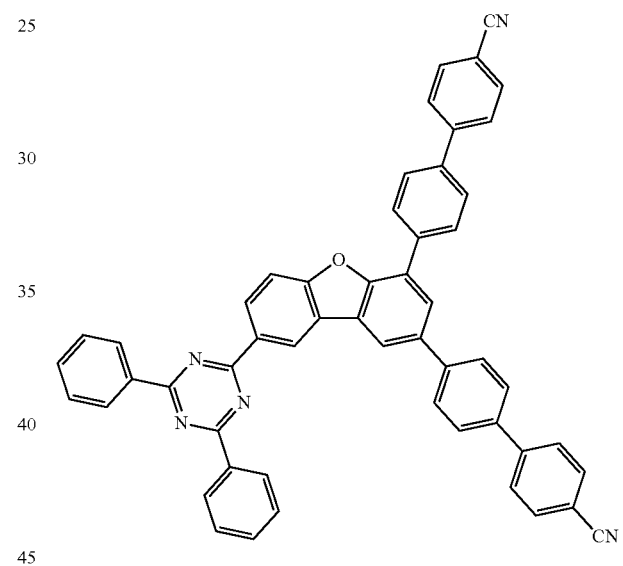
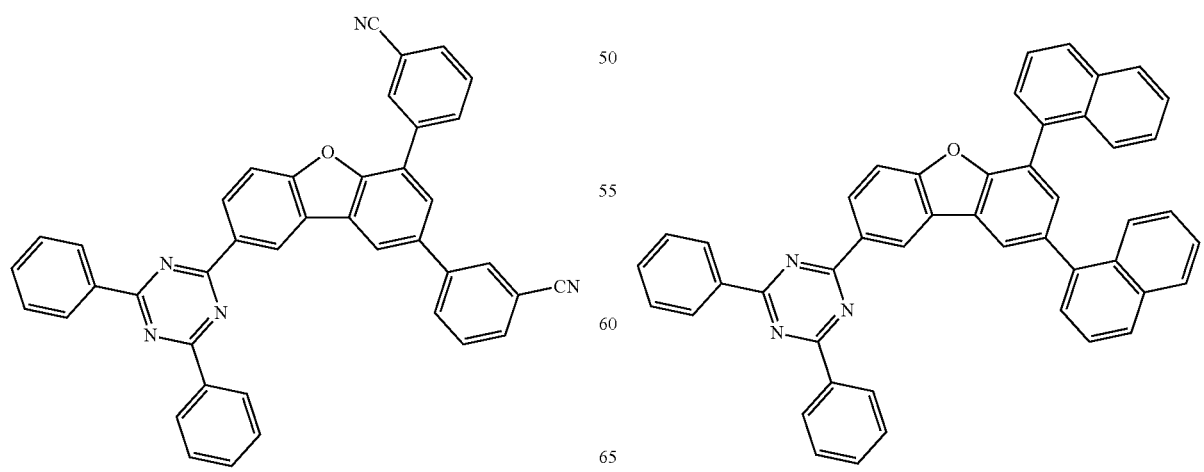

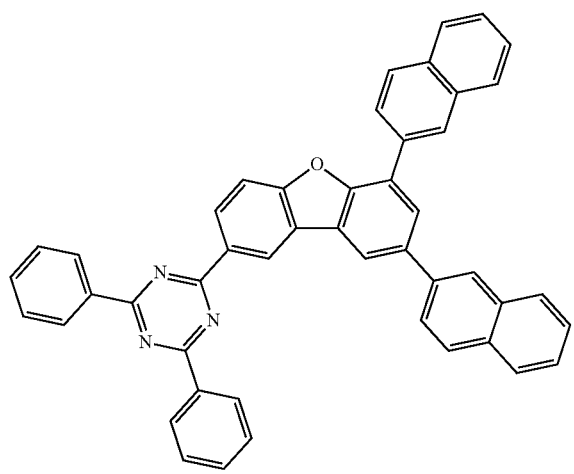
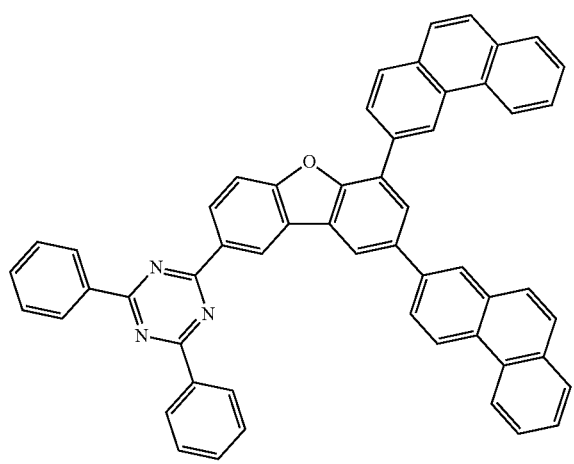
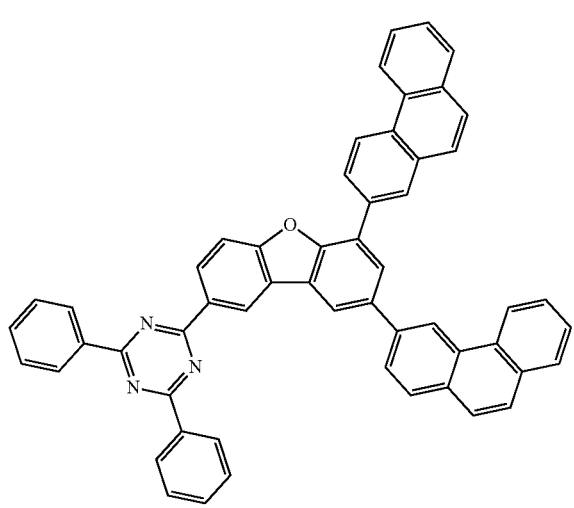
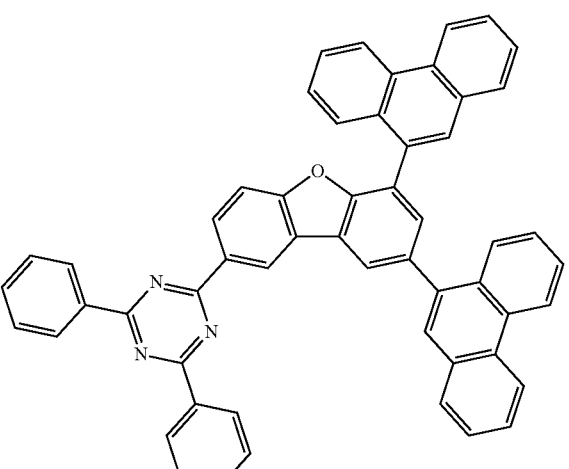
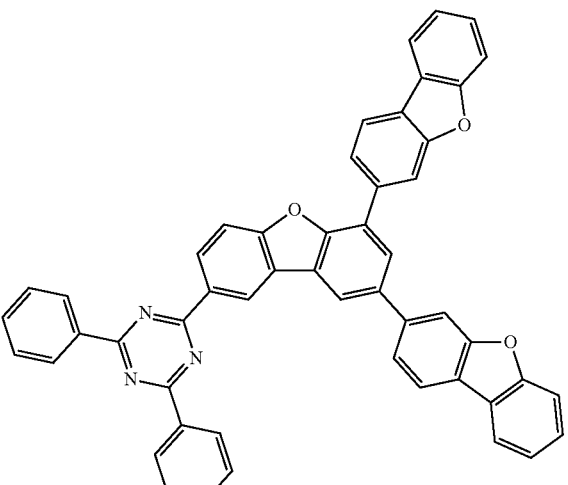

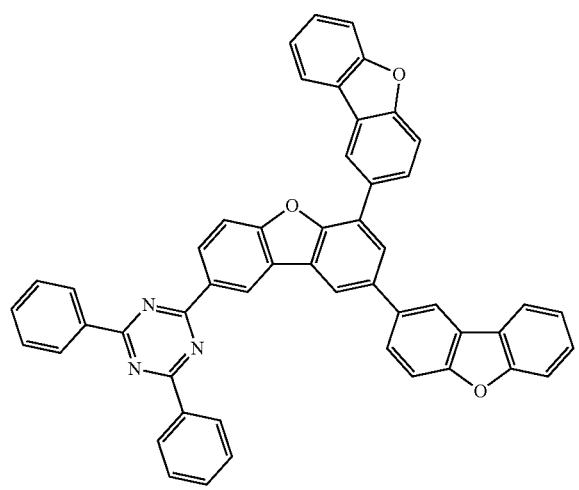
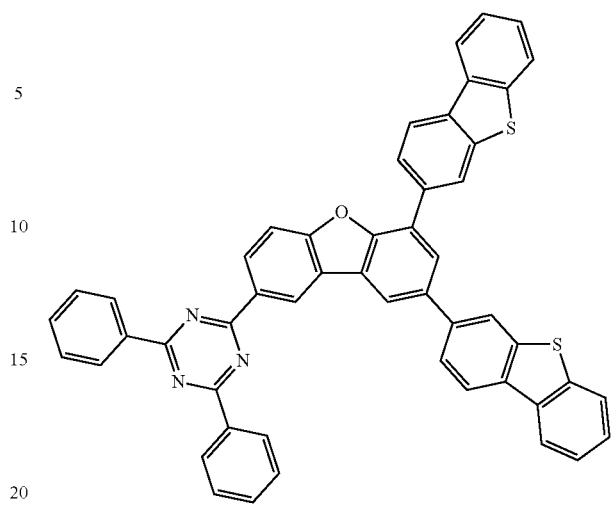
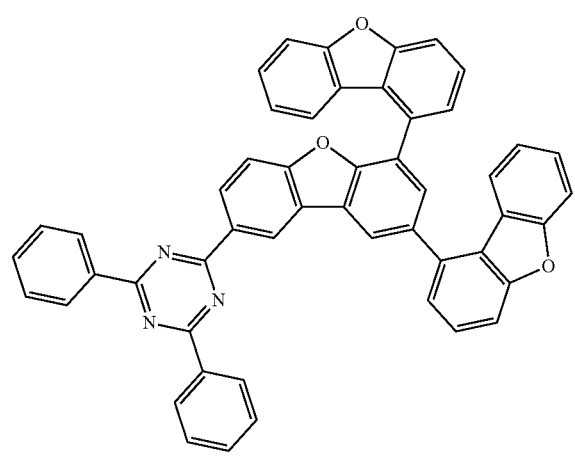
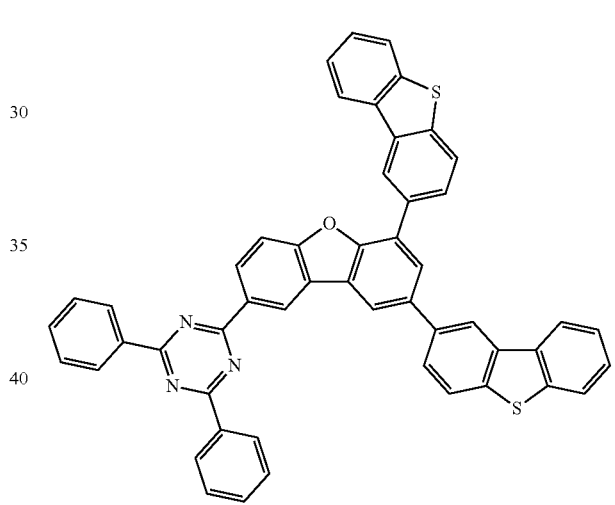
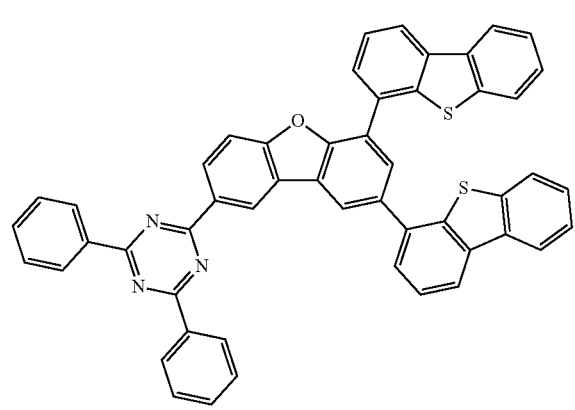
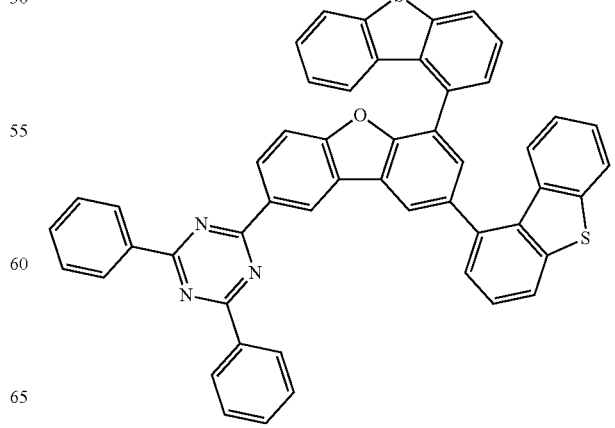

31
-continued
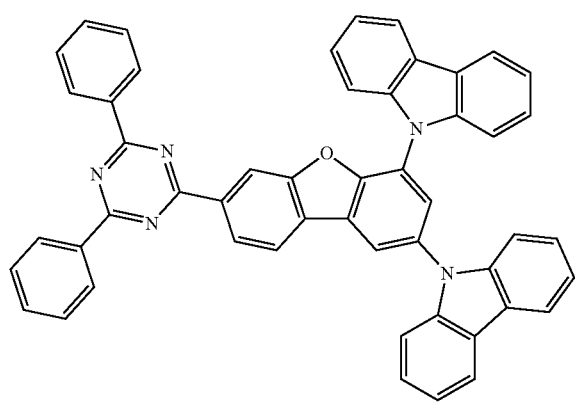
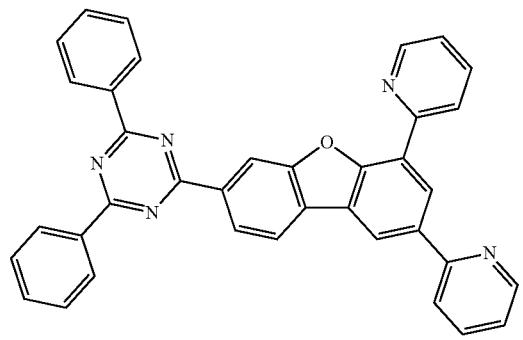
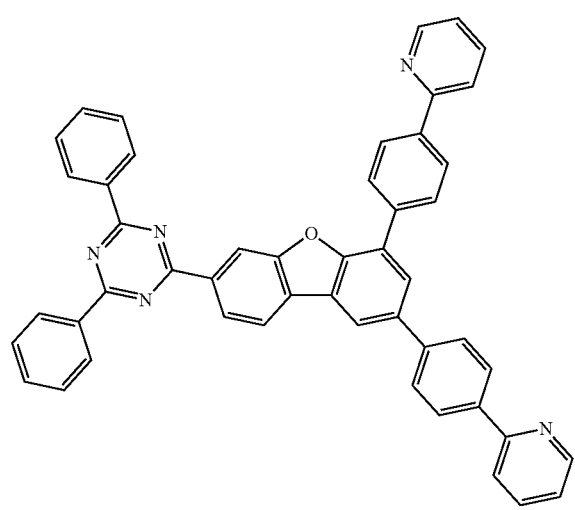
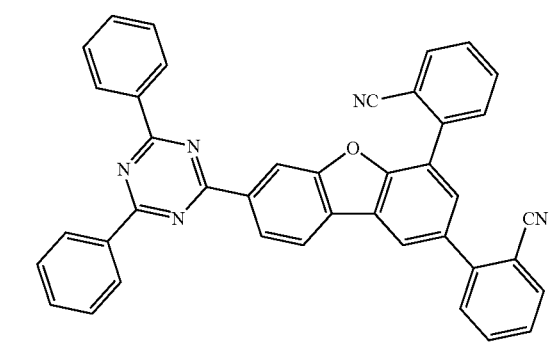
32
-continued
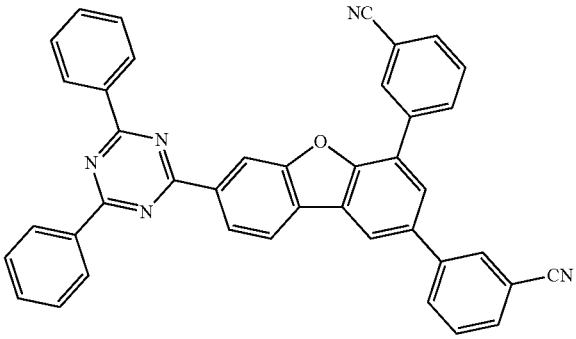
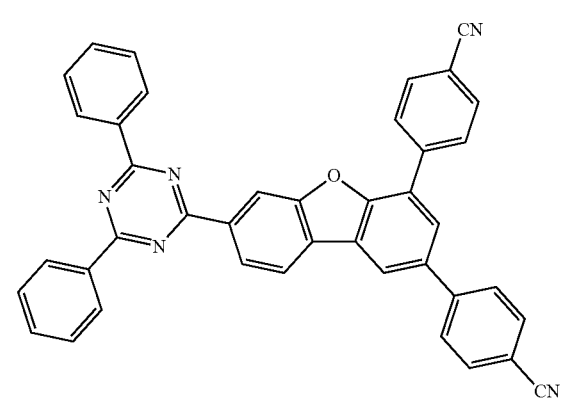
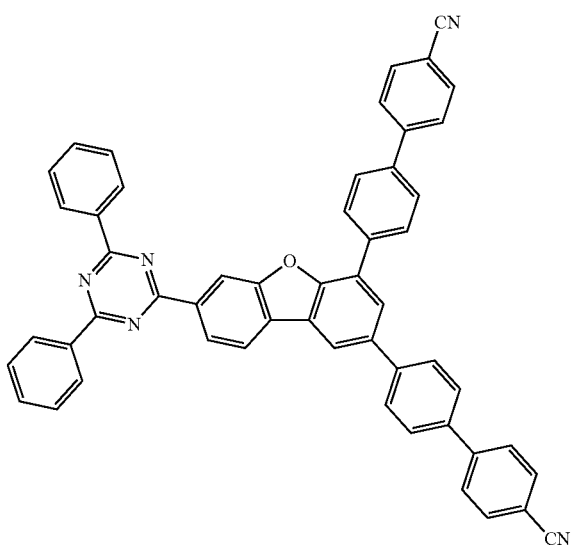
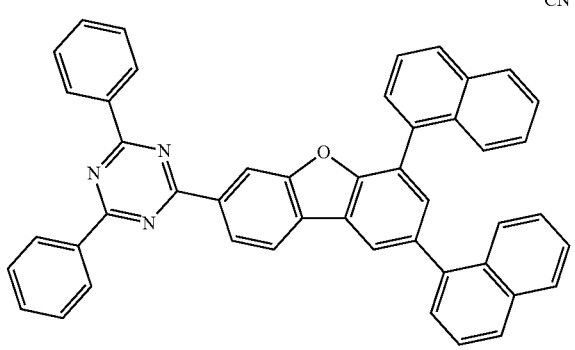

33
-continued
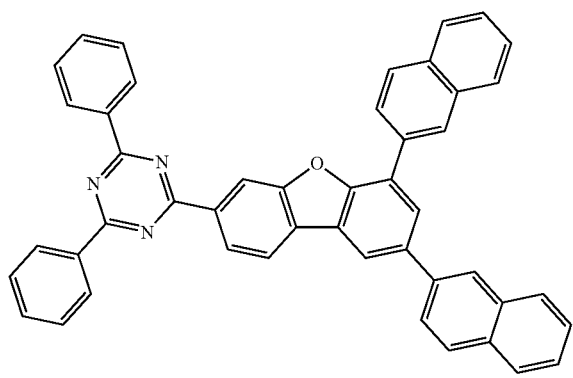
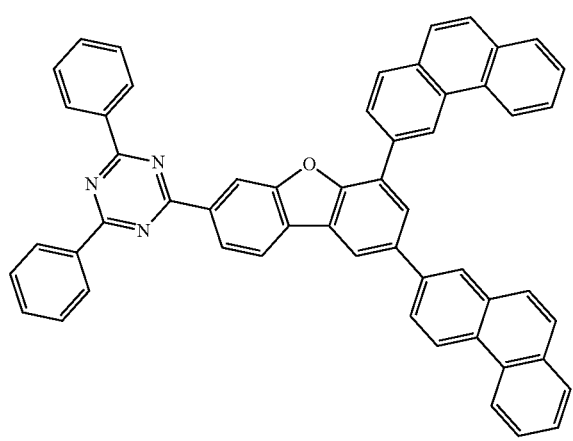
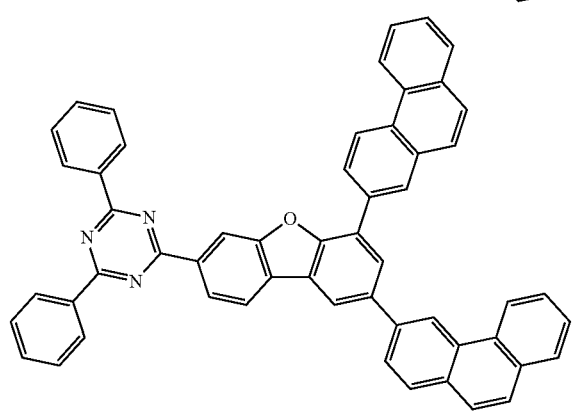
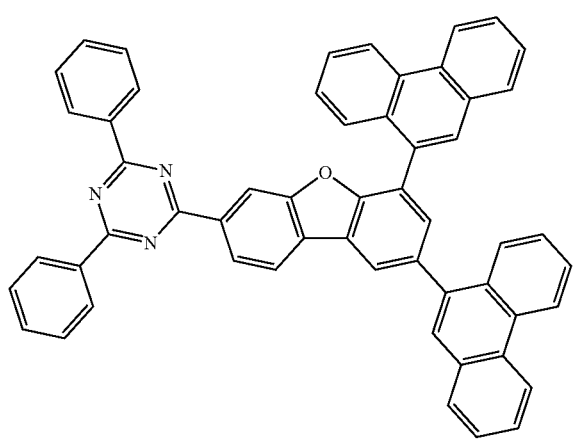
34
-continued
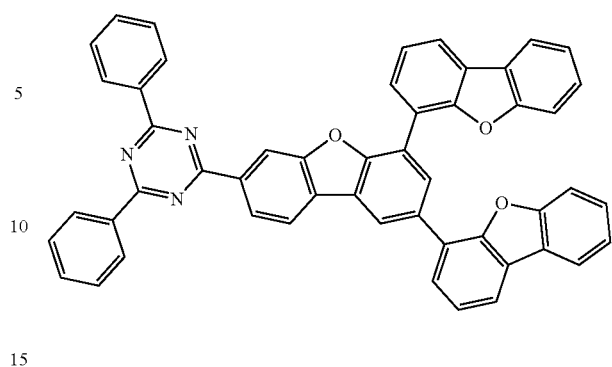
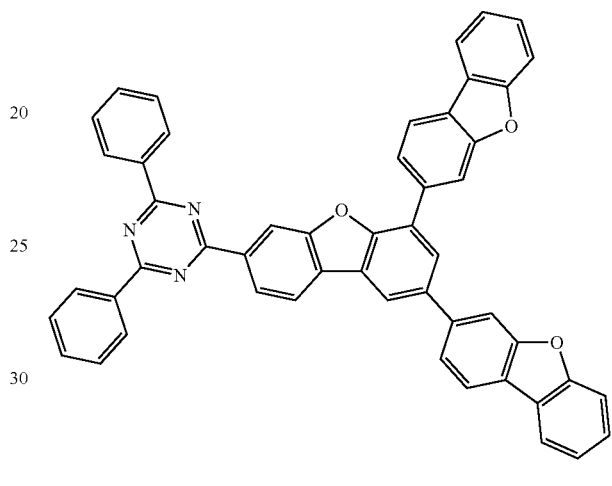
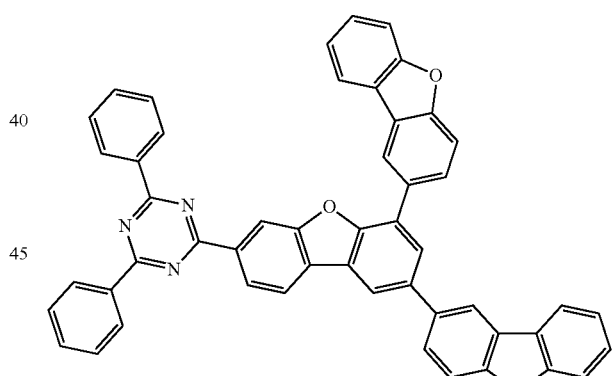
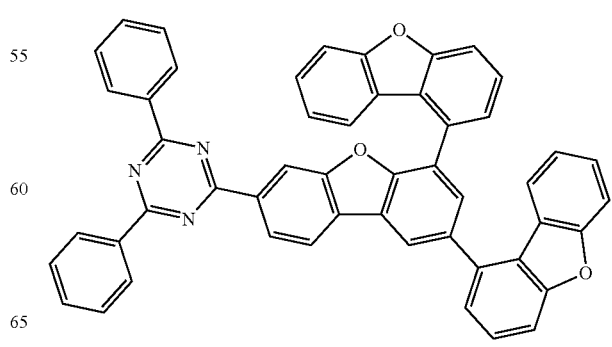

35
-continued
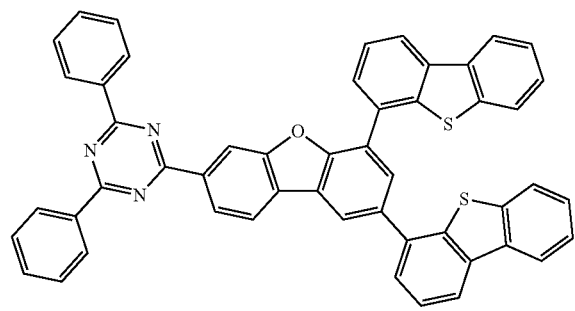
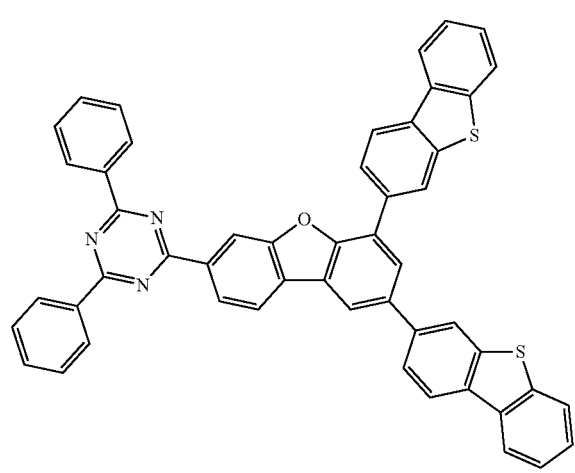
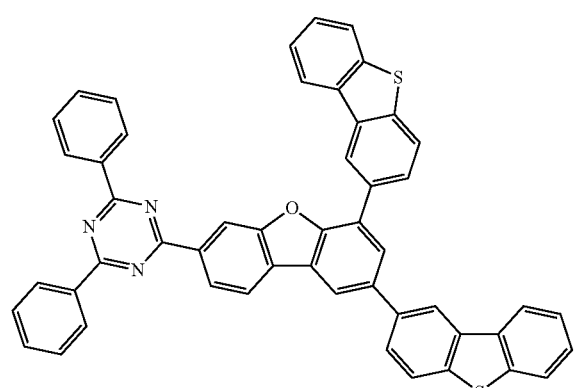
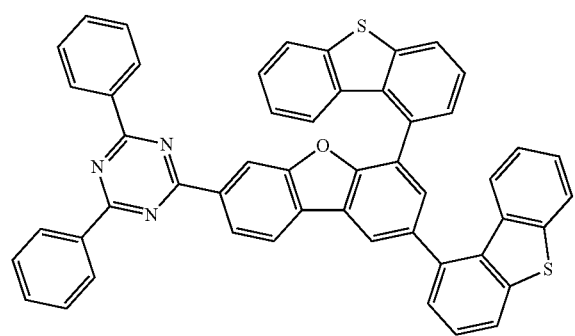
36
-continued
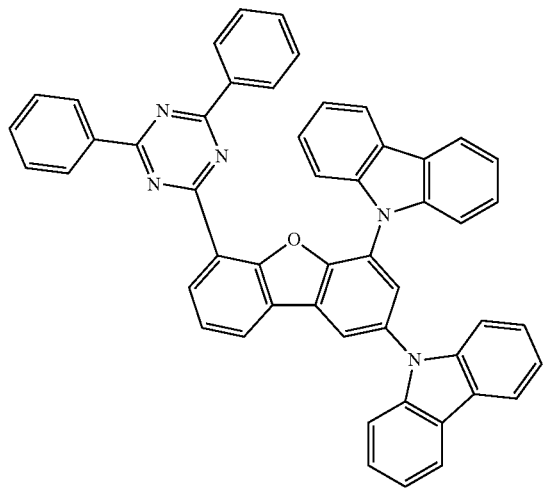
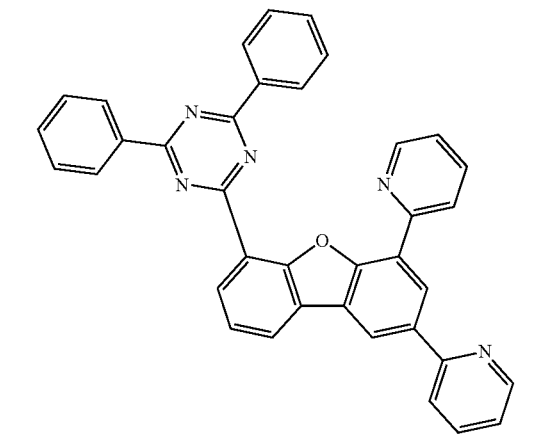
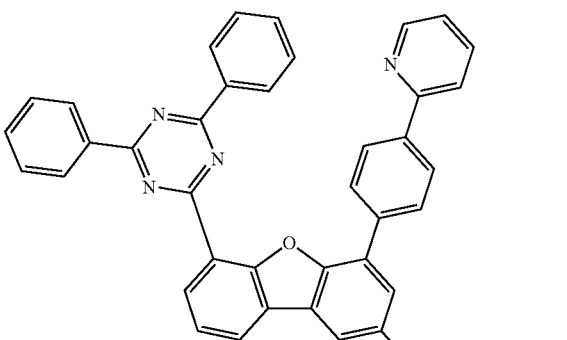

37
-continued
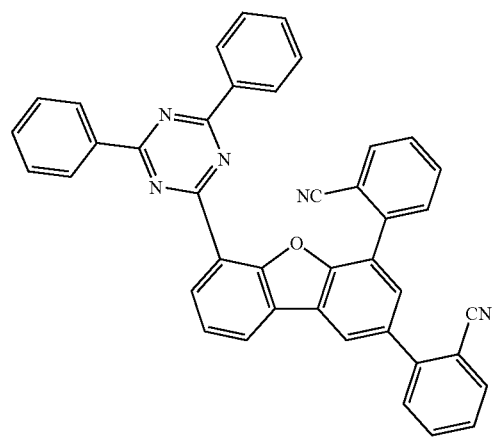
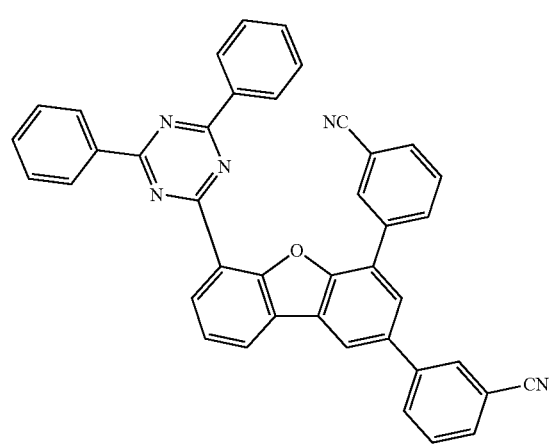
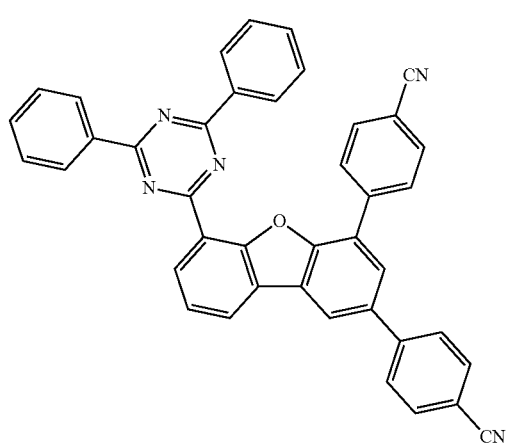
38
-continued
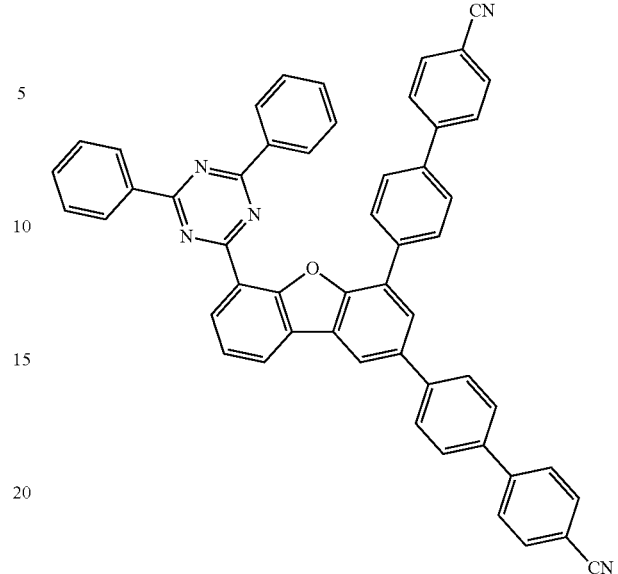
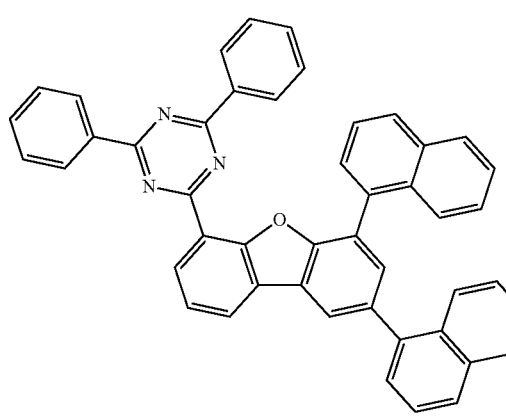
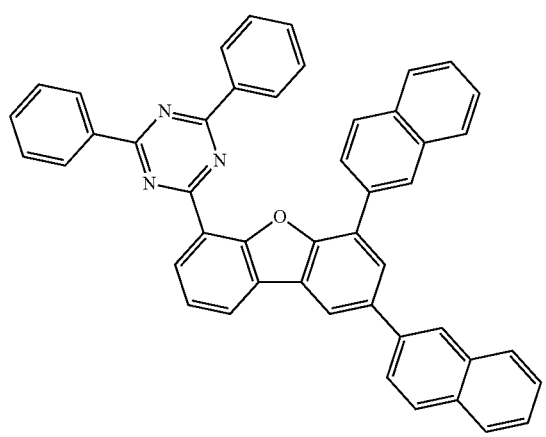

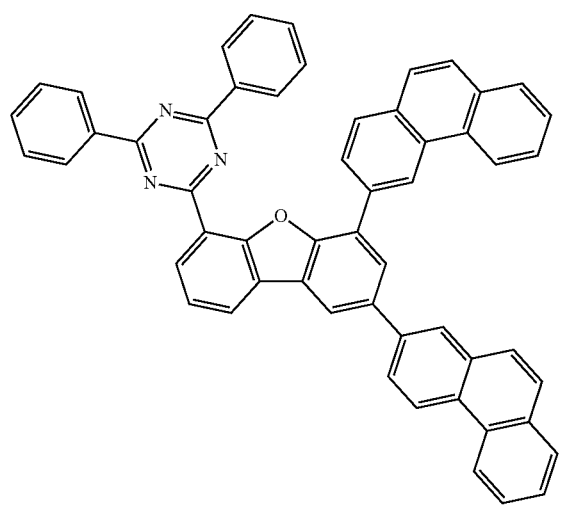
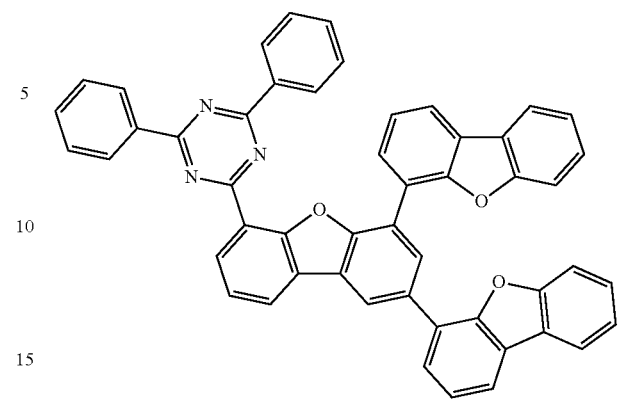
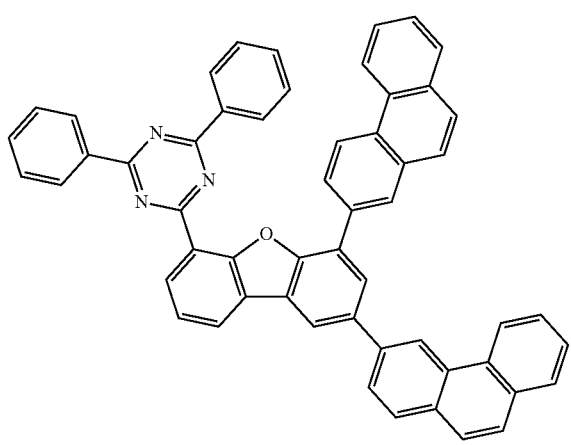
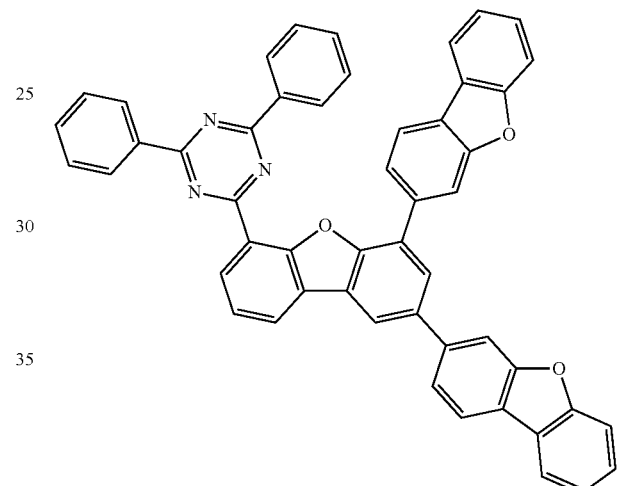
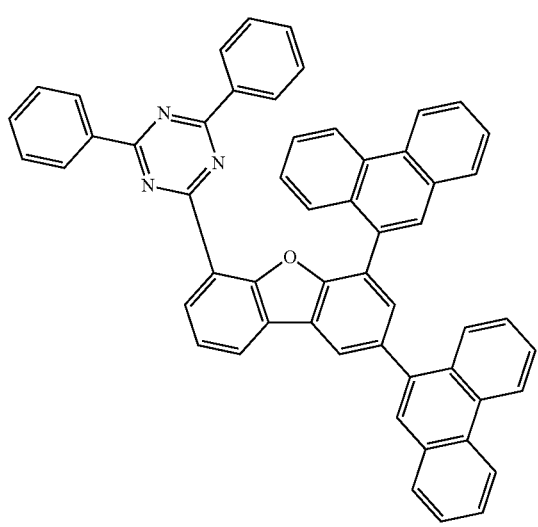
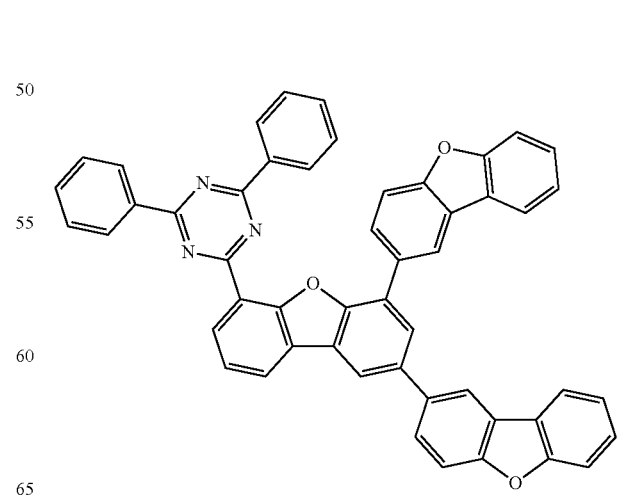

41
-continued
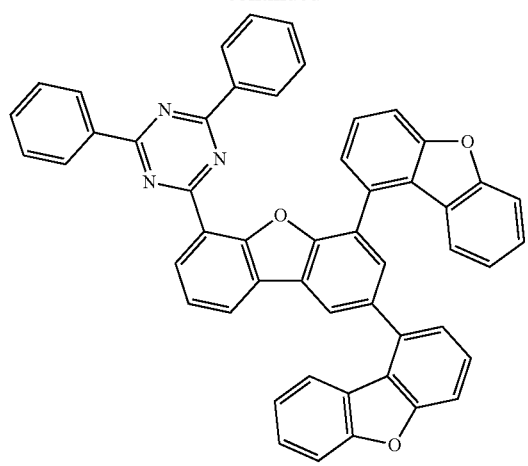
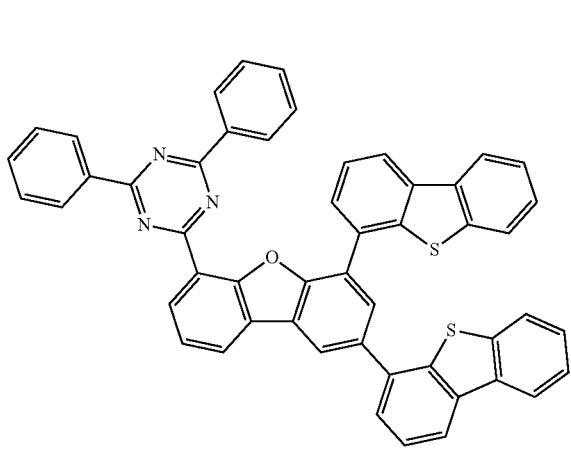
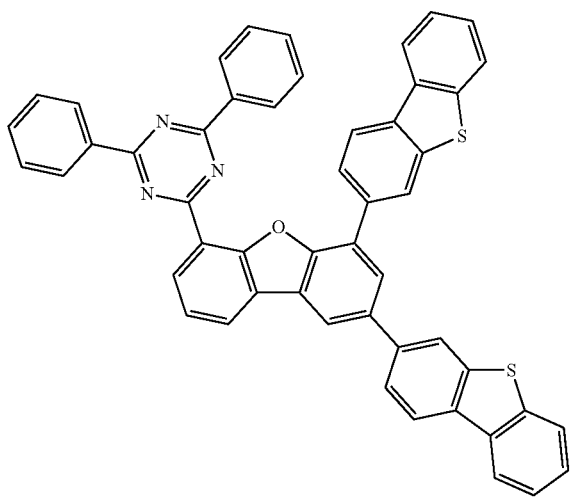
42
-continued
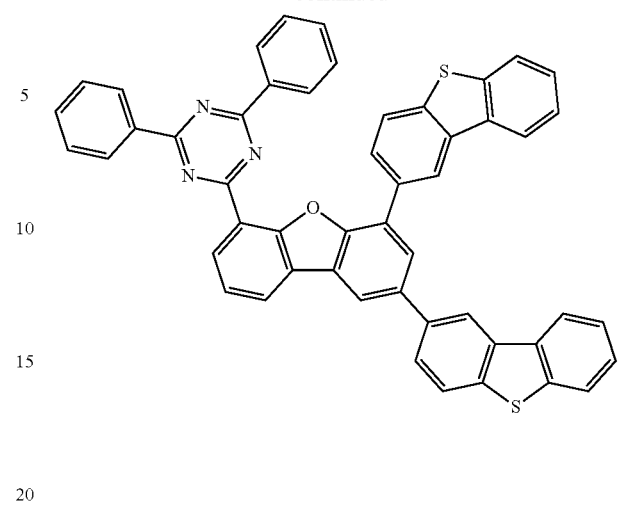
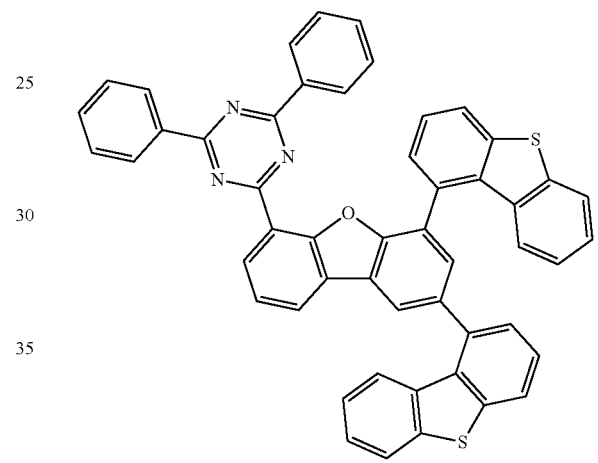
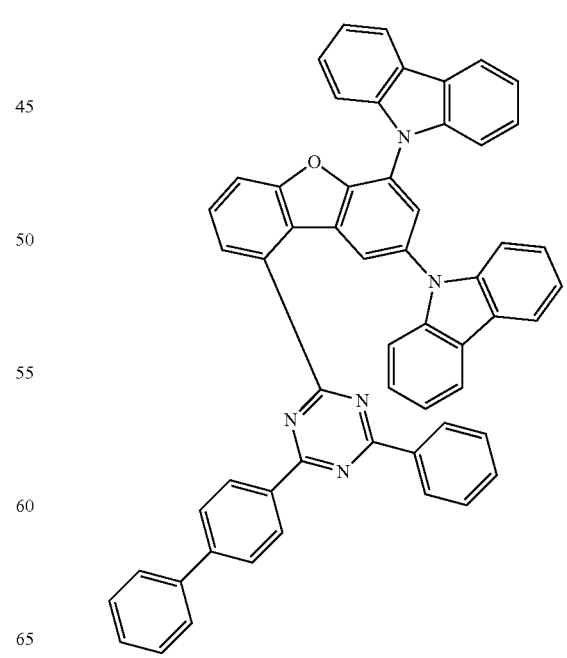

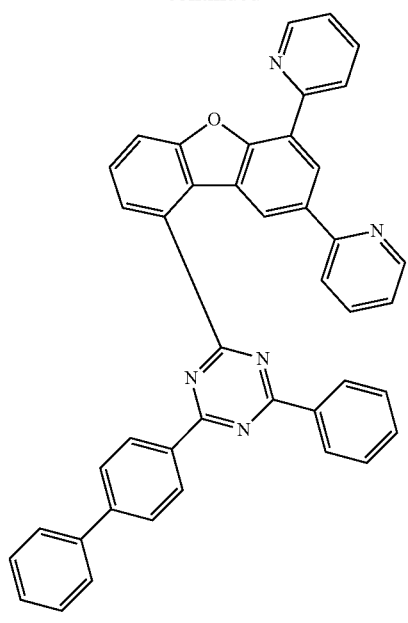
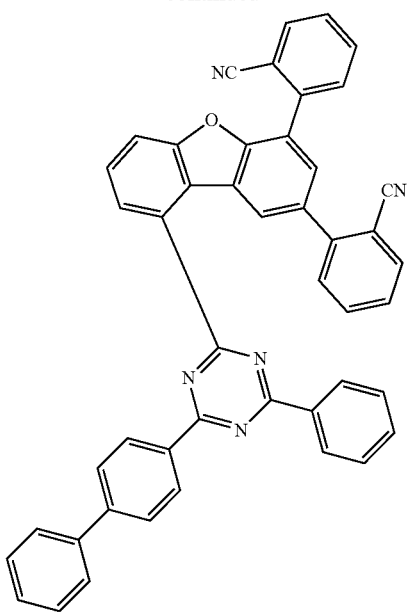
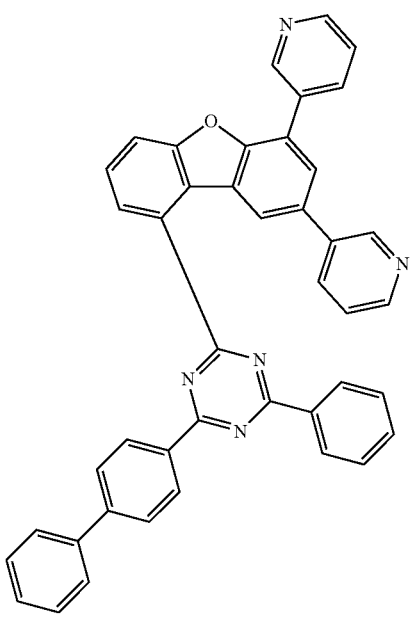
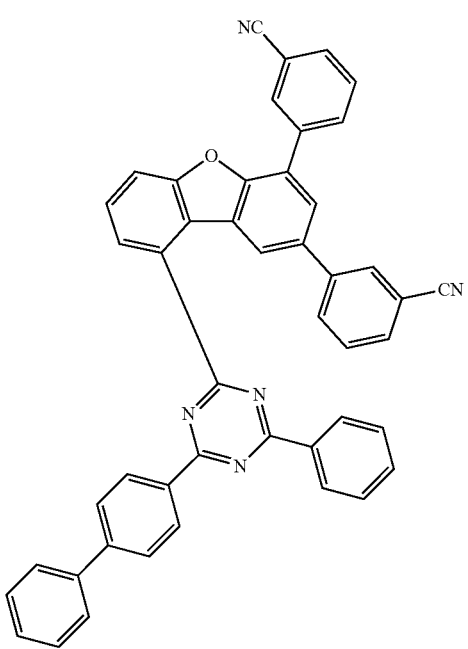

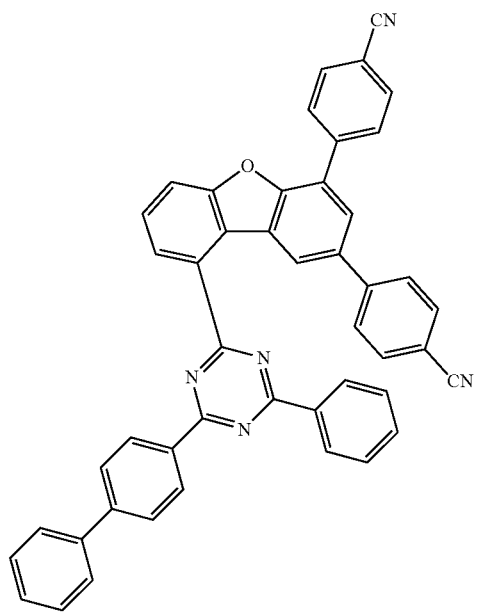
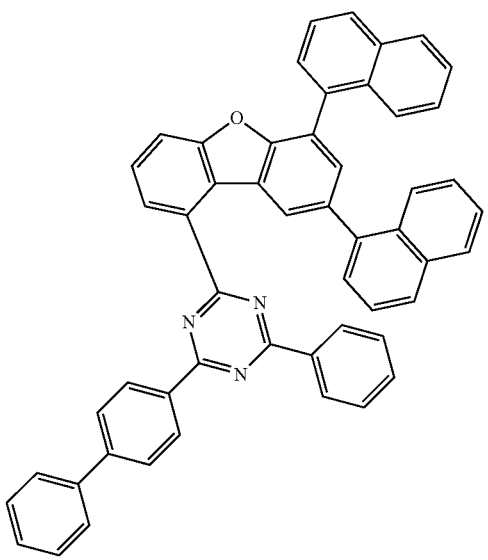
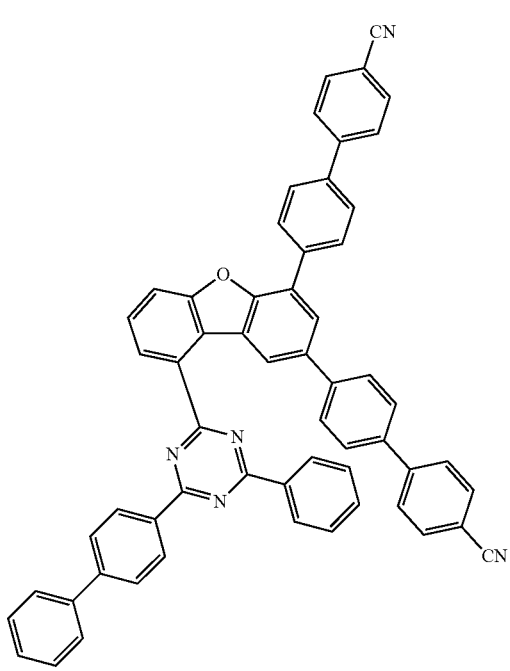
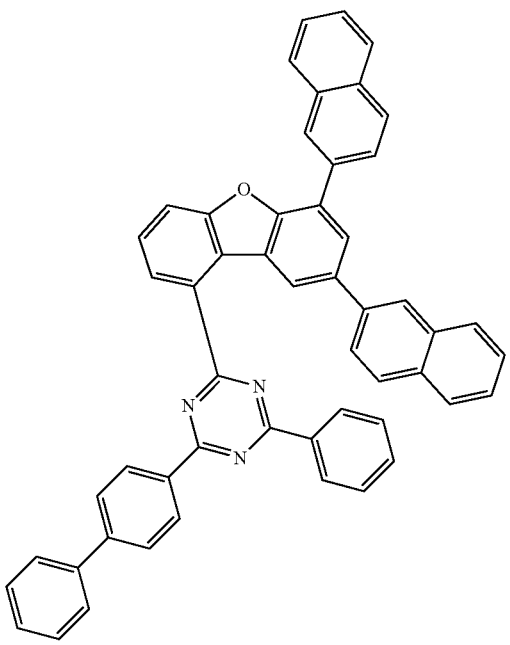

-continued
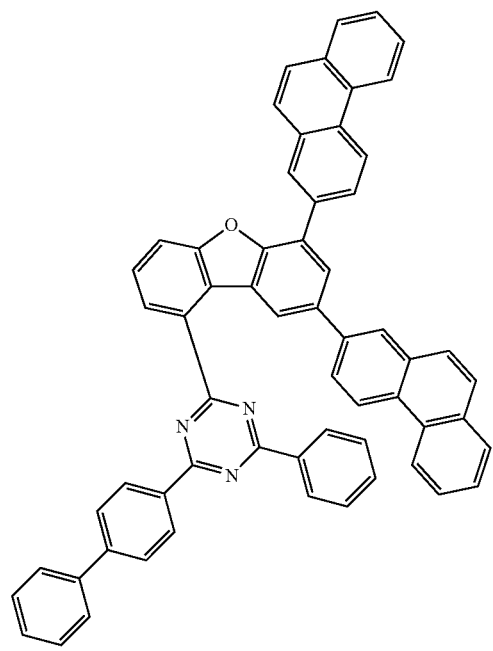
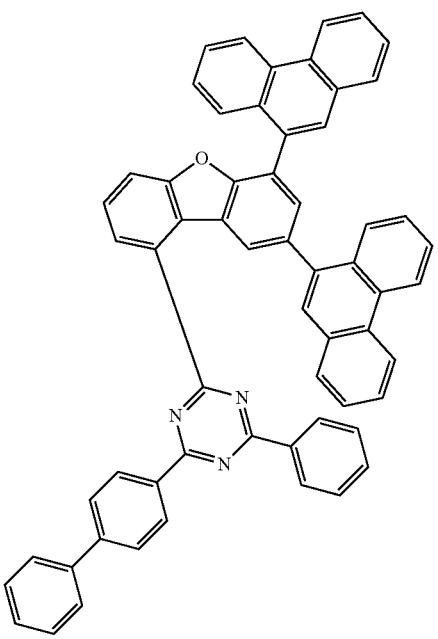
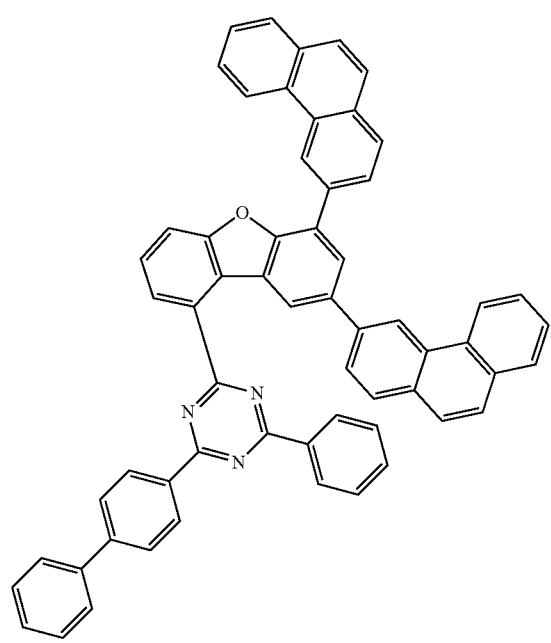
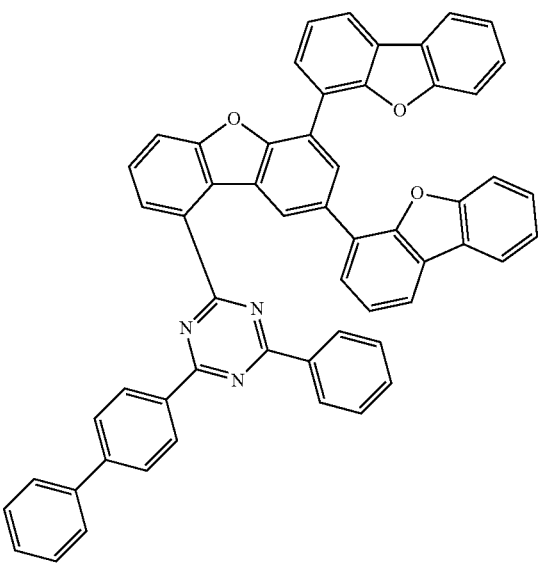

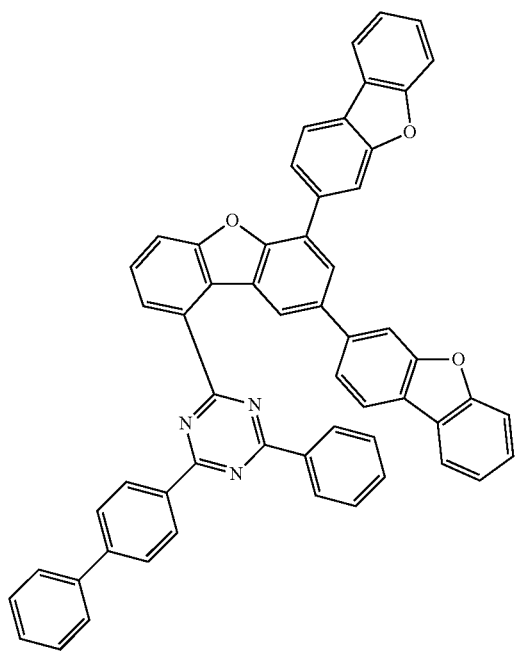
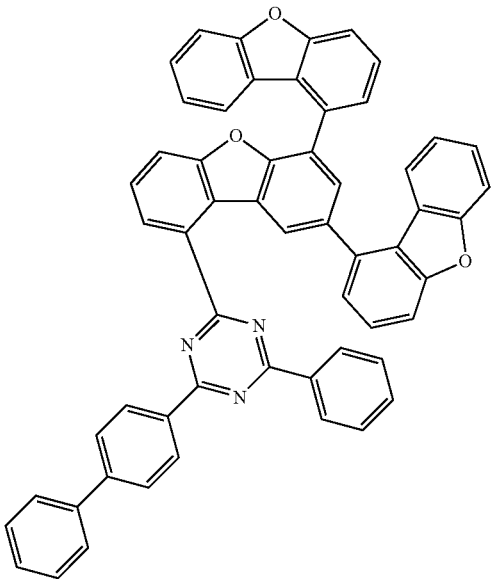
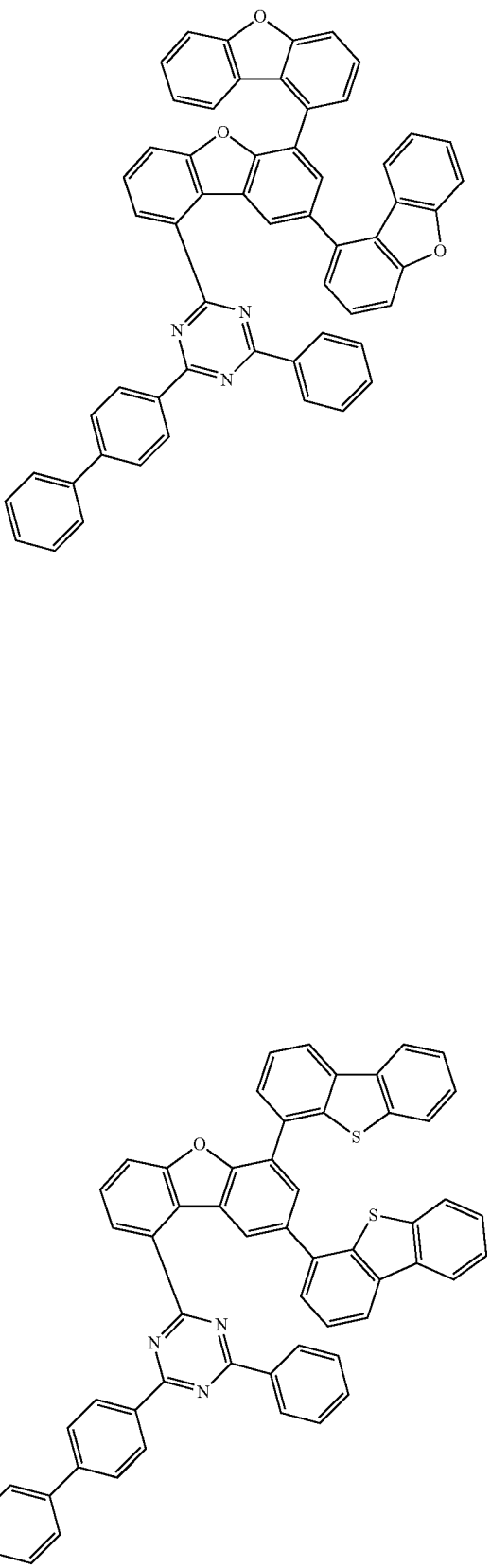

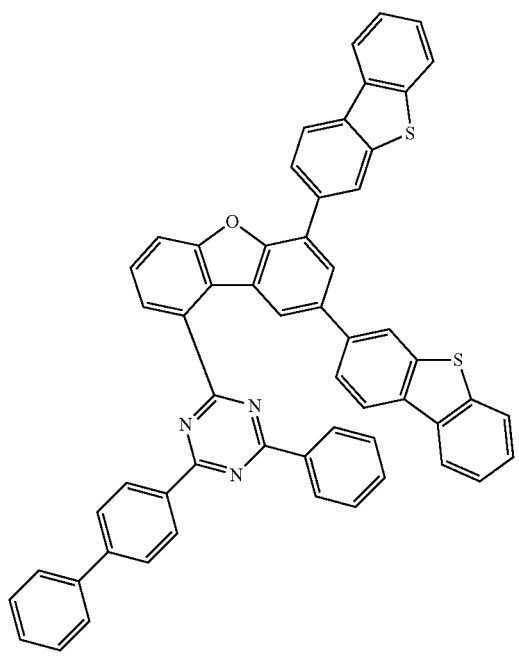
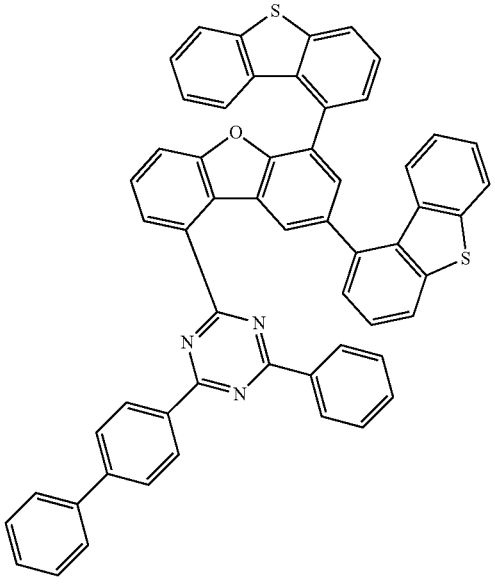
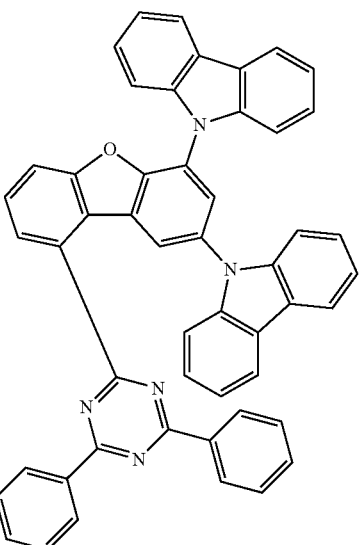
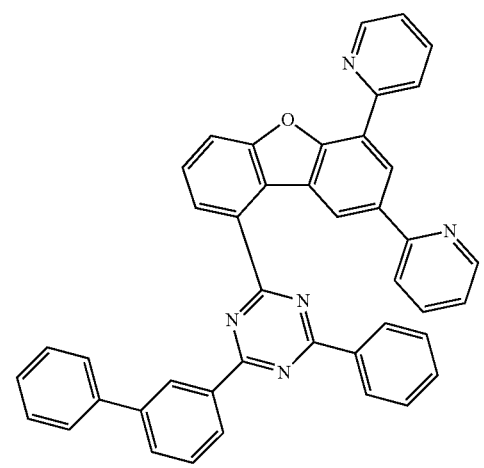

53
-continued
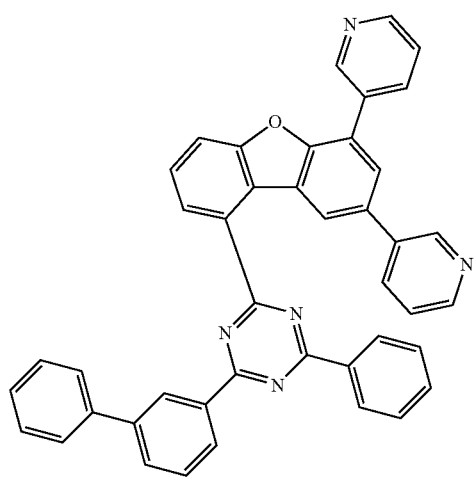
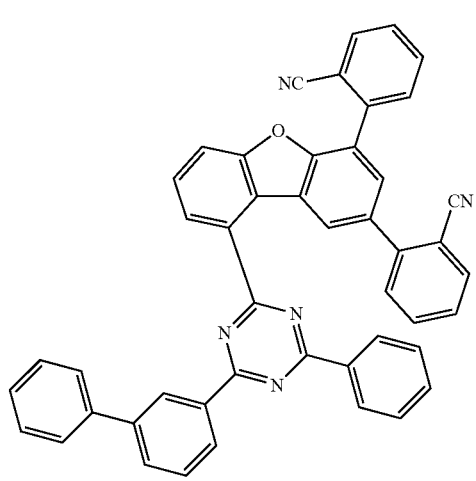
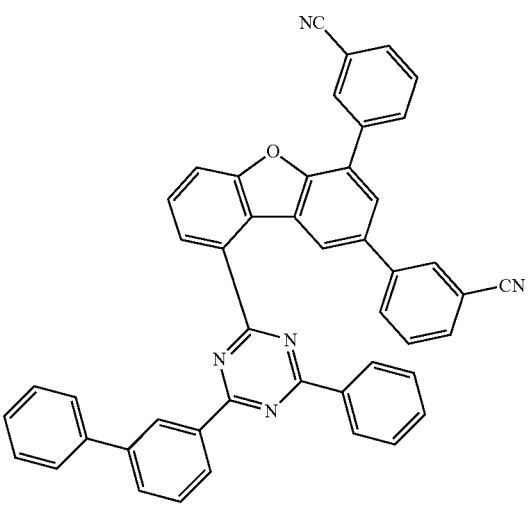
54
-continued
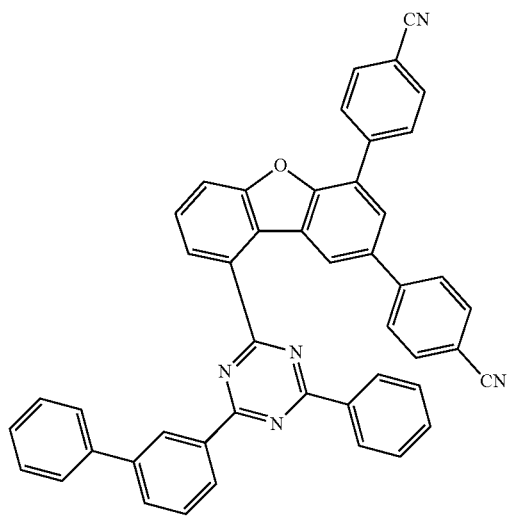
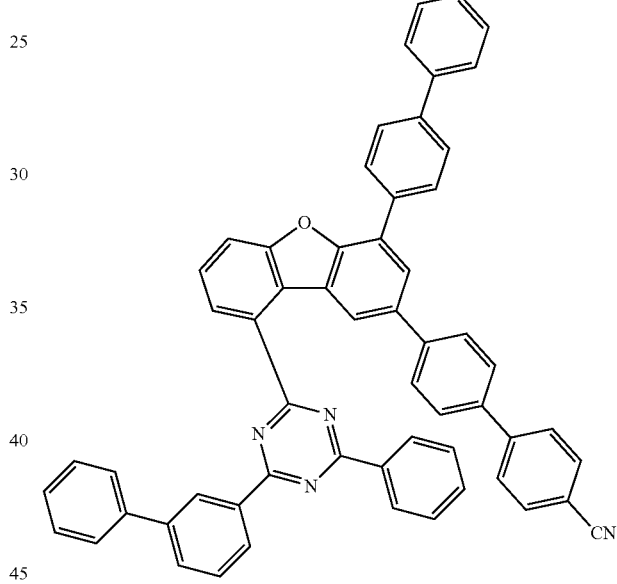
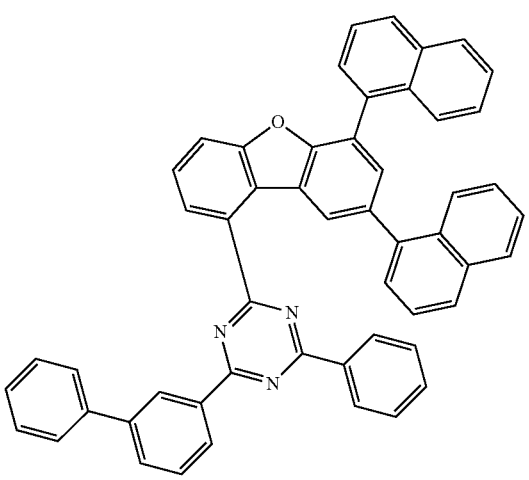

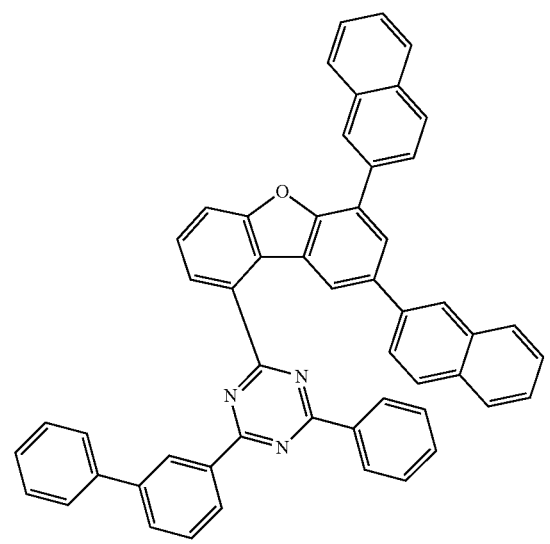
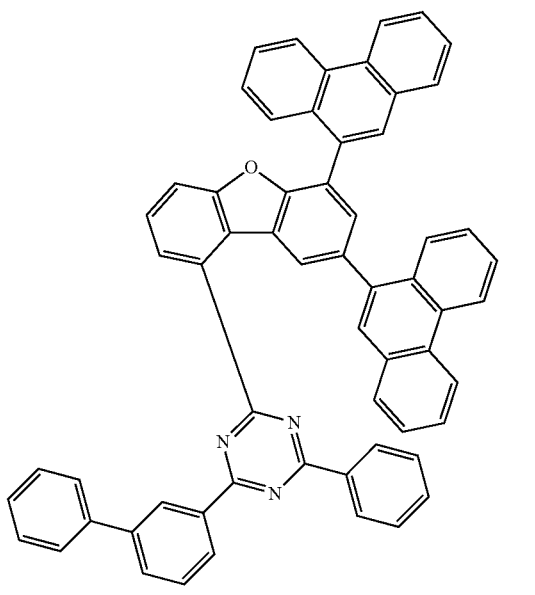
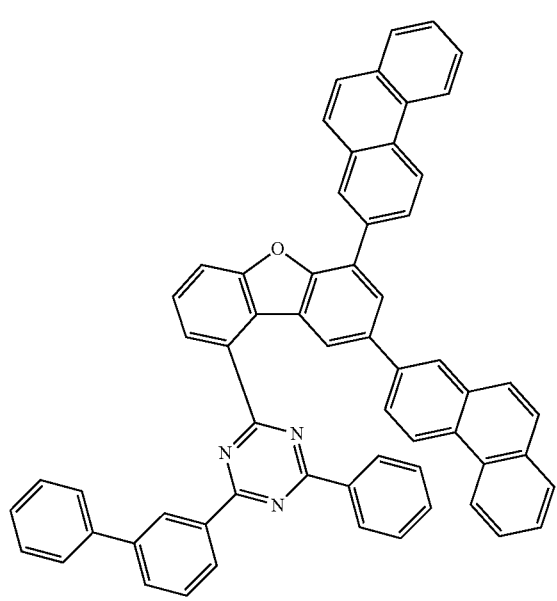
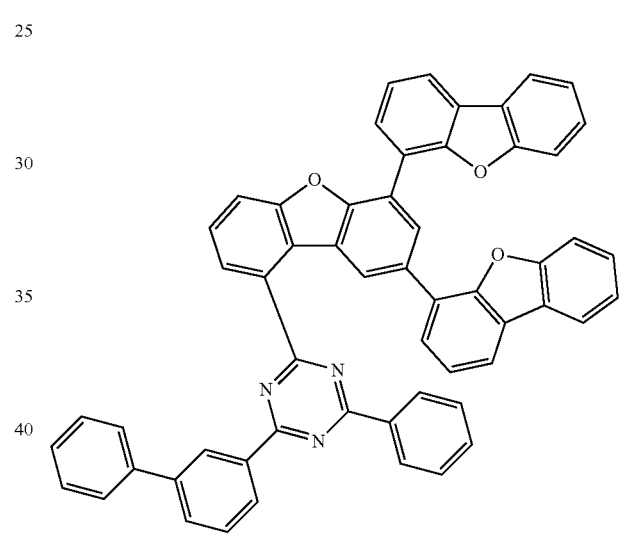
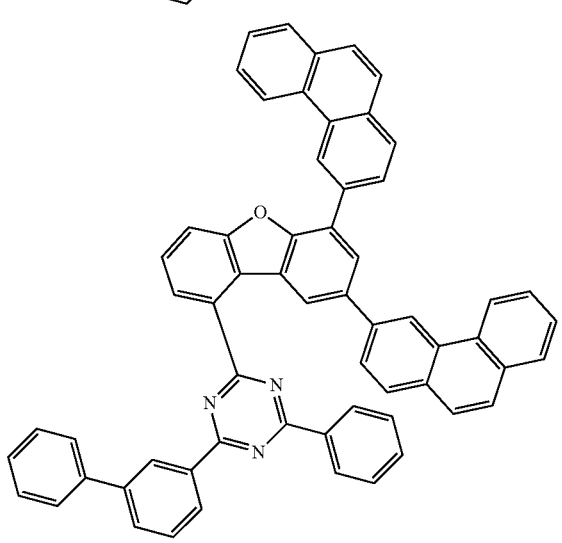
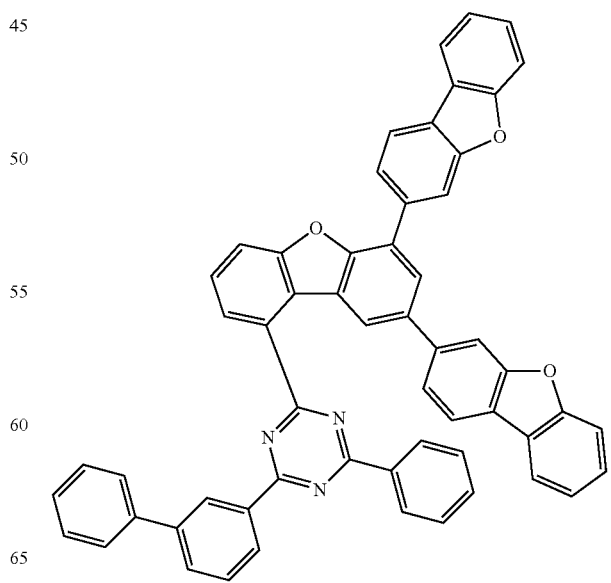

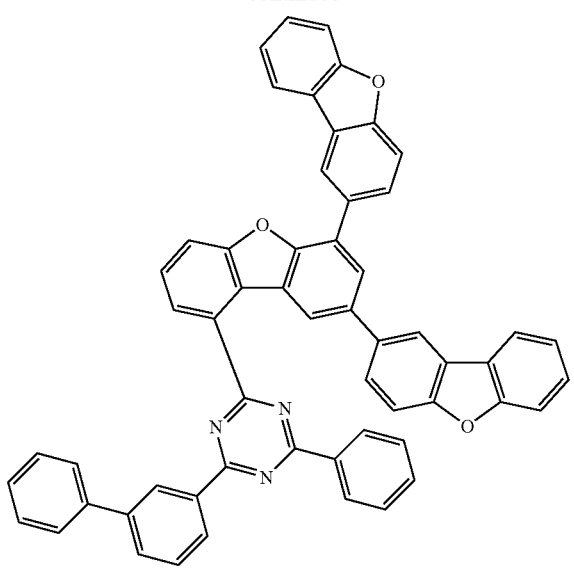
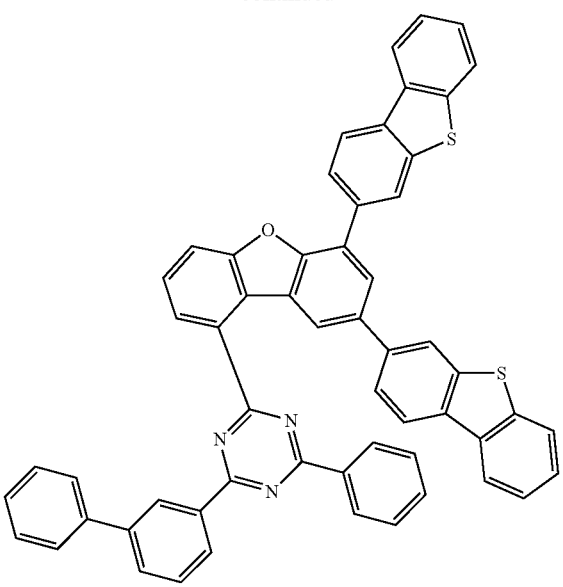
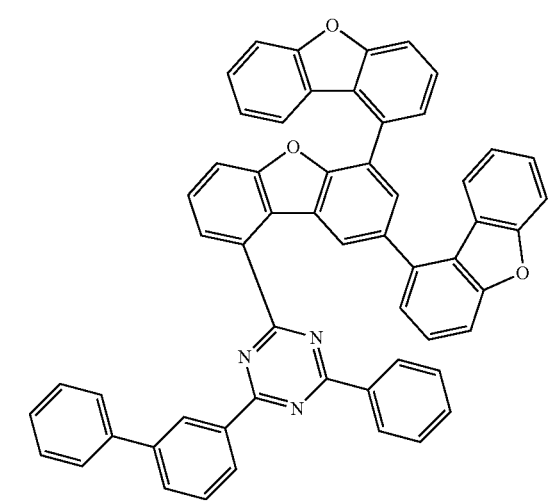
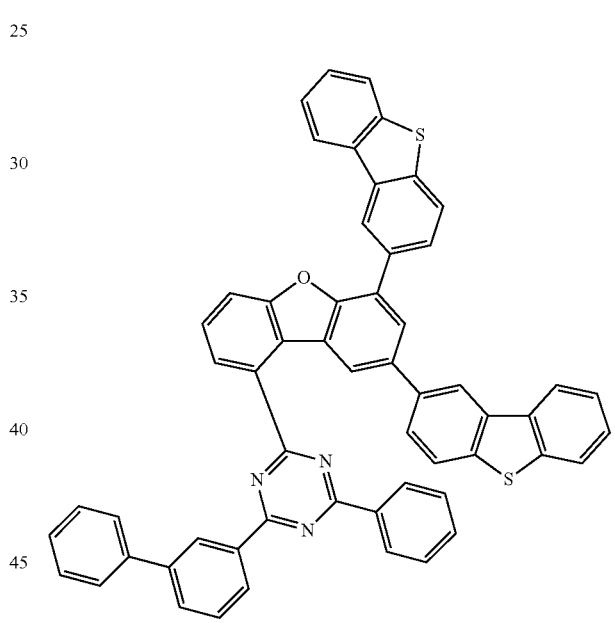
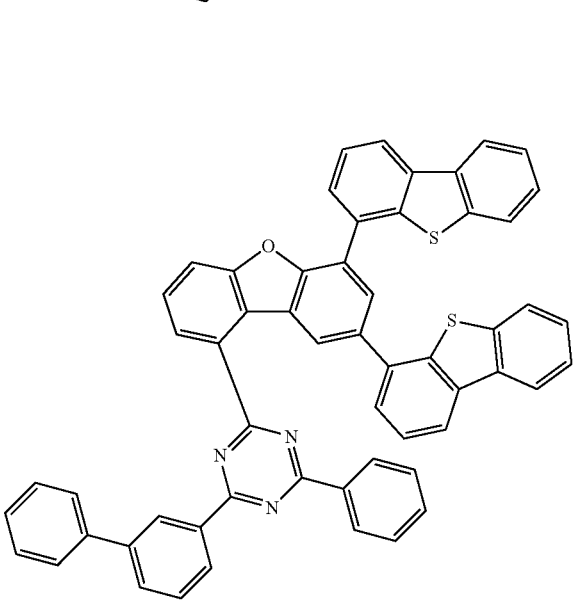
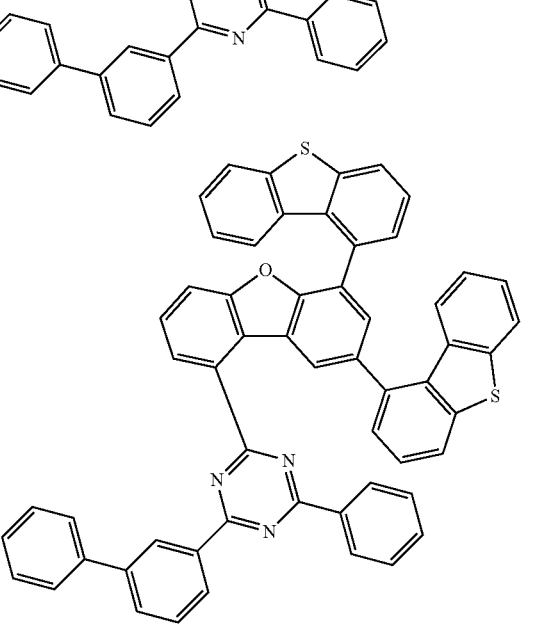

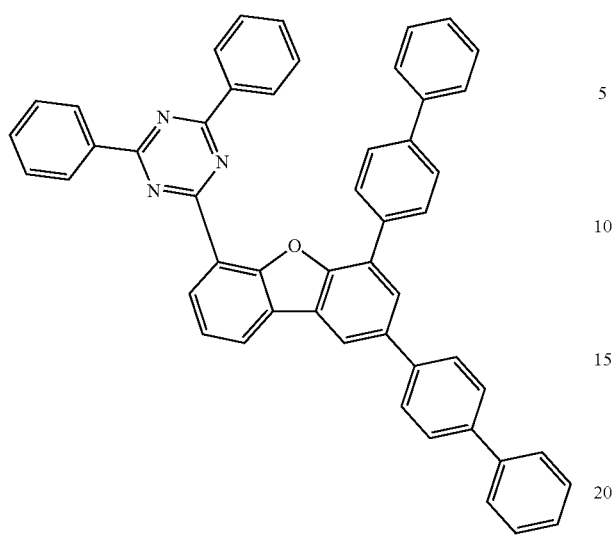
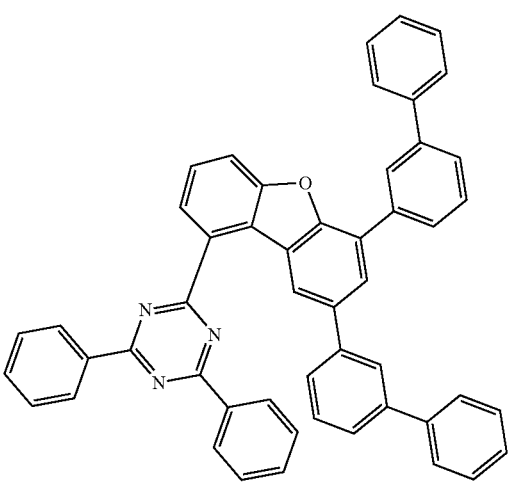
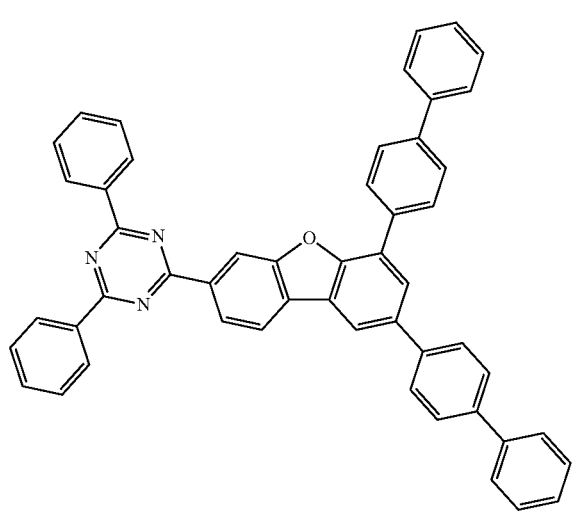
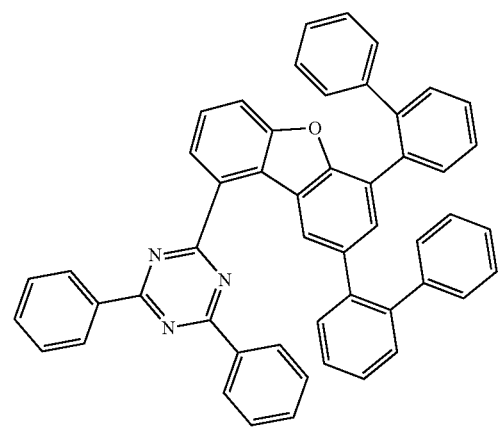
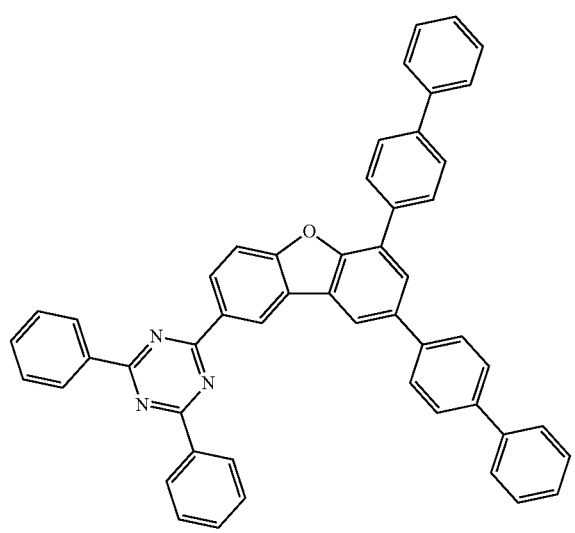
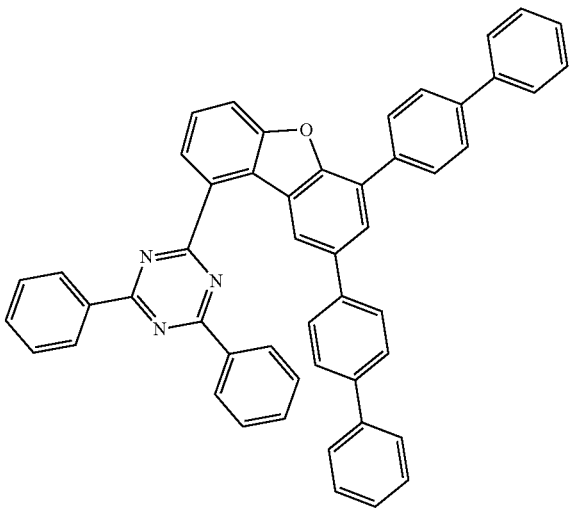

61
-continued
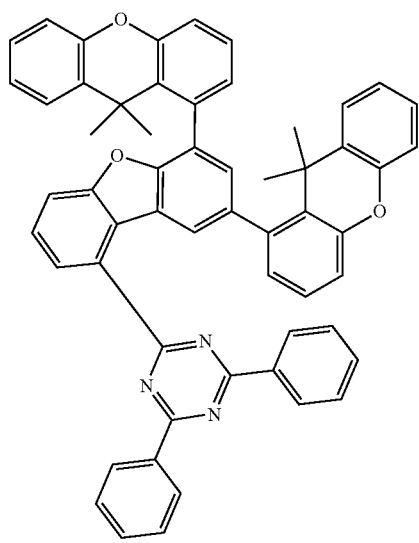
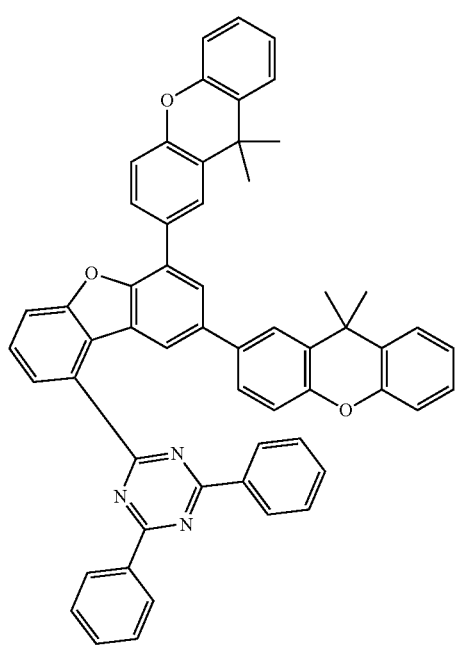
62
-continued
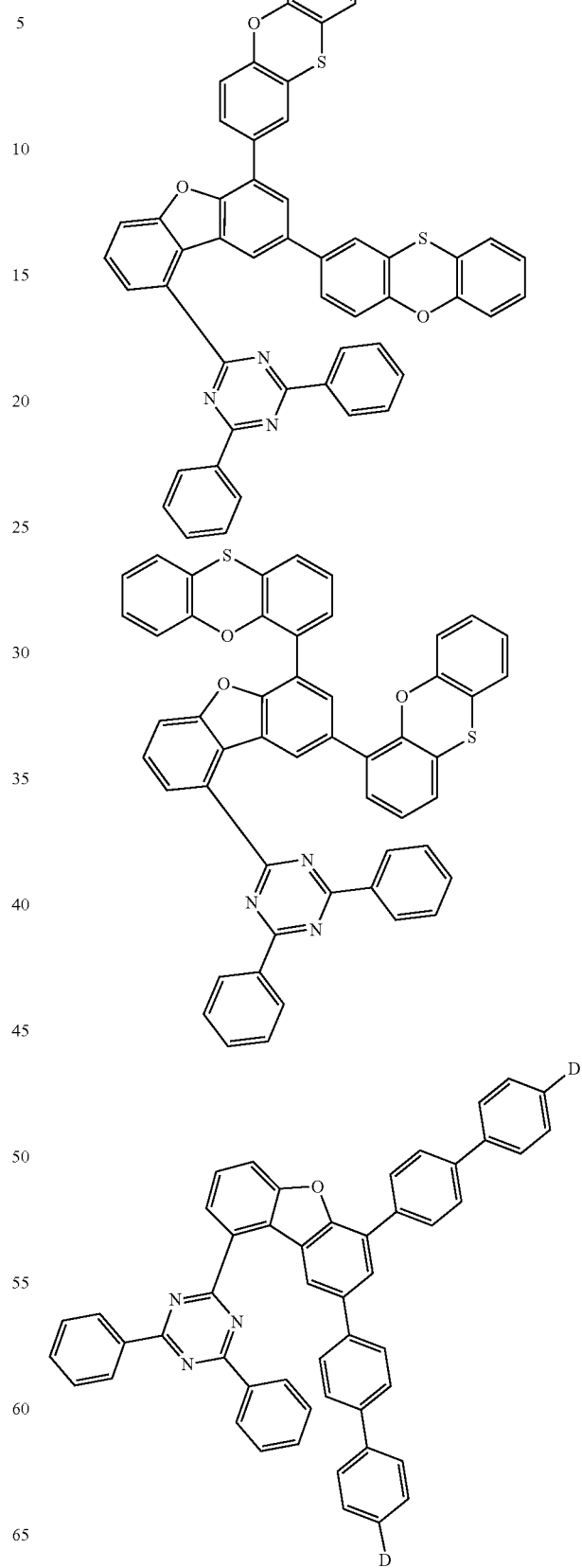

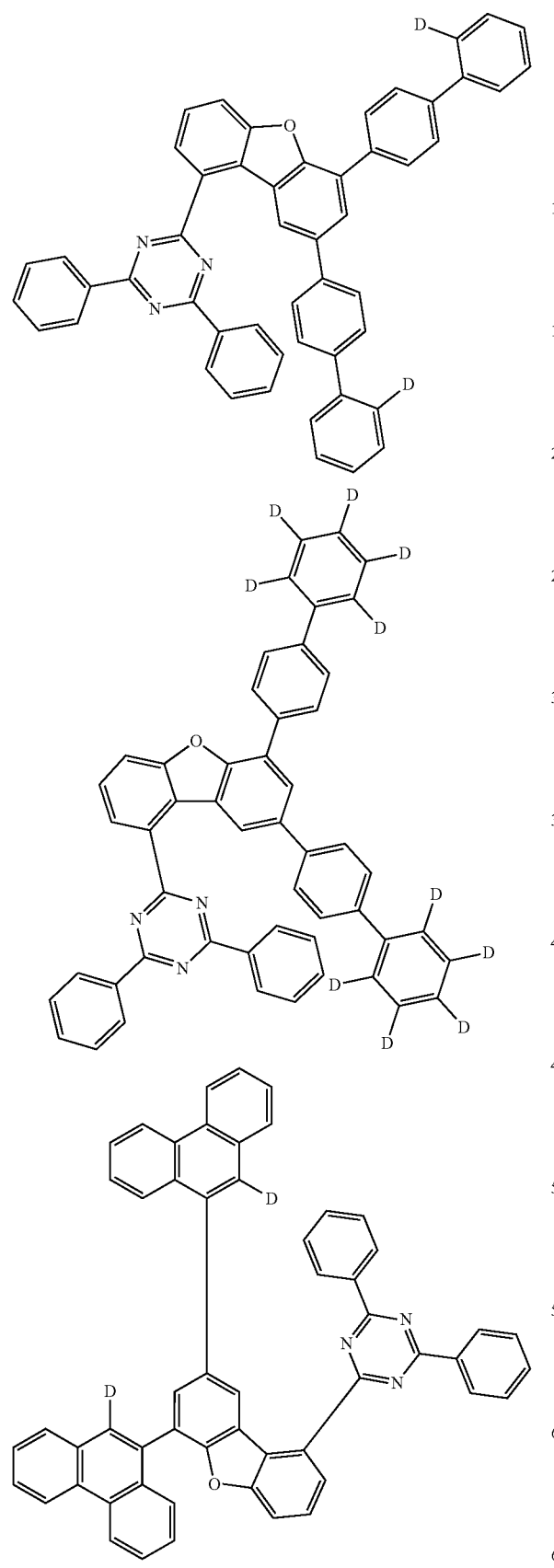
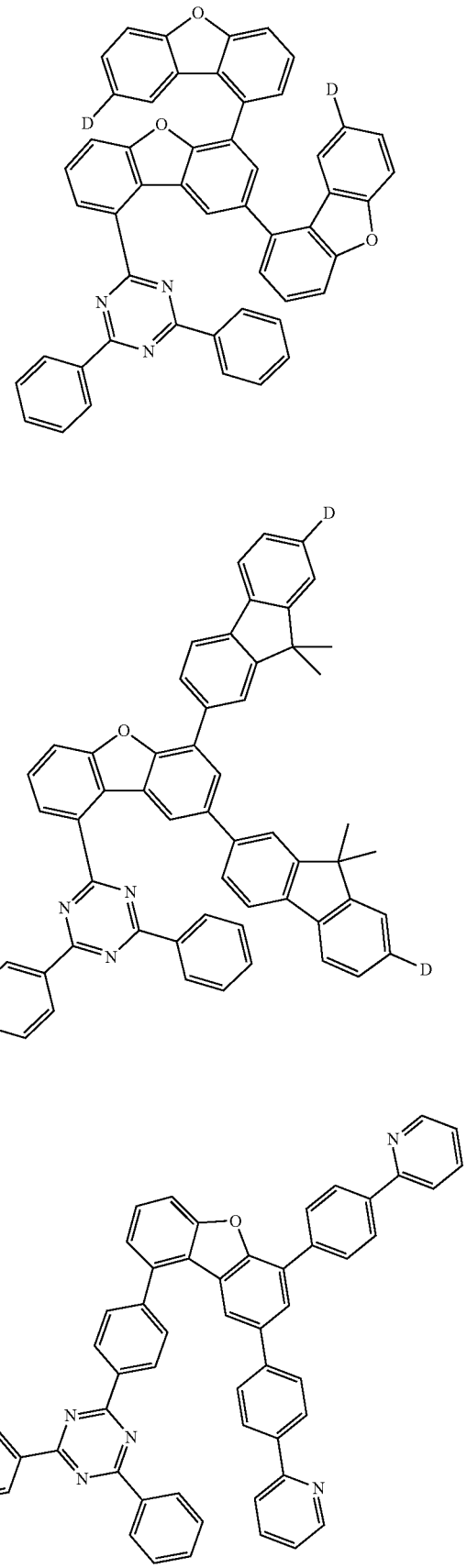

65
-continued
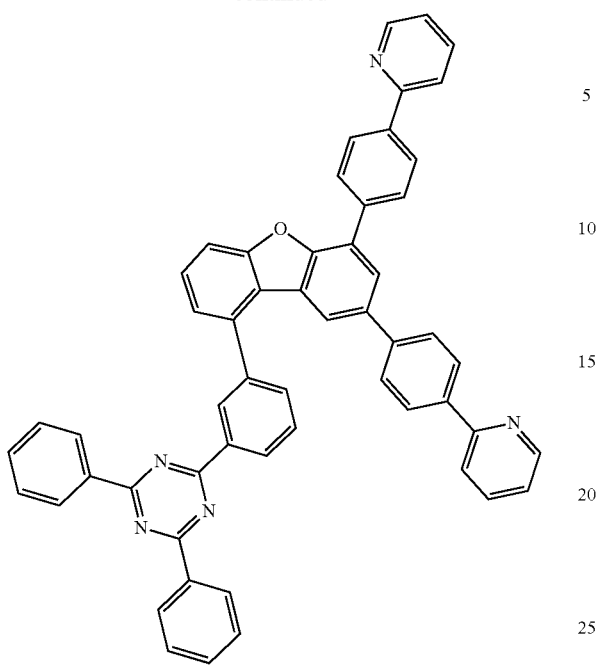
66
-continued
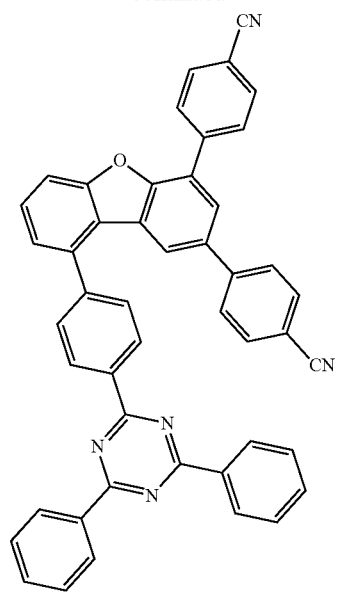
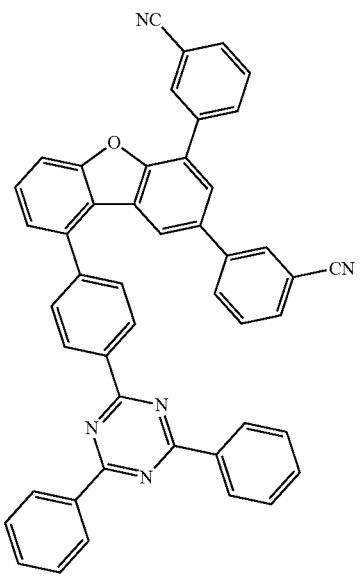
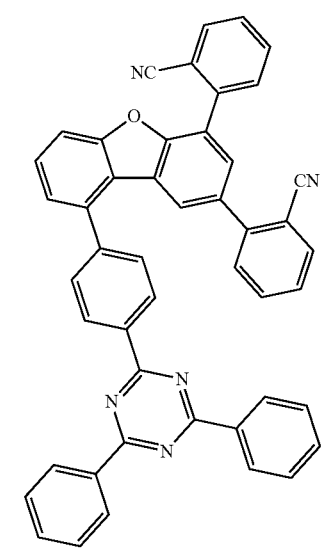

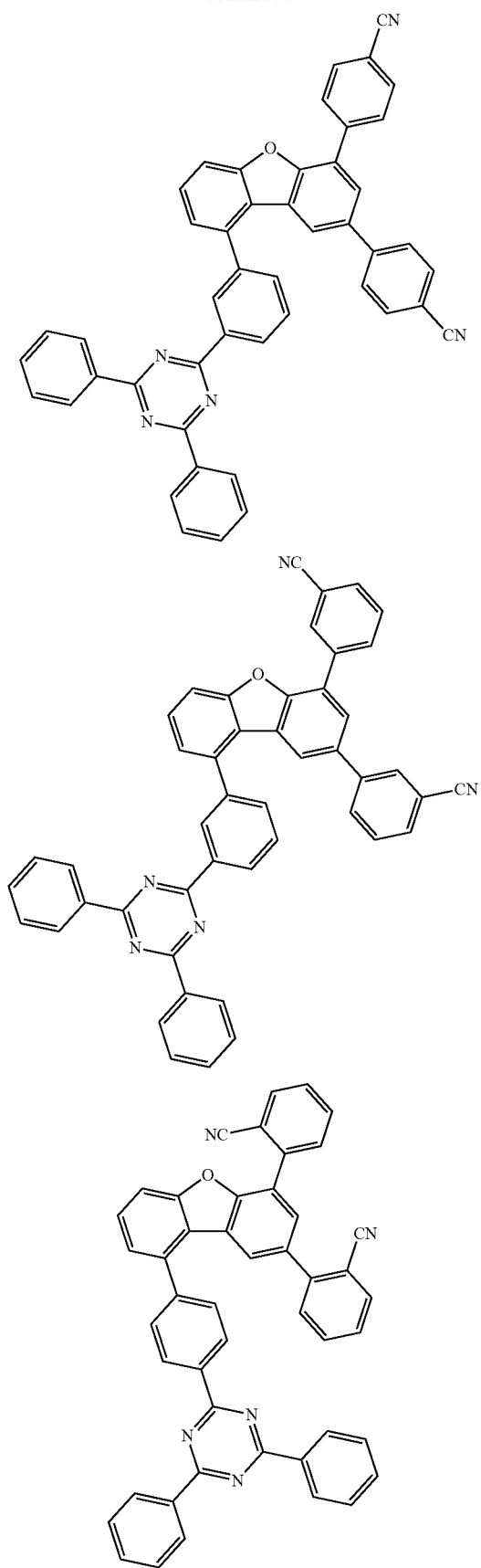
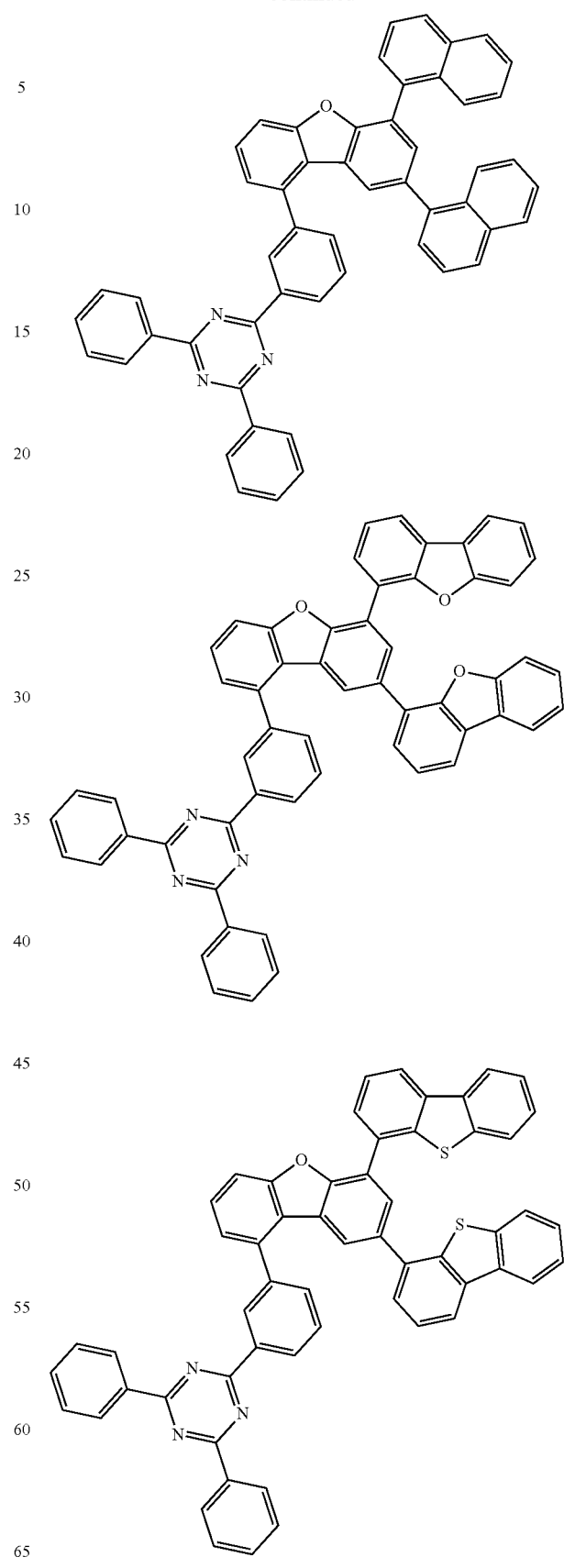

-continued

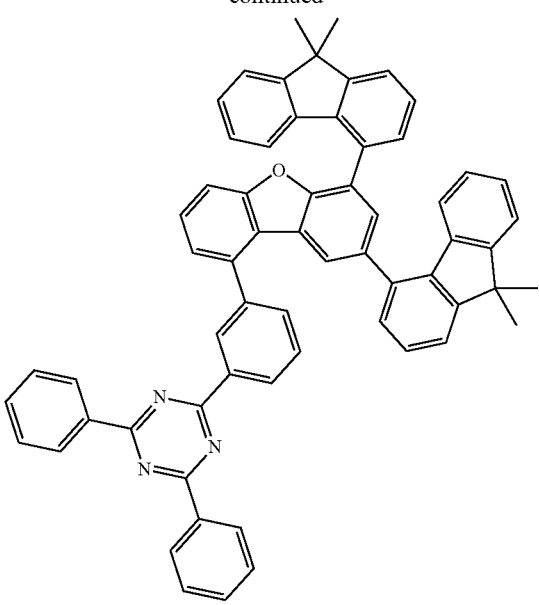

The compound represented by the Chemical Formula 1 can be prepared as shown in the following Reaction Scheme 1 or Reaction Scheme 2:

[Reaction Scheme 1]

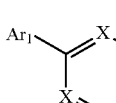

[Reaction Scheme 2]

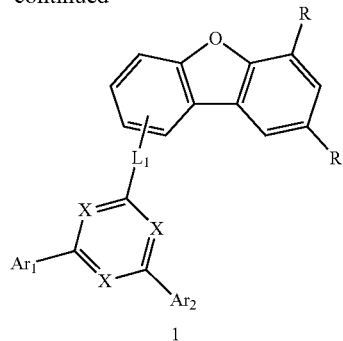

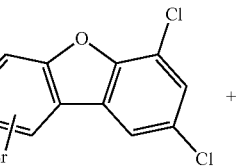

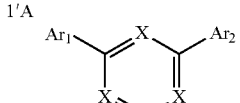

In the Reaction Schemes 1 and 2, the remaining definitions excluding X' are as defined above, and X' is a halogen, preferably Br, or Cl. Each step of Reaction Schemes 1 and 2 is a Suzuki reaction, which is well known in the art. The preparation method can be further specified in the preparation examples described later.

In addition, the present invention provides an organic light emitting device including the compound represented by the Chemical Formula 1. In one example, the present invention provides an organic light emitting device including: a first electrode; a second electrode provided to face the first electrode; and one or more organic material layers provided between the first electrode and the second electrode, wherein one or more of the organic material layers include the compound represented by the Chemical Formula 1.

The organic material layer of the organic light emitting device of the present invention may have a single layer structure, but it may have a multilayered structure in which two or more organic material layers are laminated. For example, the organic light emitting device of the present invention may have a structure including a hole injection layer, a hole transport layer, a light emitting layer, an electron transport layer, an electron injection layer, and the like as the organic material layer. However, the structure of the organic light emitting device is not limited thereto, but may include a smaller number of organic layers.

Further, the organic material layer may include a hole injection layer, a hole transport layer, or a layer simultaneously performing the hole injection and transport, and the hole injection layer, the hole transport layer, or the layer simultaneously performing the hole injection and transport include a compound represented by the Chemical Formula 1.

Further, the organic material layer may include a light emitting layer, and the light emitting layer includes the compound represented by the Chemical Formula 1.

Further, the organic material layer may include an electron transport layer or an electron injection layer, and the electron transport layer or the electron injection layer include a compound represented by the Chemical Formula 1.

Further, the electron transport layer, the electron injection layer or a layer simultaneously performing the electron transport and the electron injection include a compound represented by the Chemical Formula 1.

Further, the organic material layer may include a light emitting layer and an electron transport layer, and the electron transport layer may include the compound represented by the Chemical Formula 1.

Further, the organic light emitting device according to the present invention may be an organic light emitting device having a structure (normal type) where an anode, one or more organic material layers, and a cathode are sequentially laminated on a substrate. Further, the organic light emitting device according to the present invention may be an organic light emitting device having an inverted direction structure (inverted type) where the cathode, one or more organic material layers, and the anode are sequentially laminated on the substrate. For example, the structure of the organic light emitting device according to one embodiment of the present invention is illustrated in FIGS. 1 and 2.

FIG. 1 illustrates an example of an organic light emitting device including a substrate 1, an anode 2, a light emitting layer 3, and a cathode 4. In such a structure, the compound represented by the Chemical Formula 1 may be included in the light emitting layer.

FIG. 2 illustrates an example of an organic light emitting device including a substrate 1, an anode 2, a hole injection layer 5, a hole transport layer 6, a light emitting layer 7, an electron transport layer 8, and a cathode 4. In such a structure, the compound represented by the Chemical Formula 1 may be included in one or more layers of the hole injection layer, the hole transport layer, the light emitting layer, and the electron transport layer.

The organic light emitting device according to the present invention may be manufactured by using materials and methods known in the art, except that one or more of organic material layers include the compound represented by the Chemical Formula 1. Further, in the case where the organic light emitting device includes a plurality of organic material layers, the organic material layers may be formed of the same materials or different materials.

For example, the organic light emitting device according to the present invention may be manufactured by sequentially laminating the first electrode, the organic material layer, and the second electrode on the substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming the organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, the organic material layer, and an anode material on the substrate.

Further, the compound represented by the Chemical Formula 1 may be formed as the organic material layer by a vacuum deposition method as well as a solution coating method during the production of the organic light emitting device. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

In one example, the first electrode is the anode, and the second electrode is the cathode, and alternatively, the first electrode is the cathode, and the second electrode is the anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection material layer is a layer injecting the holes from the electrode, and the hole injection material is preferably a compound which has an ability of transporting the holes, a hole injection effect in the anode and an excellent hole injection effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer receiving the holes from the hole injection layer and transporting the holes to the light emitting layer, and the hole transport material is a material that can receive the holes from the anode or the hole injection layer and transport the holes to the light emitting layer, and a material having large mobility to the holes is suitable. Specific examples thereof include an arylamine-based organic material, a conductive polymer, a block copolymer in which a conjugate portion and a non-conjugate portion are present together, and the like, but are not limited thereto.

The light emitting material layer is a material that can receive the holes and the electrons from the hole transport layer and the electron transport layer, respectively, and bond the holes and the electrons to emit light in a visible ray region, and is preferably a material having good quantum efficiency to fluorescence or phosphorescence. Specific examples thereof include a 8-hydroxy-quinoline aluminum complex ($Alq_3$); a carbazole-based compound; a dimerized styryl compound; BAlq; a 10-hydroxybenzoquinoline-metal compound; benzoxazole, benzthiazole, and benzimidazole-based compounds; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensed aromatic cycle derivative, a heterocycle-containing compound, or the like. Specific examples of the condensed aromatic cycle derivative include an anthracene derivative, a pyrene derivative, a naphthalene derivative, a pentacene derivative, a phenanthrene compound, a fluoranthene compound, and the like, and specific examples of the heterocycle-containing compound include a carbazole derivative, a dibenzofuran derivative, a ladder-type furan compound, a pyrimidine derivative, and the like, but are not limited thereto.

Examples of the dopant material include an aromatic amine derivative, a styrylamine compound, a boron complex, a fluoranthene compound, a metal complex, and the like. Specifically, the aromatic amine derivative is a condensed aromatic cycle derivative having a substituted or unsubstituted arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport material is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front side emission type, a back side emission type, or a double side emission type according to the used material.

Further, the compound represented by the Chemical Formula 1 may be included in an organic solar cell or an organic transistor in addition to the organic light emitting device.

Hereinafter, preferred examples of the present invention will be described in order to facilitate understanding of the present invention. However, the following examples are presented for illustrative purposes only, and the scope of the present invention is not limited thereto.

[Preparation Example]
Preparation Example 1: Preparation of Intermediate 1'

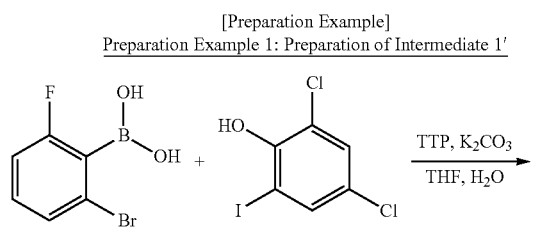

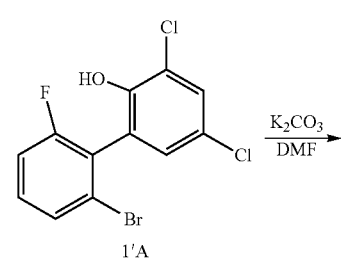

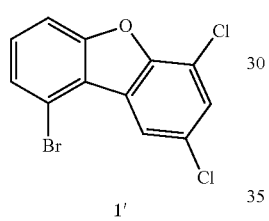

1'

Preparation Example 2: Preparation of Intermediate 2'

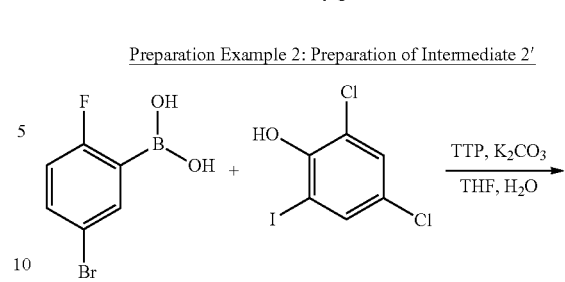

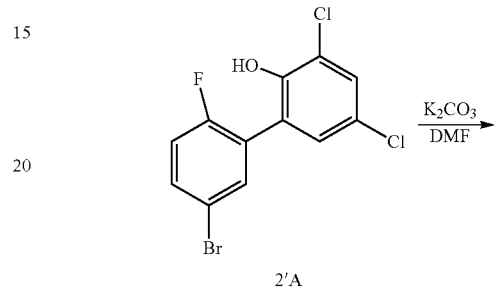

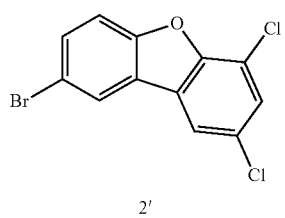

2'

1) Preparation of Compound 1'A (2-Bromo-8-fluorophenyl)boronic acid (30.0 g, 137 mmol) and 2,4-dichloro-6-iodophenol (43.6 g, 150 mmol) were dissolved to 400 ml of tetrahydrofuran under a nitrogen atmosphere, and the mixture was stirred and refluxed. Then, potassium carbonate (56.8 g, 411 mmol) was added by dissolving in 150 ml of water and thoroughly stirred. Tetrakistriphenyl-phosphinopalladium (4.8 g, 4 mmol) was then added thereto. After reaction for 12 hours, the temperature was lowered to room temperature, and the organic layer and the water layer were separated, and the organic layer was distilled under reduced pressure. The distillate was extracted with chloroform and water, and then the organic layer was dried with magnesium sulfate. The organic layer was dried, and then subjected to column chromatography with hexane and ethyl acetate to give Compound 1'A (23.5 g, 51%).

2) Preparation of Compound 1'

Compound 1'A (23.5 g, 70 mmol) was added to 200 ml of dimethylformamide under a nitrogen atmosphere and stirred. Potassium carbonate (19.3 g, 140 mmol) was then added and refluxed. After 2 hours, the traction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Compound 1'(18 g, 81%).

1) Preparation of Compound 2'A (5-Bromo-2-fluorophenyl)boronic acid (30.0 g, 137 mmol) and 2,4-dichloro-6-iodophenol (43.6 g, 150 mmol) were added to 400 ml of tetrahydrofuran under a nitrogen atmosphere, and the mixture was stirred and refluxed. Then, potassium carbonate (56.8 g, 411 mmol) was added by dissolving in 150 ml of water and thoroughly stirred. Tetrakistriphenyl-phosphinopalladium (4.8 g, 4 mmol) was then added thereto. After reaction for 12 hours, the temperature was lowered to room temperature, and the organic layer and the water layer were separated, and the organic layer was distilled under reduced pressure. The distillate was extracted with chloroform and water, and then the organic layer was dried with magnesium sulfate. The organic layer was dried, and then subjected to column chromatography with hexane and ethyl acetate to give Compound 2'A (27.6 g, 60%).

2) Preparation of Compound 2'

Compound 2'A (27.6 g, 82 mmol) was added to 200 ml of dimethylformamide under a nitrogen atmosphere and stirred. Potassium carbonate (22.7 g, 164 mmol) was then added and refluxed. After 2 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Compound 2'(23 g, 90%).

Preparation Example 3: Preparation of Intermediate 3'

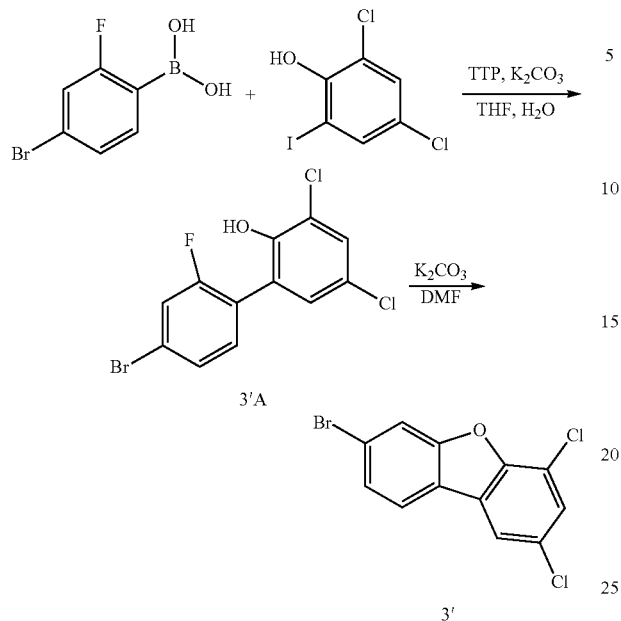

1) Preparation of Compound 3'A (4-Bromo-2-fluorophenyl)boronic acid (30.0 g, 137 mmol) and 2,4-dichloro-6-iodophenol (43.8 g, 150 mmol) were dissolved to 400 ml of tetrahydrofuran under a nitrogen atmosphere, and the mixture was stirred and refluxed. Then, potassium carbonate (58.8 g, 411 mmol) was added by dissolving in 150 ml of water and thoroughly stirred. Tetrakistriphenyl-phosphinopalladium (4.8 g, 4 mmol) was then added thereto. After reaction for 12 hours, the temperature was lowered to room temperature, and the organic layer and the water layer were separated, and the organic layer was distilled under reduced pressure. The distillate was extracted with chloroform and water, and then the organic layer was dried with magnesium sulfate. The organic layer was dried, and then subjected to column chromatography with hexane and ethyl acetate to give Compound 3'A (32.7 g, 71%).

2) Preparation of Compound 3'

Compound 3'A (32.7 g, 97 mmol) was added to 200 ml of dimethylformamide under a nitrogen atmosphere and stirred. Potassium carbonate (28.9 g, 194 mmol) was then added and refluxed. After 2 hours, the reaction solution was cooled to room temperature and filtered. The filtrate was extracted with chloroform and wafer, and then the organic layer was dried with magnesium sulfate. The organic layer was then distilled under reduced pressure and recrystallized using ethyl acetate. The resulting solid was filtered and then dried to give Compound 3'(24 g, 77%).

Preparation Example 4: Preparation of Intermediate 4'

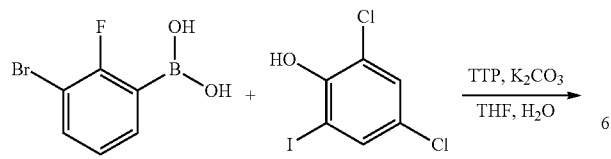

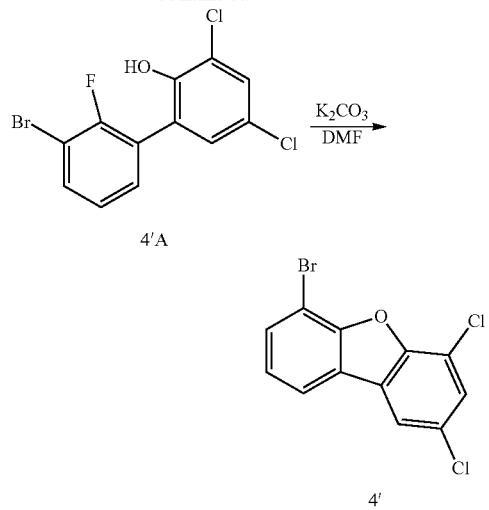

1) Preparation of Compound 4'A (3'-Bromo-2-fluorophenyl)boronic acid (30.0 g, 137 mmol) and 2,4-dichloro-6-iodophenol (43.6 g, 150 mmol) were added to 400 ml of tetrahydrofuran under a nitrogen atmosphere, and the mixture was stirred and refluxed. Then, potassium carbonate (56.8 g, 411 mmol) was added by dissolving in 150 ml of water and thoroughly stirred. Tetrakistriphenyl-phosphinopalladium (4.8 g, 4 mmol) was then added thereto. After reaction for 12 hours, the temperature was lowered to room temperature, and the organic layer and the water layer were separated, and the organic layer was distilled under reduced pressure. The distillate was extracted with chloroform and water, and then the organic layer was dried with magnesium sulfate. The organic layer was dried, and then subjected to column chromatography with hexane and ethyl acetate to give Compound 4'A (36.9 g, 80%).

2) Preparation of Compound 4'

Compound 4'A (36.9 g, 110 mmol) was added to 200 ml of dimethylformamide under a nitrogen atmosphere and stirred. Potassium carbonate (30.4 g, 220 mmol) was then added and refluxed. After 2 hours, the reaction solution was cooled to room temperature and filtered. The filtrate was extracted with chloroform and wafer, and then the organic layer was dried with magnesium sulfate. The organic layer was then distilled under reduced pressure and recrystallized using ethyl acetate. The resulting solid was filtered and then dried to give Compound 4'(25 g, 71%).

[Example]
Example 1

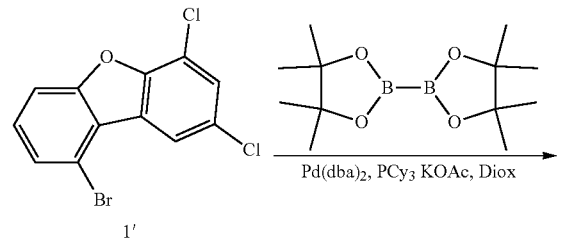

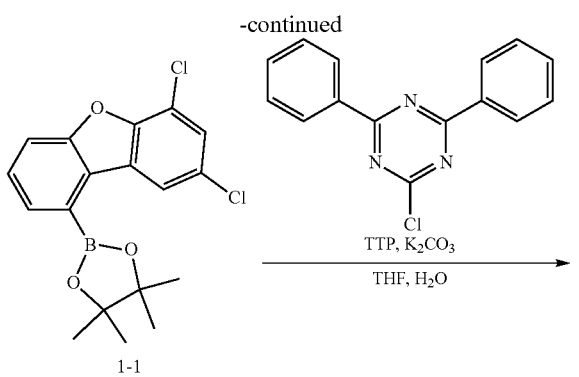

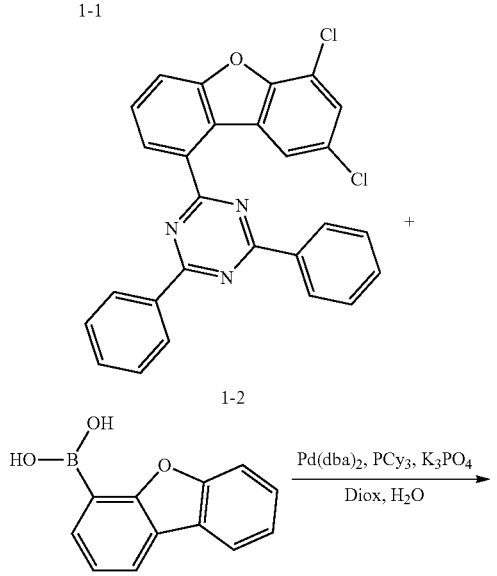

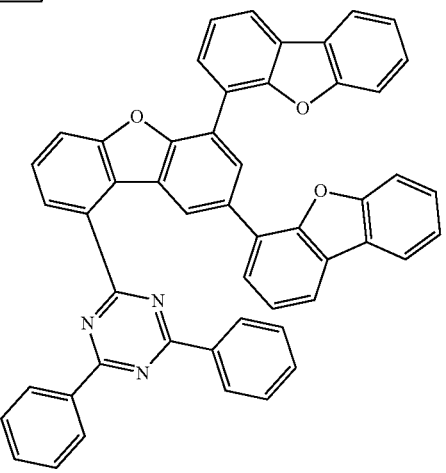

1) Preparation of Compound 1-1

Intermediate 1' (15.0 g, 48 mmol) and potassium acetate (14 g: 142 mmol) were mixed under a nitrogen atmosphere, and the mixture was added to 150 ml of dioxane and heated with stirring. Bis(dibenzylideneacetone)palladium (0.8 g, 1.4 mmol) and tricyclohexylphosphine (0.8 g, 2.8 mmol) were added under reflux, and heated and stirred for 3 hours. After completion of the reaction, the reaction solution was cooled to room temperature and then filtered. Water was added to the filtrate, extracted with chloroform, and the organic layer was dried over anhydrous magnesium sulfate.

The resulting material was distilled under reduced pressure and then recrystallized from ethanol to give Compound 1-1 (15.7 g, 91%).

2) Preparation of Compound 1-2

Intermediate 1-1 (15.7 g, 50 mmol) and 2-chloro-4,5-diphenyl-1,3,5-triazine (14.6 g, 55 mmol) were added to 200 ml of tetrahydrofuran under a nitrogen atmosphere, and the mixture was stirred and refluxed. Then, potassium carbonate (20.6 g, 149 mmol) was added by dissolving in 60 ml of water and thoroughly stirred. Tetrakistriphenyl-phosphinopalladium (1.7 g, 1.5 mmol) was then added thereto. After reaction for 18 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Compound 1-2 (17.9 g, 77%). 2-Chloro-4,6-diphenyl-1,3,5-triazine was purchased from Alpha.

3) Preparation of Example 1

Intermediate 1-2 (10.0 g, 21 mmol) and dibenzo[b,d]furan-4-ylboronic acid (10.0 g, 47 mmol) were added to 200 ml of tetrahydrofuran under a nitrogen atmosphere, and the mixture was stirred and refluxed. Then, potassium phosphate (27.2 g, 128 mmol) was added by dissolving in 60 ml of water and thoroughly stirred. Bis(dibenzylideneacetone)palladium (0.7 g, 1.3 mmol) and tricyclohexylphosphine (0.7 g, 2.6 mmol) were then added thereto. After reaction for 24 hours, the reaction solution was cooled to room temperature and filtered. The filtrate was extracted with chloroform and wafer, and then the organic layer was dried with magnesium sulfate. The organic layer was then distilled under reduced pressure and recrystallized using ethyl acetate. The resulting solid was filtered and then dried to give Example 1 (7 g, 45%).

MS: $[M+H]^+ = 731$

Example 2

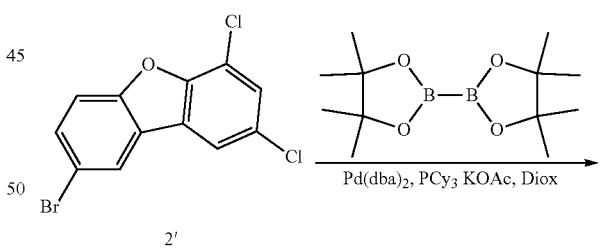

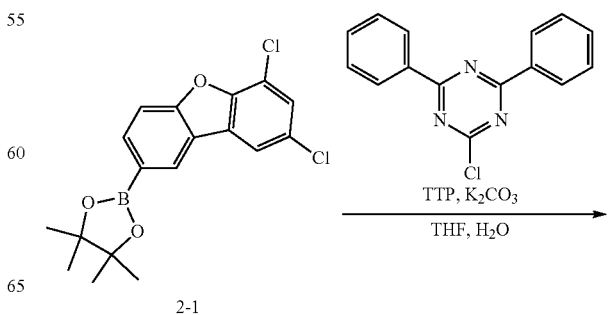

-continued

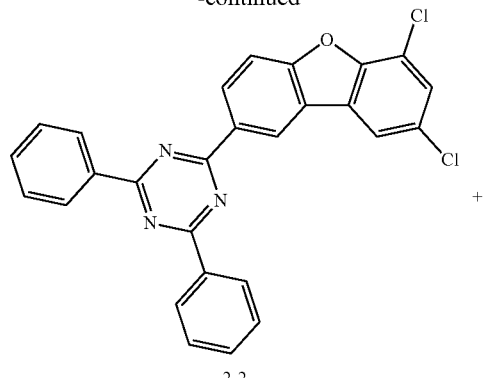

2-2

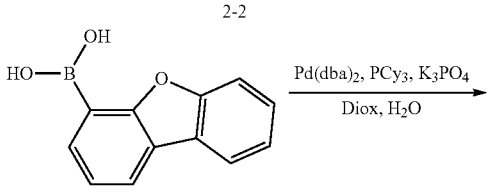

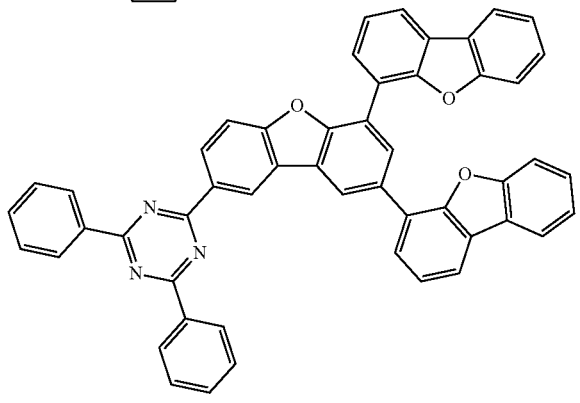

2

1) Preparation of Compound 2-1

Intermediate 2' (15.0 g, 48 mmol) and potassium acetate (14 g, 142 mmol) were mixed under a nitrogen atmosphere, and the mixture was added to 150 ml of dioxane and heated with stirring. Bis(dibenzylideneacetone)palladium (0.8 g, 1.4 mmol) and tricyclohexylphosphine (0.8 g, 2.8 mmol) were added under reflux, and heated and stirred for 3 hours. After completion of the reaction, the reaction solution was cooled to room temperature and then filtered. Water was added to the filtrate, extracted with chloroform, and the organic layer was dried over anhydrous magnesium sulfate. The resulting material was distilled under reduced pressure and then recrystallized from ethanol to obtain Compound 2-1 (15.7 g, 91%).

2) Preparation of Compound 2-2

Intermediate 2-1 (14.0 g, 44 mmol) and 2-chloro-4,6-diphenyl-1,3,5-triazine (13 g, 48 mmol) were added to 100 ml of tetrahydrofuran under a nitrogen atmosphere, and the mixture was stirred and refluxed. Then, potassium carbonate (18.4 g, 132 mmol) was added by dissolving in 50 ml of water and thoroughly stirred. Tetrakistriphenyl-phosphinopalladium (1.5 g, 1.3 mmol) was then added thereto. After reaction for 18 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Compound 2-2 (16.8 g, 81%). 2-Chloro-4,8-diphenyl-1,3,5-triazine was purchased from Alpha.

3) Preparation of Example 2

Intermediate 2-2 (10.0 g, 21 mmol) and dibenzo[b,d]furan-4-ylboronic acid (10.0 g, 47 mmol) were dissolved in 200 ml of tetrahydrofuran under a nitrogen atmosphere, and the mixture was stirred and refluxed. Then, potassium phosphate (27.2 g, 128 mmol) was added by dissolving in 60 ml of water and thoroughly stirred. Bis(dibenzylideneacetone)palladium (0.7 g, 1.3 mmol) and tricyclohexylphosphine (0.7 g, 2.6 mmol) were then added thereto. After reaction for 24 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Example 2 (9.5 g, 61%).

MS: $[M+H]^+=731$

Example 3

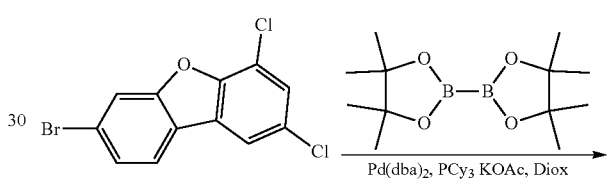

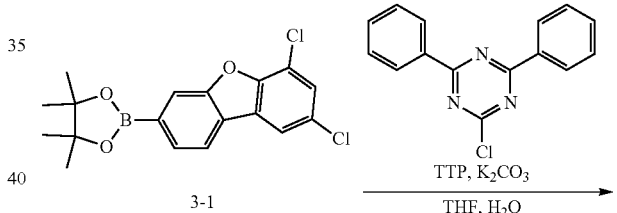

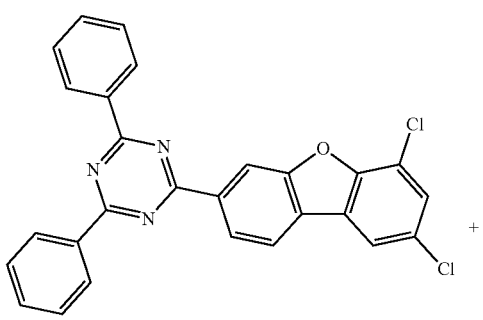

3-2

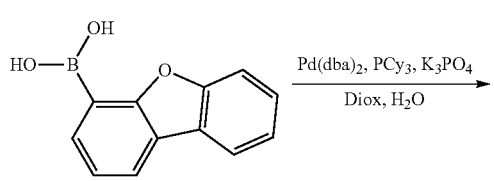

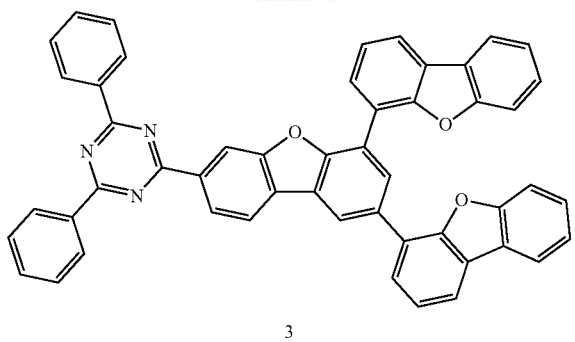

3

1) Preparation of Compound 3-1

Intermediate 3' (15.0 g, 48 mmol) and potassium acetate (14 g, 142 mmol) were mixed under a nitrogen atmosphere, and the mixture was added to 150 ml of dioxane and heated with stirring. Bis(dibenzylideneacetone)palladium (0.8 g, 1.4 mmol) and tricyclohexylphosphine (0.8 g, 2.8 mmol) were added under reflux, and heated and stirred for 3 hours. After completion of the reaction, the reaction solution was cooled to room temperature and then filtered. Water was added to the filtrate, extracted with chloroform, and the organic layer was dried over anhydrous magnesium sulfate. The resulting material was distilled under reduced pressure and then recrystallized from ethanol to obtain Compound 3-1 (15.5 g, 90%).

2) Preparation of Compound 3-2

Intermediate 3-1 (15.7 g, 50 mmol) and 2-chloro-4,6-diphenyl-1,3,5-triazine (14.4 g, 54 mmol) were added to 200 ml of tetrahydrofuran under a nitrogen atmosphere, and the mixture was stirred and refluxed. Then, potassium carbonate (20.3 g, 147 mmol) was added by dissolving in 60 ml of water and thoroughly stirred. Tetrakistriphenyl-phosphinopalladium (1.7 g, 1.5 mmol) was then added thereto. After reaction for 18 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Compound 3-2 (18.4 g, 80%). 2-Chloro-4,8-diphenyl-1,3,5-triazine was purchased from Alpha.

3) Preparation of Example 3

Intermediate 3-2 (10.0 g, 21 mmol) and dibenzo[b,d]furan-4~ylboronic acid (10.0 g, 47 mmol) were added to 200 ml of tetrahydrofuran under a nitrogen atmosphere, and the mixture was stirred and refluxed. Then, potassium phosphate (27.2 g, 128 mmol) was added by dissolving in 60 mi of water and thoroughly stirred. Bis(dibenzylideneacetone)palladium (0.7 g, 1.3 mmol) and tricyclohexylphosphine (0.7 g, 2.8 mmol) were then added thereto. After reaction for 24 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Example 3 (8.4 g, 54%).

MS: $[M+H]^+=731$

Example 4

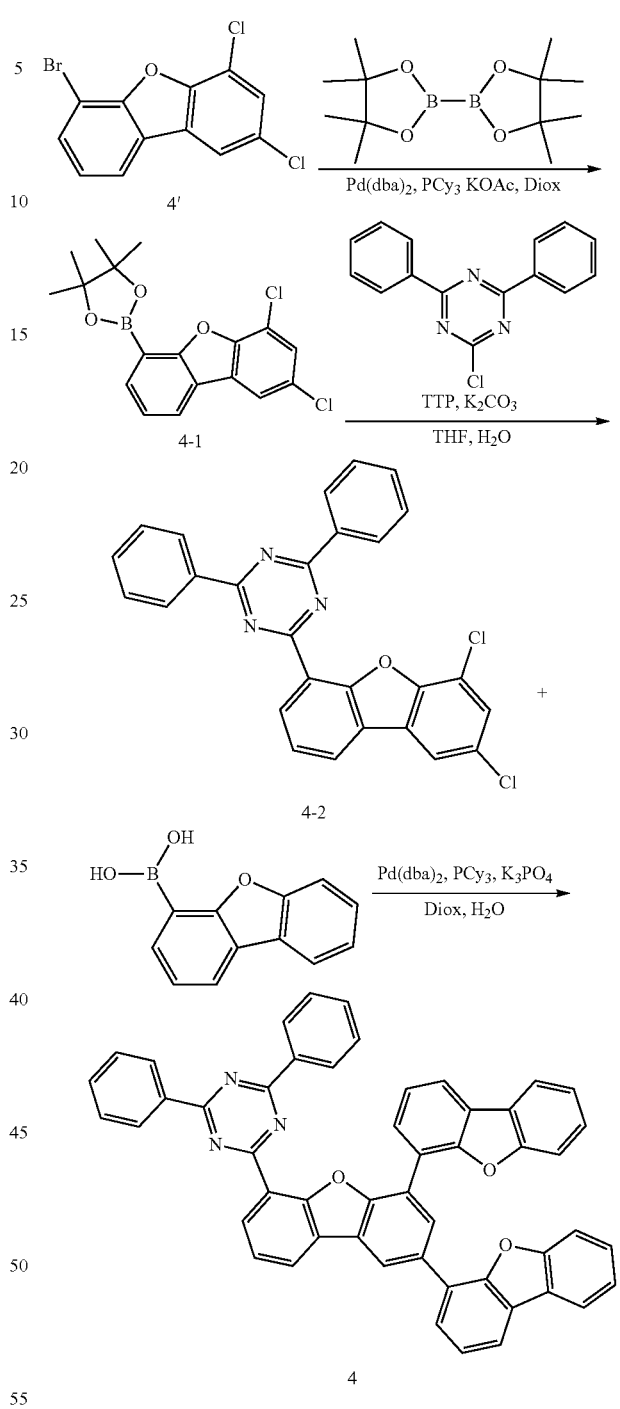

1) Preparation of Compound 4-1

Intermediate 4' (15.0 g, 48 mmol) and potassium acetate (14 g, 142 mmol) were mixed under a nitrogen atmosphere, and the mixture was added to 150 ml of dioxane and heated with stirring. Bis(dibenzylideneacetone)palladium (0.8 g, 1.4 mmol) and tricyclohexylphosphine (0.8 g, 2.8 mmol) were added under reflux, and heated and stirred for 3 hours. After completion of the reaction, the reaction solution was cooled to room temperature and then filtered. Water was added to the filtrate, extracted with chloroform, and the organic layer was dried over anhydrous magnesium sulfate.

The resulting material was distilled under reduced pressure and then recrystallized from ethanol to obtain Compound 4-1 (14.5 g, 84%).

2) Preparation of Compound 4-2

Intermediate 4-1 (14.5 g, 48 mmol) and 2-chloro-4,8-diphenyl-1,3,5-triazine (13.5 g, 50 mmol) were added to 200 ml of tetrahydrofuran under a nitrogen atmosphere, and the mixture was stirred and refluxed. Then, potassium carbonate (19.0 g, 138 mmol) was added by dissolving in 60 ml of water and thoroughly stirred. Tetrakistriphenyl-phosphinopalladium (1.6 g, 1.4 mmol) was then added thereto. After reaction for 18 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Compound 4-2 (18.1 g, 84%). 2-Chloro-4,6-diphenyl-1,3,5-triazine was purchased from Alpha.

3) Preparation of Example 4

Intermediate 4-2 (10.0 g, 21 mmol) and dibenzo[b,d]furan-4-ylboronic acid (10.0 g, 47 mmol) were added to 200 ml of tetrahydrofuran under a nitrogen atmosphere, and the mixture was stirred and refluxed. Then, potassium phosphate (27.2 g, 128 mmol) was added by dissolving in 60 ml of water and thoroughly stirred. Bis(dibenzylideneacetone)palladium (0.7 g, 1.3 mmol) and tricyclohexylphosphine (0.7 g, 2.8 mmol) were then added thereto. After reaction for 24 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Example 4 (9.5 g, 61%).

MS: [M+H]⁺=731

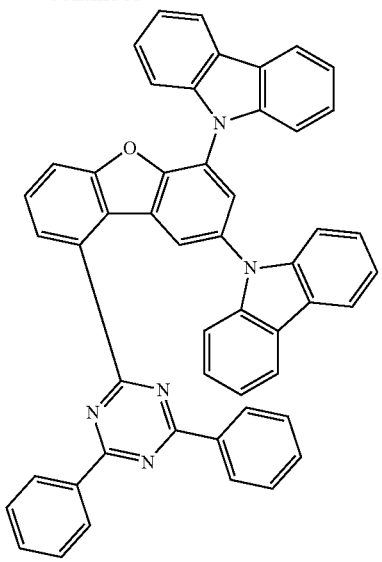

Intermediate 1-2 (10.0 g, 21 mmol) and 9H-carbazole (10.0 g, 47 mmol) were added to 100 ml of xylene under a nitrogen atmosphere, and the mixture was stirred and refluxed. Then, sodium t-buthoxide (8.3 g, 86 mmol) was added and then thoroughly stirred. Bis(tri-tert-butylphosphine)palladium(0) (0.2 g, 0.4 mmol) was then added thereto. After reaction for 24 hours, the reaction solution was cooled to room temperature and filtrated. The filtrate was extracted with chloroform and water, and then the organic layer was dried with magnesium sulfate. The organic layer was then distilled under reduced pressure and recrystallized using ethyl acetate. The resulting solid was filtered and then dried to give Example 5 (11.5 g, 71%).

MS: [M+H]⁺=730

Example 5

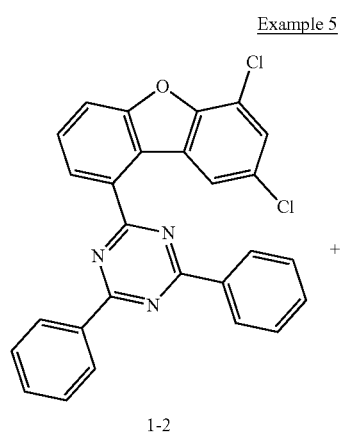

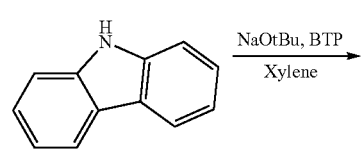

Example 6

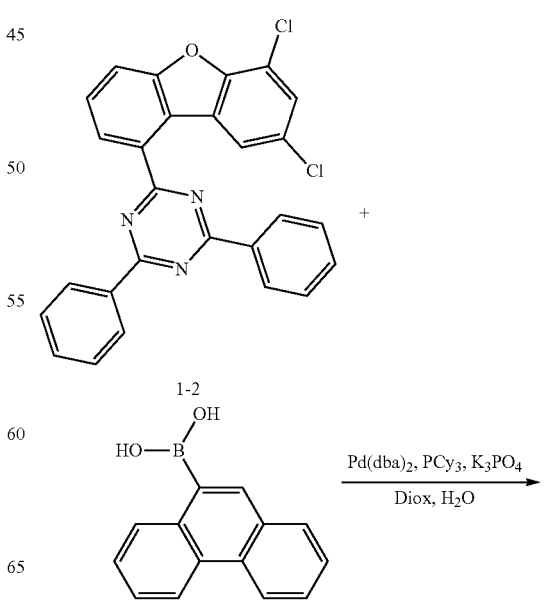

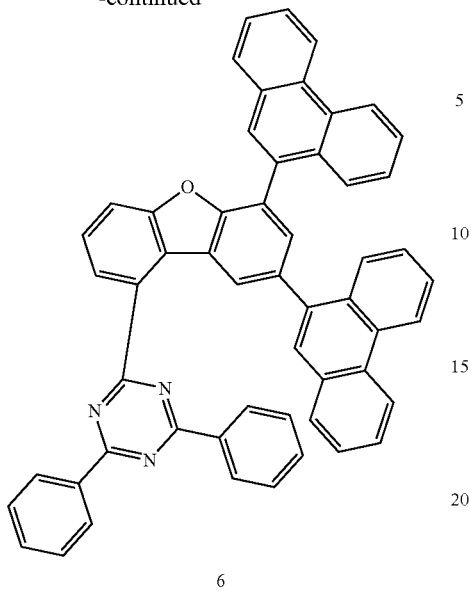

6

Intermediate 1-2 (10.0 g, 21 mmol) and phenanthrene-9-yl boronic acid (10.4 g, 47 mmol) were added to 200 ml of tetrahydrofuran under a nitrogen atmosphere and the mixture was stirred and refluxed. Then, potassium phosphate (27.2 g, 128 mmol) was added by dissolving in 60 mi of water and then thoroughly stirred. Bis(dibenzylideneacetone)palladium (0.7 g, 1.3 mmol) and tricyclohexylphosphine (0.7 g, 2.6 mmol) were added thereto. After reaction for 24 hours, the reaction solution was cooled to room temperature and filtrated. The filtrate was extracted with chloroform and water, and then the organic layer was dried with magnesium sulfate. The organic layer was then distilled under reduced pressure and recrystallized using ethyl acetate. The resulting solid was filtered and then dried to give Example 6 (12.6 g, 81%).

MS: $[M+H]^+=751$

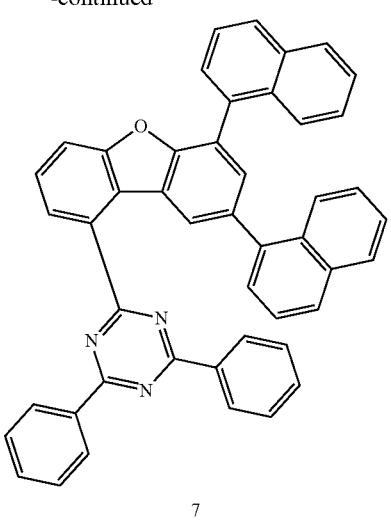

7

Intermediate 1-2 (10.0 g, 21 mmol) and phenanthrene-9-yl boronic add (10.4 g, 47 mmol) were added to 200 ml of tetrahydrofuran under a nitrogen atmosphere and the mixture was stirred and refluxed. Then, potassium phosphate (27.2 g, 128 mmol) was added by dissolving in 60 ml of water and then thoroughly stirred. Bis(dibenzylideneacetone)palladium (0.7 g, 1.3 mmol) and tricyclohexylphosphine (0.7 g, 2.6 mmol) were added thereto. After reaction for 24 hours, the reaction solution was cooled to room temperature and filtrated. The filtrate was extracted with chloroform and water, and then the organic layer was dried with magnesium sulfate. The organic layer was then distilled under reduced pressure and recrystallized using ethyl acetate. The resulting solid was filtered and then dried to give Example 6 (12.6 g, 81%).

MS: $[M+H]^+=651$

Example 7

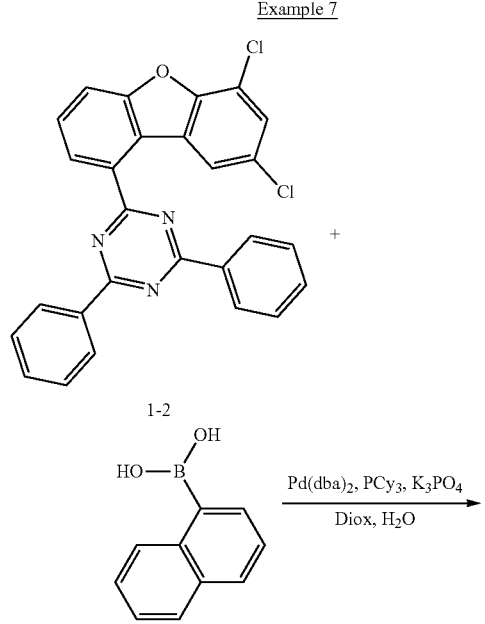

Example 8

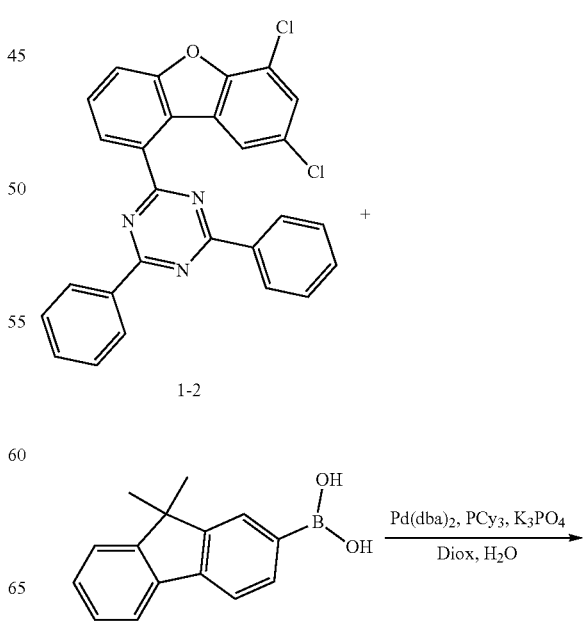

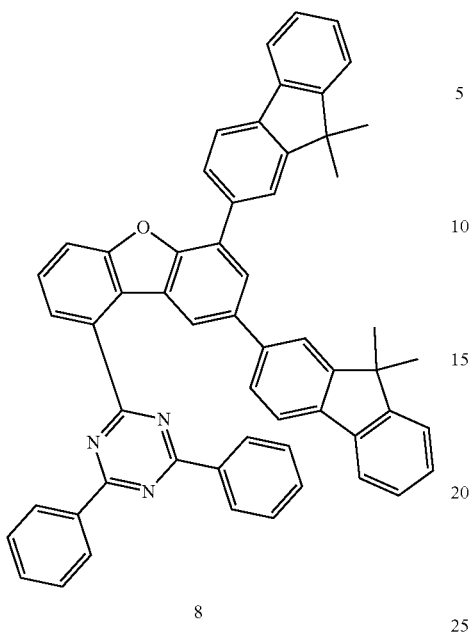
8
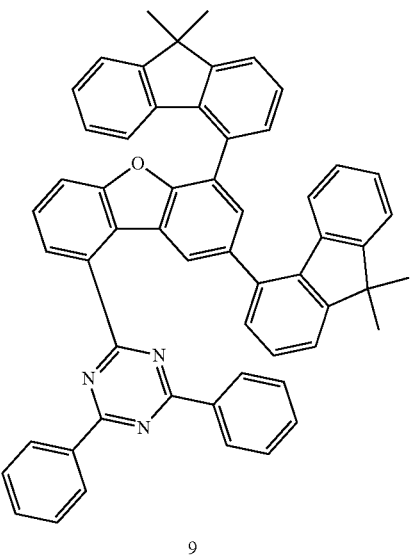
9
Example 8 (12 g, 77%) was prepared in the same manner as in Example 7, except that the material reacting with intermediate 1-2 was changed as in the above Reaction Scheme.
MS: [M+H]$^+$=783
Example 9 (10 g, 68%) was prepared in the same manner as in Example 7, except that the material reacting with intermediate 1-2 was changed as in the above Reaction Scheme.
MS: [M+H]$^+$=783
Example 9
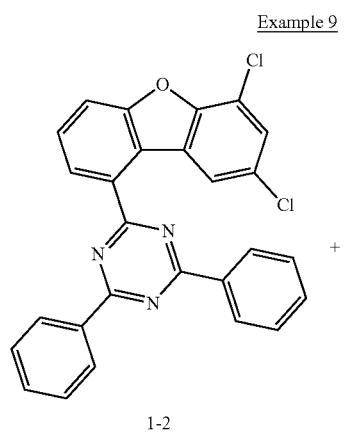
1-2
Example 10
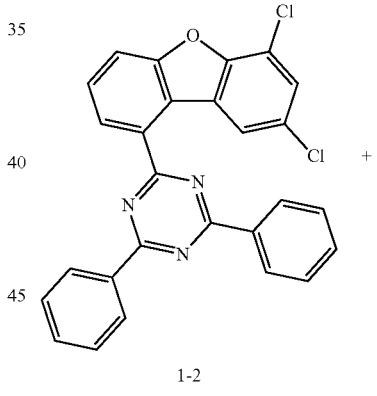
1-2
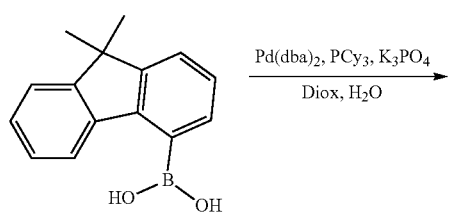
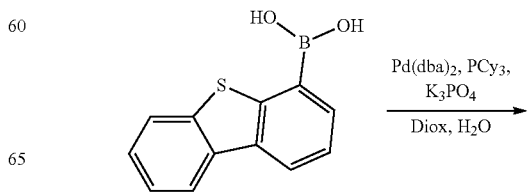

91
-continued
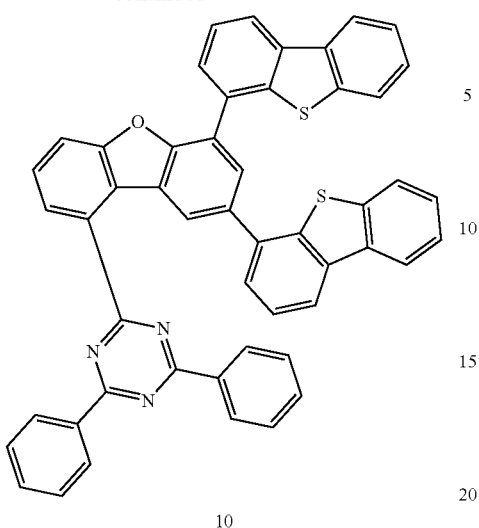
10
Example 10 (11 g, 70%) was prepared in the same manner as in Example 7, except that the material reacting with intermediate 1-2 was changed as in the above Reaction Scheme.
MS: [M+H]⁺=763
Example 11
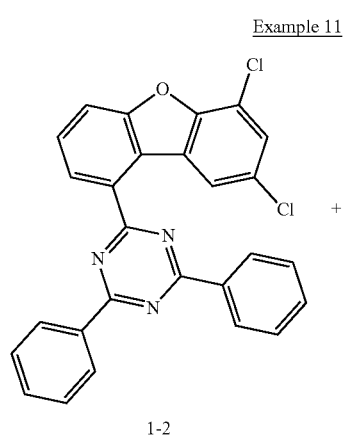
1-2
+
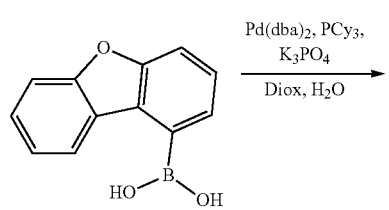
92
-continued
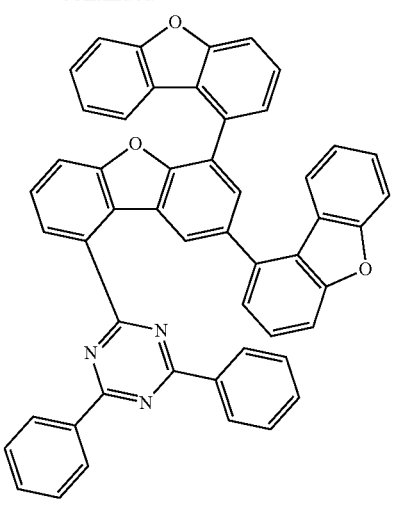
11
Example 11 (12 g, 74%) was prepared in the same manner as in Example 7, except that Intermediate 1-2 was changed as in the above Reaction Scheme.
MS: [M+H]⁺=731
Example 12
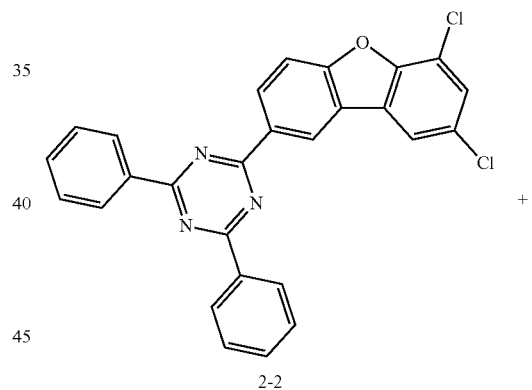
+
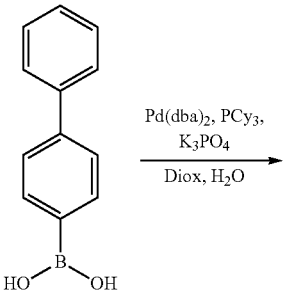

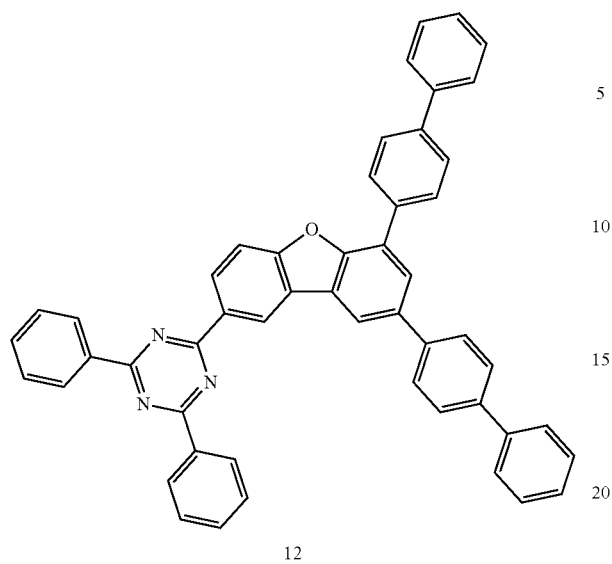
12
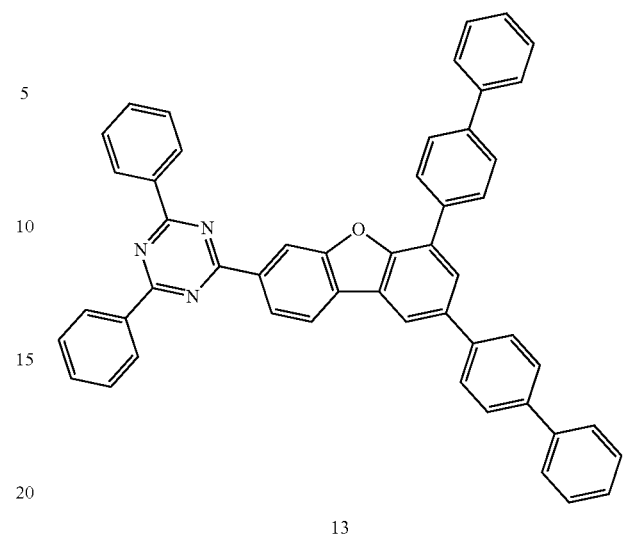
13
Example 12 (11 g, 68%) was prepared in the same manner as in Example 2, except that the material reacting with Intermediate 2-2 was changed as in the above Reaction Scheme.
MS: [M+H]$^+$=703
Example 13 (7 g, 41%) was prepared in the same manner as in Example 3, except that the material reacting with Intermediate 3-2 was changed as in the above Reaction Scheme.
MS: [M+H]$^+$=703
Example 13
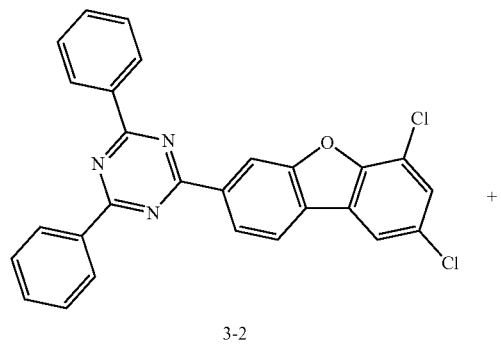
3-2
Example 14
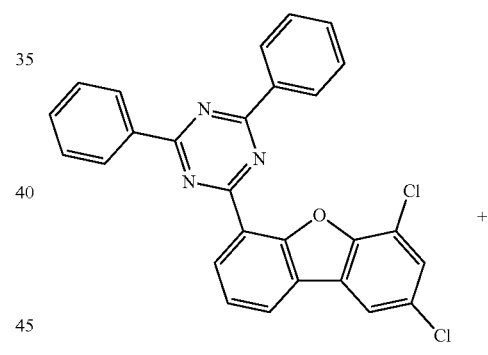
4-2
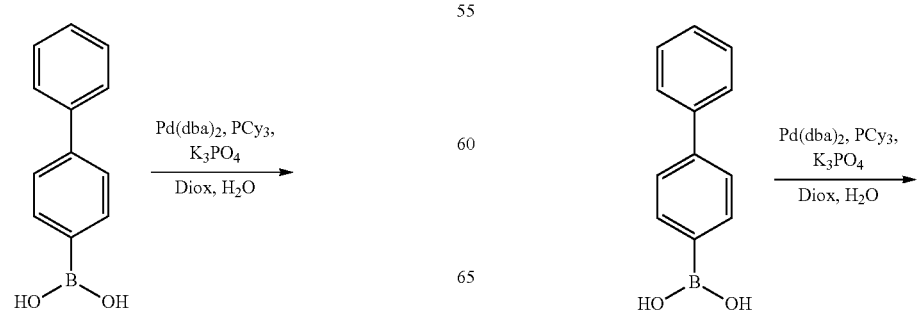

95
-continued

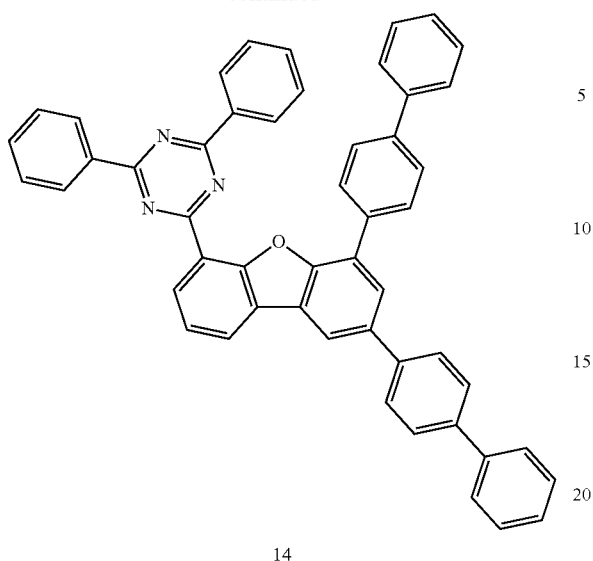

14

Example 14 (10 g, 63%) was prepared in the same manner as in Example 4, except that the material reacting with intermediate 4-2 was changed as in the above Reaction Scheme.

MS: [M+H]$^+$=703

Example 15

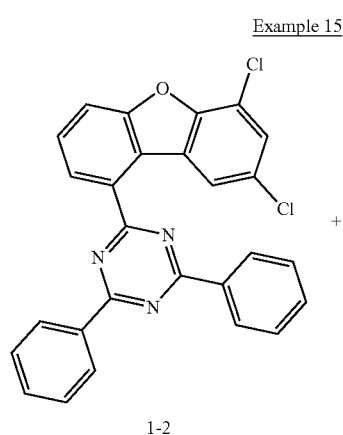

1-2

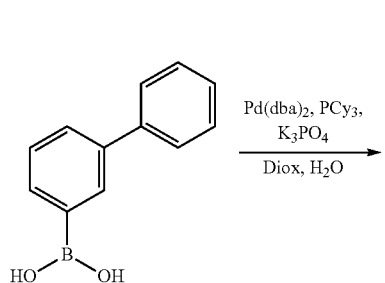

96
-continued

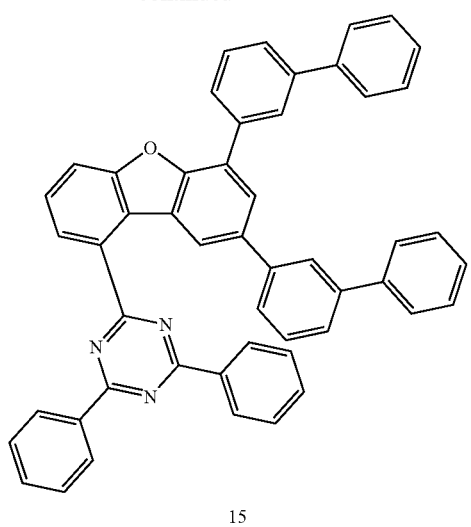

15

Example 15 (13 g, 78%) was prepared in the same manner as in Example 7, except that the material reacting with Intermediate 1-2 was changed as in the above Reaction Scheme.

MS: [M+H]$^+$=703

Example 16

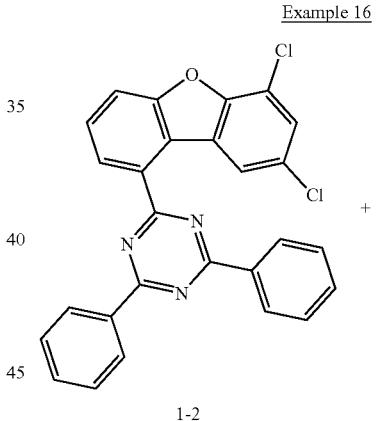

1-2

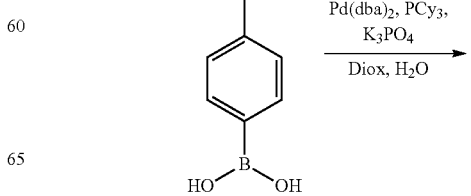

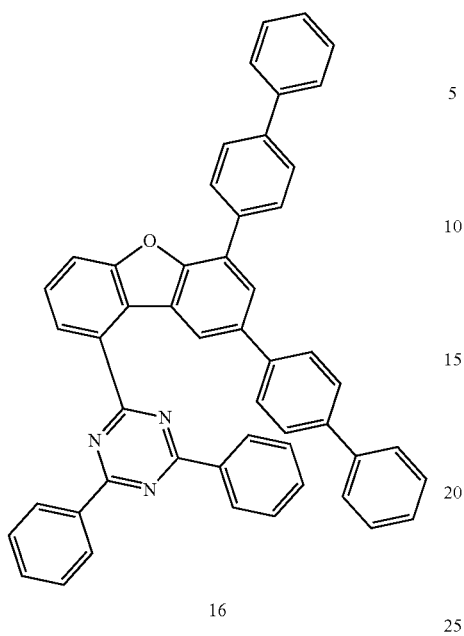
16
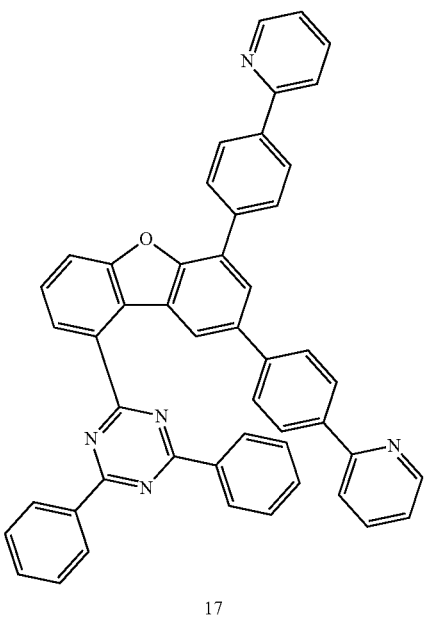
17
Example 16 (11 g, 70%) was prepared in the same manner as in Example 7, except that the material reacting with intermediate 1-2 was changed as in the above Reaction Scheme.
MS: [M+H]$^+$=703
Example 17 (9 g, 53%) was prepared in the same manner as in Example 7, except that the material reacting with intermediate 1-2 was changed as in the above Reaction Scheme.
MS: [M+H]$^+$=705
Example 17
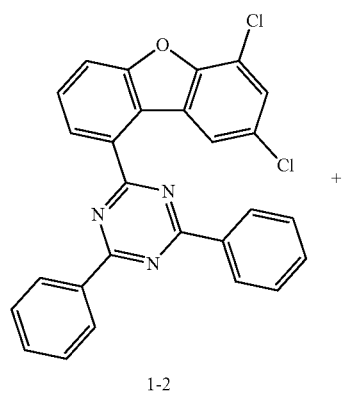
1-2
Example 18
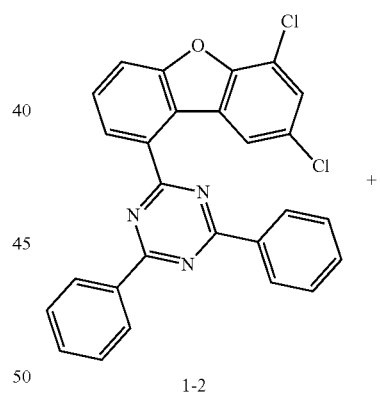
1-2
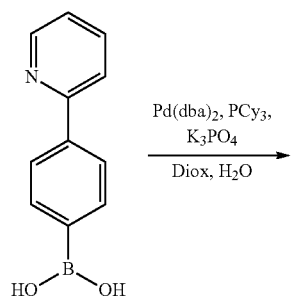
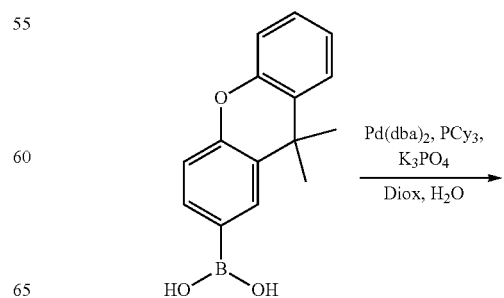

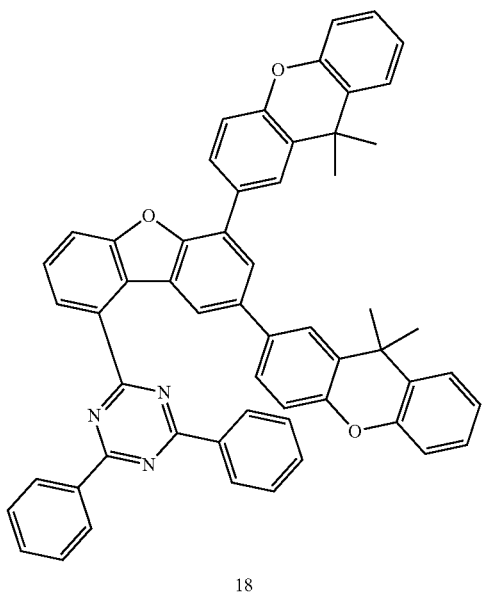
18
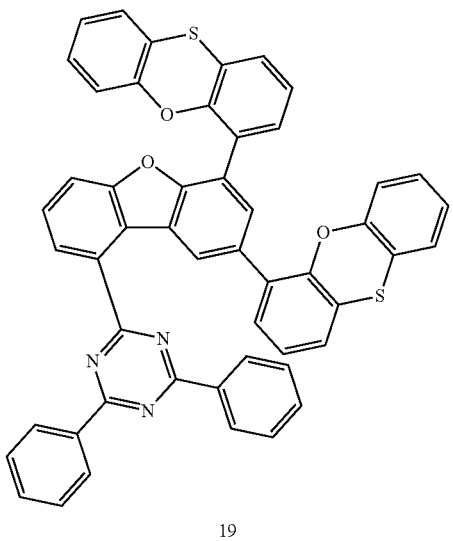
19
Example 18 (10 g, 60%) was prepared in the same manner as in Example 7, except that the material reacting with intermediate 1-2 was changed as in the above Reaction Scheme.
MS: [M+H]$^+$=815
Example 19 (11 g, 71%) was prepared in the same manner as in Example 7, except that the material reacting with Intermediate 1-2 was changed as in the above Reaction Scheme.
MS: [M+H]$^+$=795
Example 19
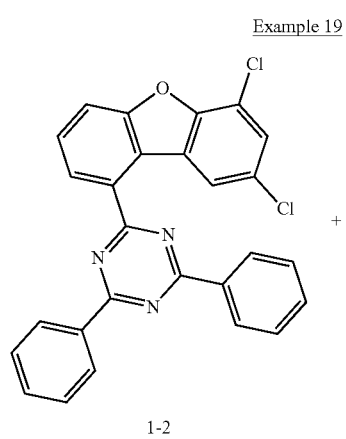
1-2
Example 20
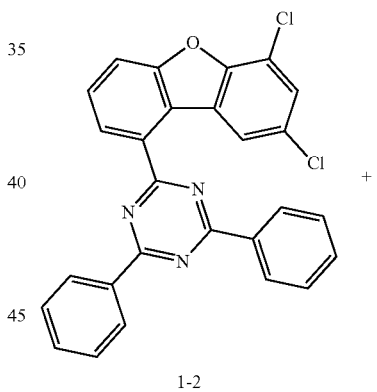
1-2
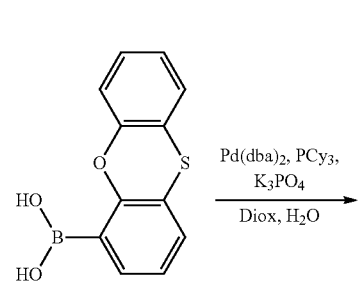
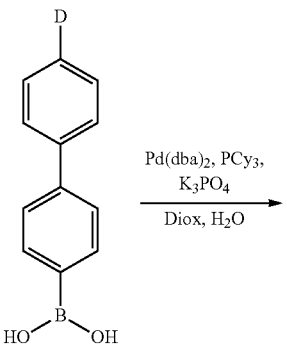

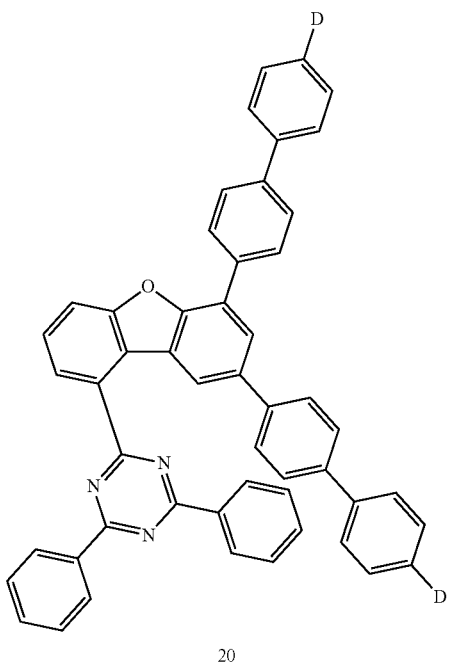
20
Example 20 (11 g, 65%) was prepared in the same manner as in Example 7, except that the material reacting with intermediate 1-2 was changed as in the above Reaction Scheme.
MS: [M+H]⁺=705
Example 21
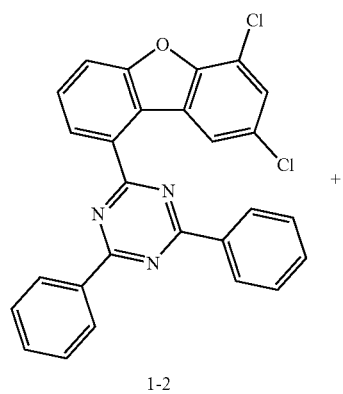
1-2
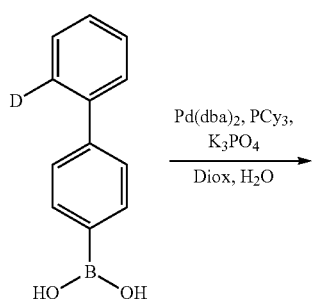
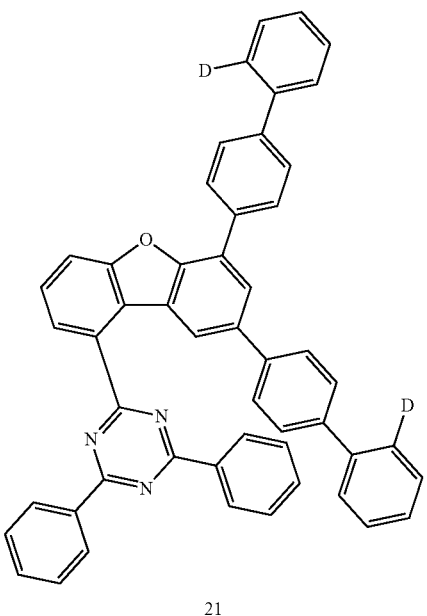
21
Example 21 (11 g, 68%) was prepared in the same manner as in Example 7, except that the material reacting with intermediate 1-2 was changed as in the above Reaction Scheme.
MS: [M+H]⁺=705
Example 22
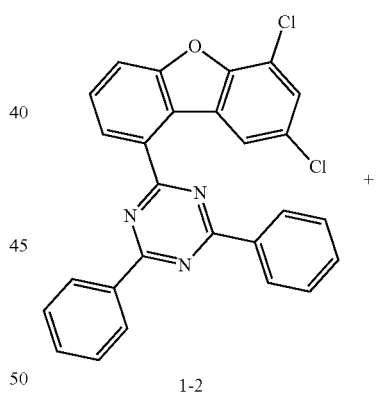
1-2
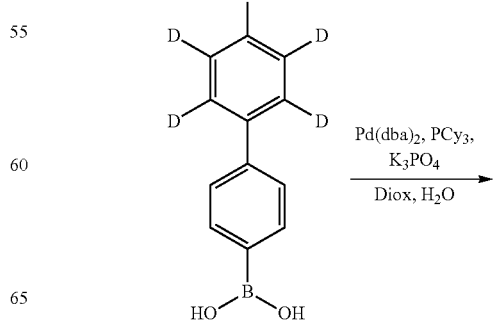

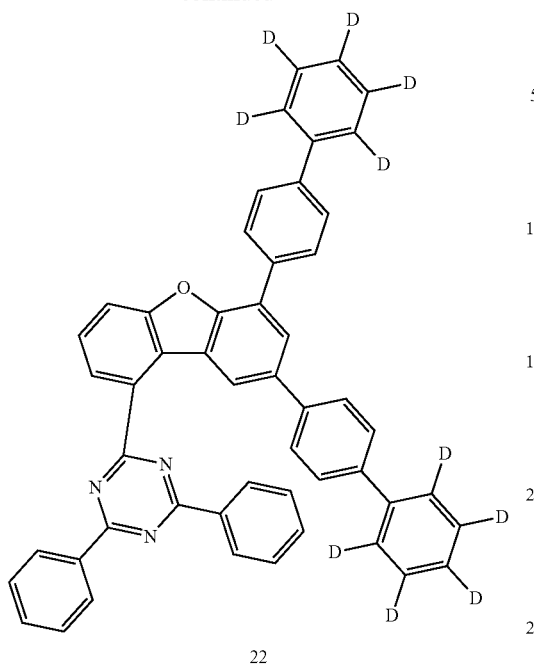
22
Example 22 (8 g, 51%) was prepared in the same manner as in Example 7, except that the material reacting with intermediate 1-2 was changed as in the above Reaction Scheme.
MS: [M+H]⁺=713
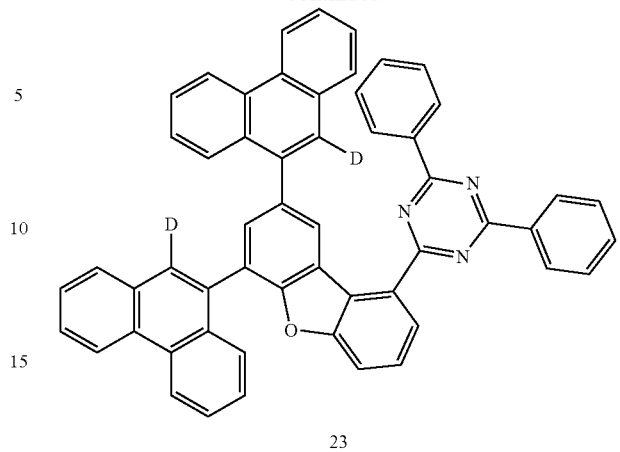
23
Example 23 (13 g, 80%) was prepared in the same manner as in Example 7, except that the material reacting with intermediate 1-2 was changed as in the above Reaction Scheme.
MS: [M+H]⁺=753
Example 23
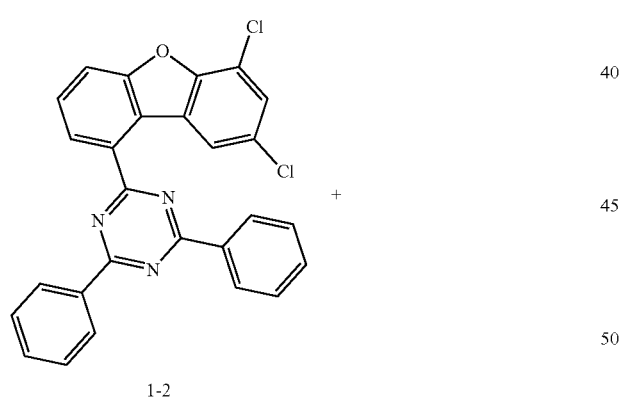
1-2
Example 24
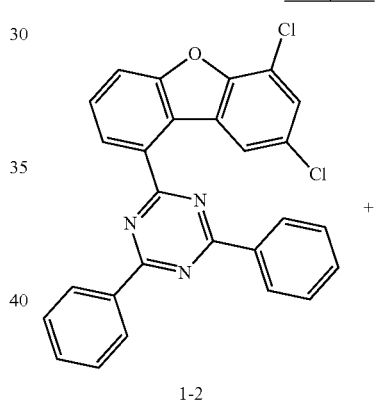
1-2
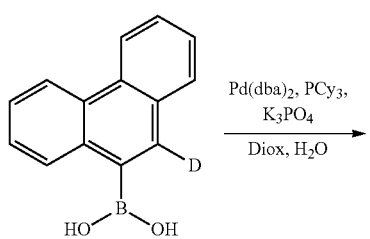
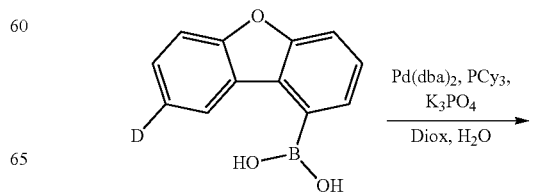

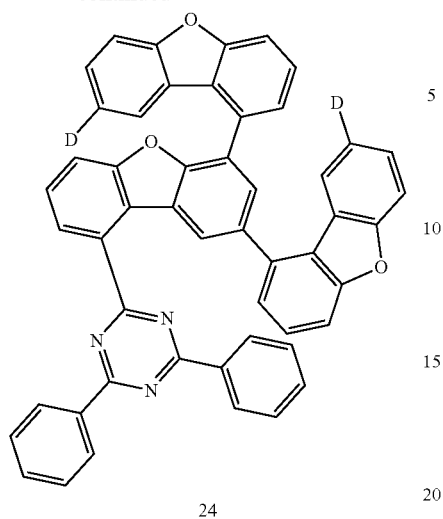
24
Example 24 (11 g, 69%) was prepared in the same manner as in Example 7, except that the material reacting with intermediate 1-2 was changed as in the above Reaction Scheme.
MS: [M+H]$^+$=733
Example 25
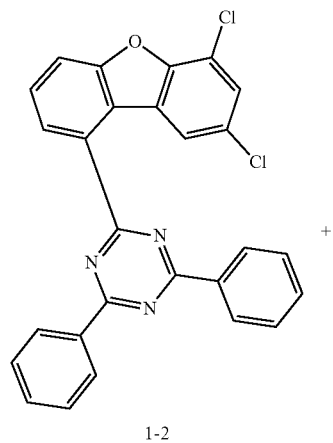
1-2
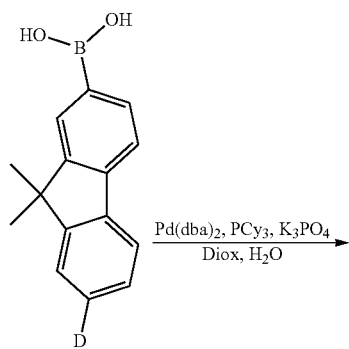
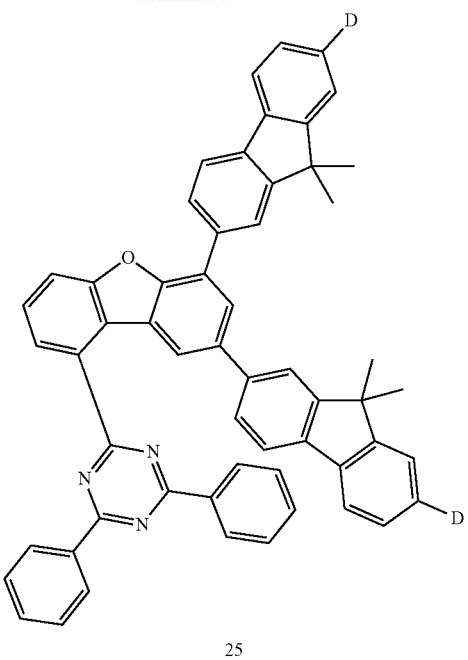
25
Example 25 (5 g, 31%) was prepared in the same manner as in Example 7, except that the material reacting with Intermediate 1-2 was changed as in the above Reaction Scheme.
MS: [M+H]$^+$=785
Example 27
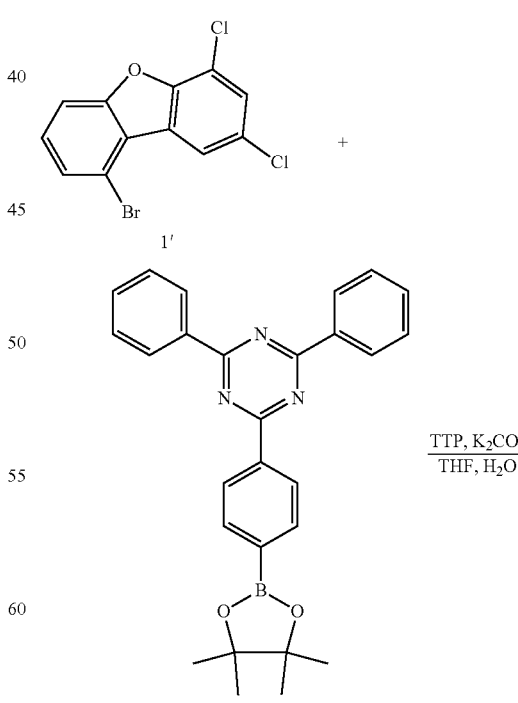

-continued

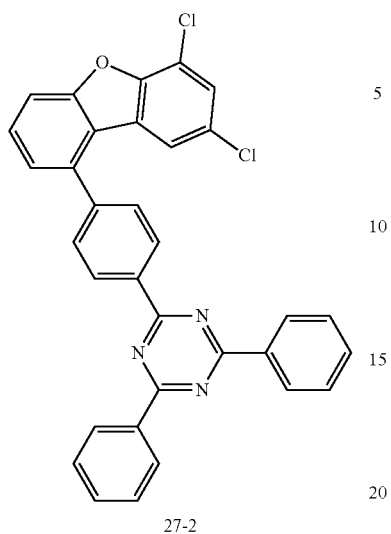

27-2

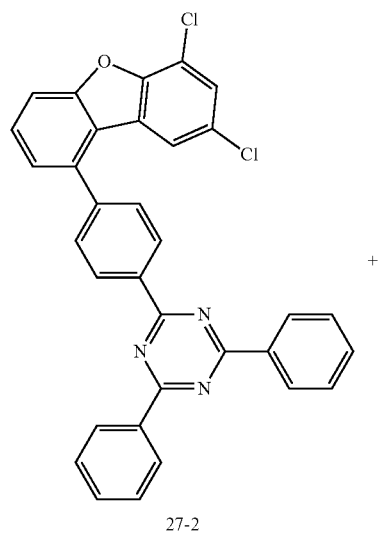

27-2

+

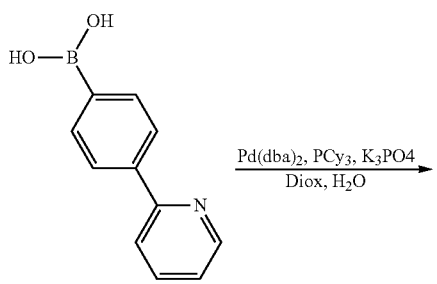

Pd(dba)₂, PCy₃, K₃PO₄
Diox, H₂O
→

-continued

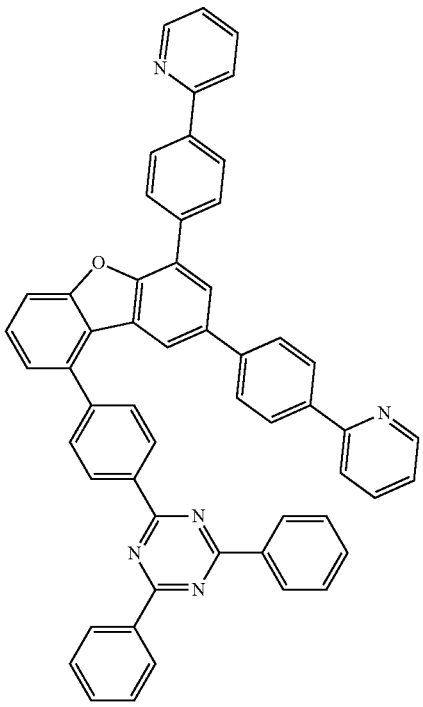

27

1) Preparation of Compound 27-2

Intermediate 1'(15 g: 48 mmol) and Compound 27-1 (22.7 g, 52 mmol) were added to 200 ml of tetrahydrofuran under a nitrogen atmosphere, and the mixture was stirred and refluxed. Then, potassium carbonate (20 g, 142 mmol) was added by dissolving in 60 ml of water and thoroughly stirred, Tetrakistriphenyl-phosphinopalladium (1.8 g, 1.4 mmol) was then added thereto. After reaction for 16 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Compound 27-2 (18 g, 70%).

2) Preparation of Example 27

Compound 27-2 (10 g, 21 mmol) and (4-(pyridin-2-yl)phenyl)boronic acid (8.0 g, 40 mmol) were added to 150 ml of tetrahydrofuran under a nitrogen atmosphere and the mixture was stirred and refluxed. Then, potassium phosphate (23.4 g, 21 mmol) was added by dissolving in 60 ml of water and thoroughly stirred. Bis(dibenzylideneacetone)palladium (0.6 g, 1.1 mmol) and tricyclohexylphosphine (0.6 g, 2.2 mmol) were then added thereto. After reaction for 24 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Example 27 (9.5 g, 61%).

MS: [M+H]⁺=781

Example 28
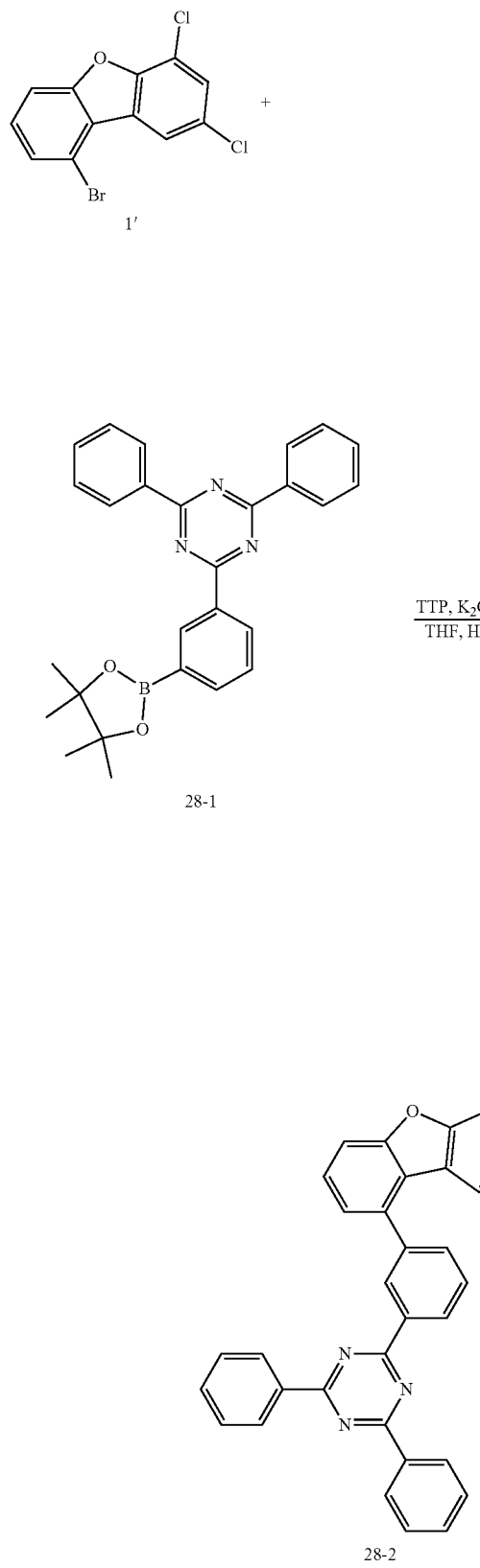
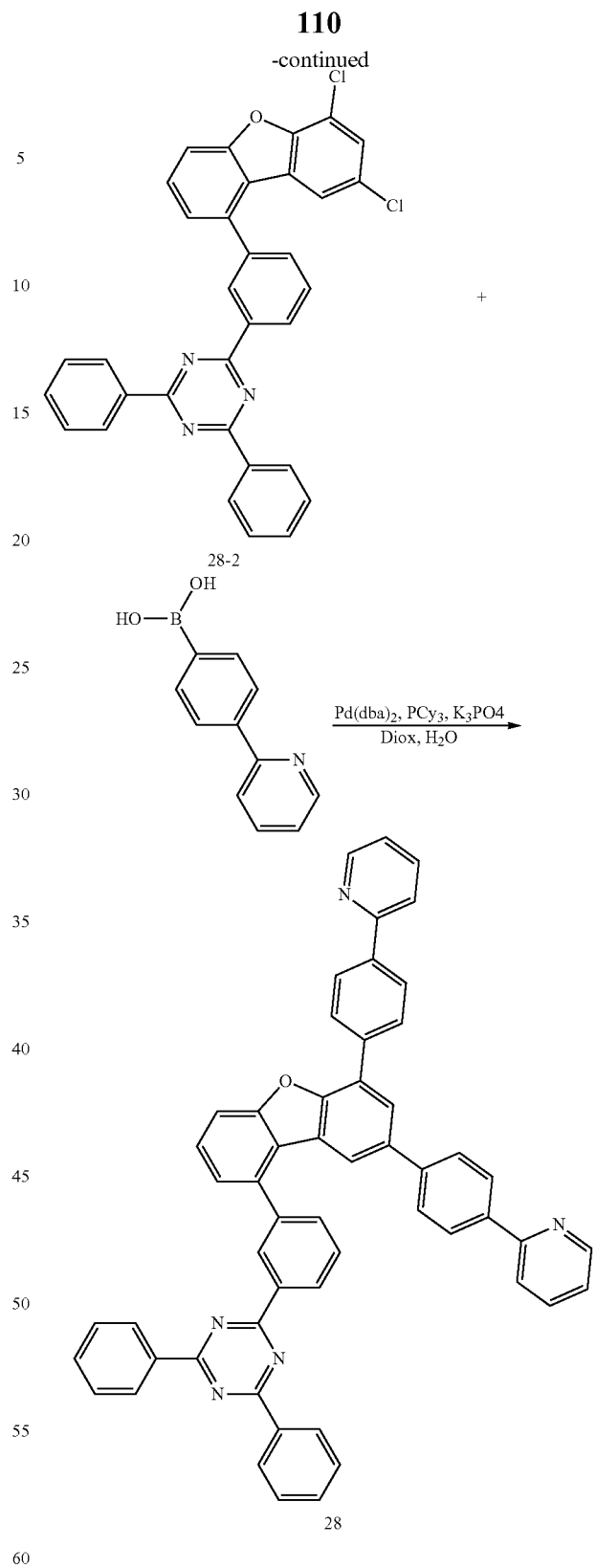
1) Preparation of Compound 28-2
Intermediate 1'(15 g, 48 mmol) and Compound 28-1 (22.7 g, 52 mmol) were added to 200 ml of tetrahydrofuran under a nitrogen atmosphere, and the mixture was stirred and refluxed. Then, potassium carbonate (20 g, 142 mmol) was added by dissolving in 60 ml of water and thoroughly stirred. Tetrakistriphenyl-phosphinopalladium (1.8 g, 1.4 mmol) was then added thereto. After reaction for 16 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Compound 28-2 (16 g, 81%).

2) Preparation of Example 28

Compound 28-2 (10 g, 21 mmol) and (4-(pyridin-2-yl)phenyl)boronic acid (8.0 g, 40 mmol) were added to 150 ml of tetrahydrofuran under a nitrogen atmosphere and the mixture was stirred and refluxed. Then, potassium phosphate (23.4 g, 21 mmol) was added by dissolving in 60 ml of water and thoroughly stirred. Bis(dibenzylideneacetone)palladium (0.6 g, 1.1 mmol) and tricyclohexylphosphine (0.6 g, 2.2 mmol) were then added thereto. After reaction for 24 hours, the reaction solution was cooled to room temperature and filtered. The filtrate was extracted with chloroform and water, and then the organic layer was dried with magnesium sulfate. The organic layer was then distilled under reduced pressure and recrystallized using ethyl acetate. The resulting solid was filtered and then dried to give Example 28 (6 g, 41%).

MS: [M+H]$^+$=781

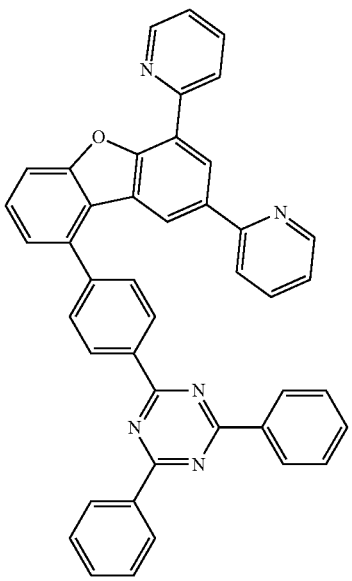

29

Example 29 (6 g, 54%) was prepared in the same manner as in Example 27, except that the material reacting with Compound 27-2 was changed as in the above Reaction Scheme.

MS: [M+H]$^+$=629

Example 29

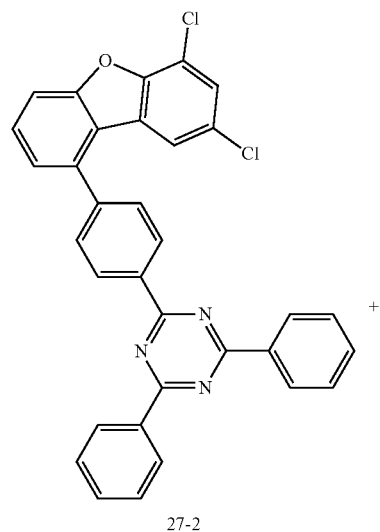

27-2

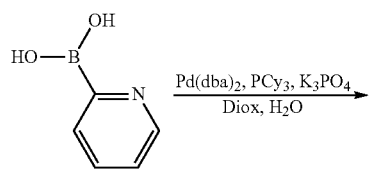

Example 30

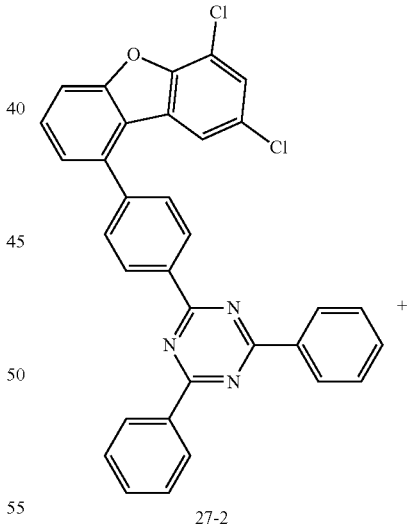

27-2

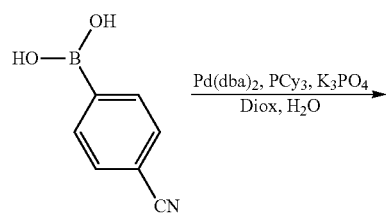

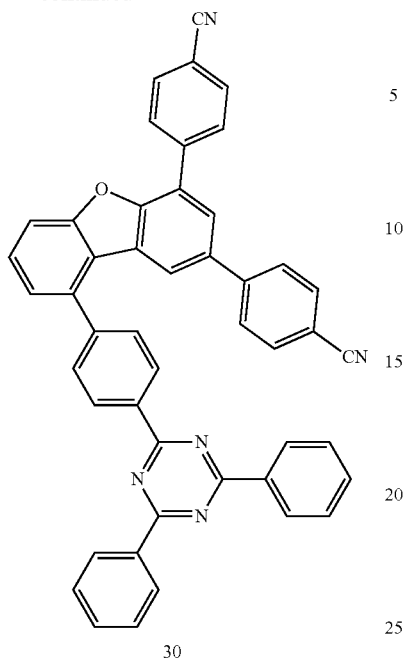
30
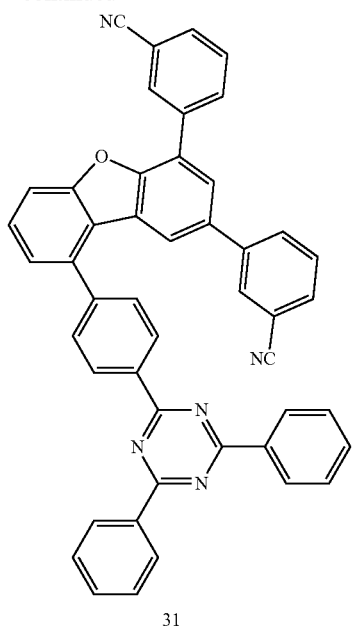
31
Example 30 (8 g, 65%) was prepared in the same manner as in Example 27, except that the material reacting with Compound 21-2 was changed as in the above Reaction Scheme.
MS: [M+H]$^+$=677
Example 31 (8 g, 65%) was prepared in the same manner as in Example 27, except that the material reacting with Compound 27-2 was changed as in the above Reaction Scheme.
MS: [M+H]$^+$=677
Example 31
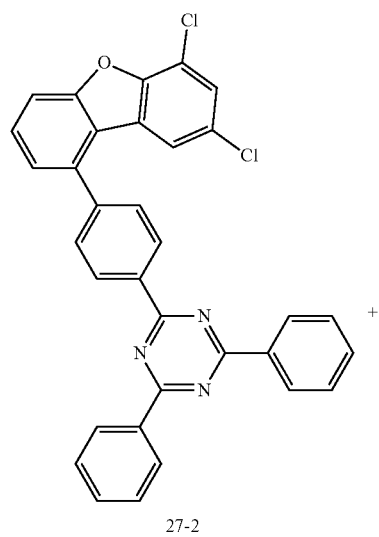
27-2
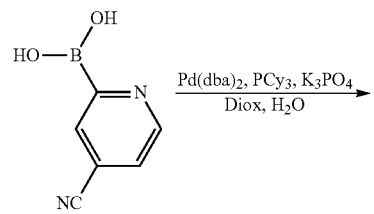
Example 32
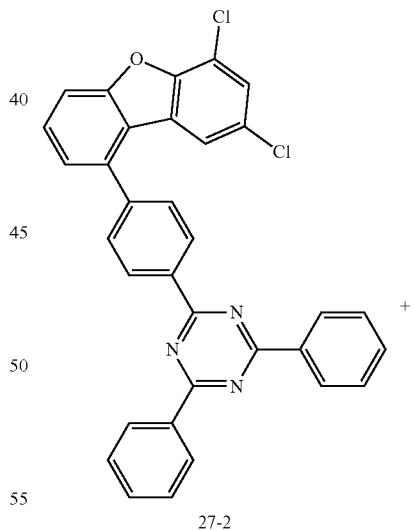
27-2
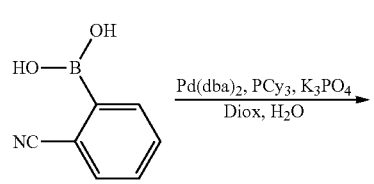

-continued
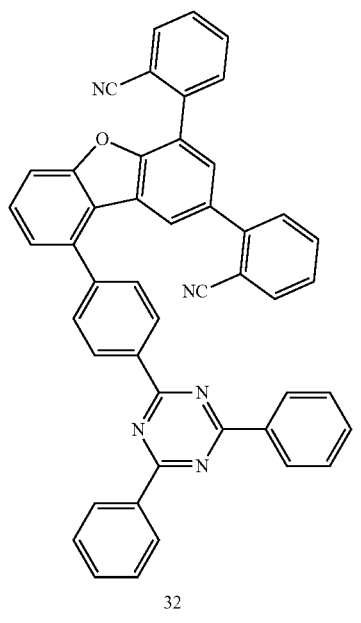
32
Example 32 (3.6 g, 29%) was prepared in the same manner as in Example 27, except that the material reacting with Compound 27-2 was changed as in the above Reaction Scheme.
MS: [M+H]$^+$=677
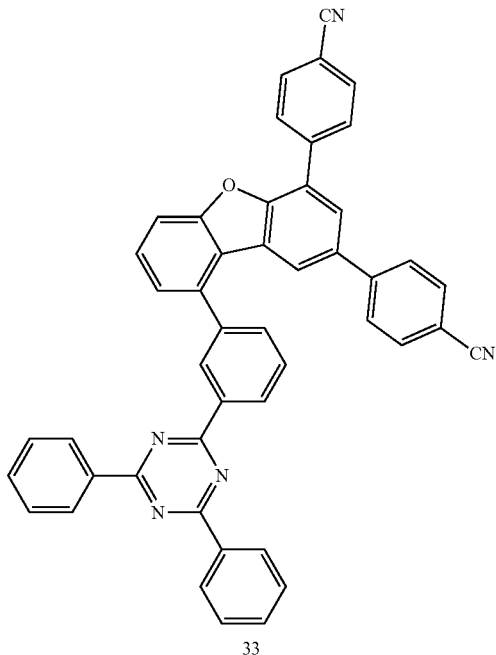
33
Example 33 (7 g, 58%) was prepared in the same manner as in Example 28, except that the material reacting with Compound 28-2 was changed as in the above Reaction Scheme.
MS: [M+H]$^+$=677
Example 33
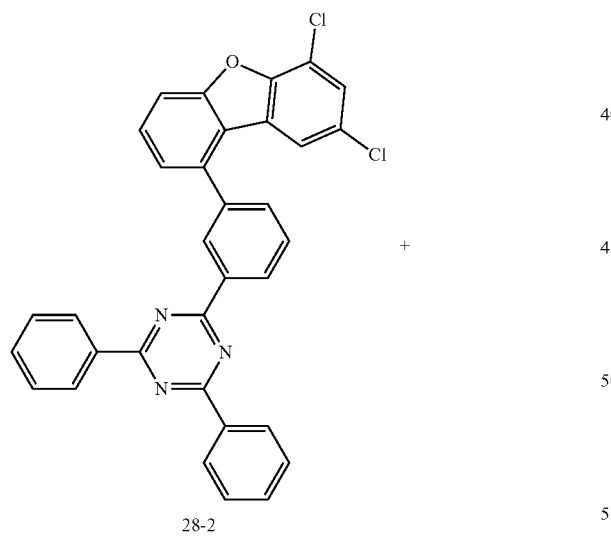
Example 34
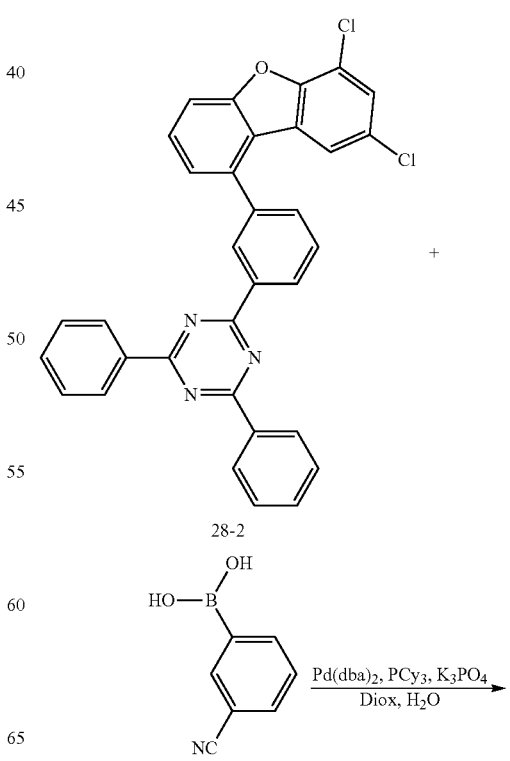

-continued
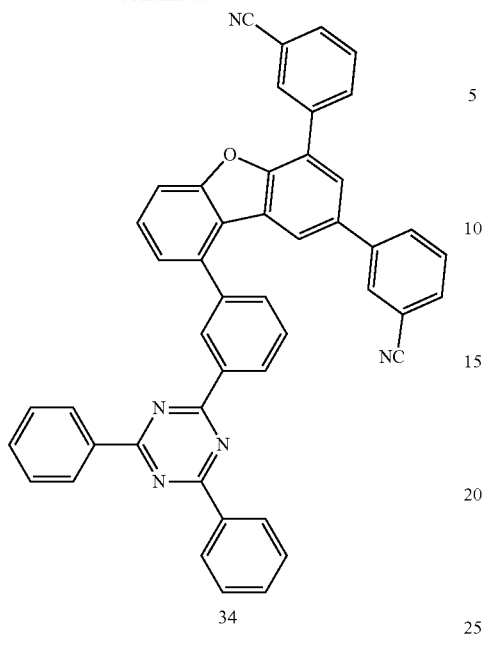
34
Example 34 (6 g, 48%) was prepared in the same manner as in Example 28, except that the material reacting with Compound 28-2 was changed as in the above Reaction Scheme.
MS: [M+H]$^+$=677
Example 35
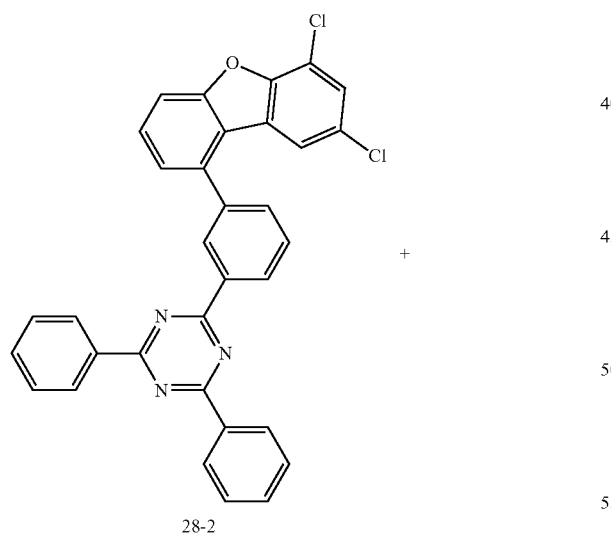
28-2
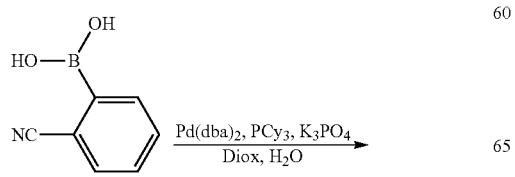
-continued
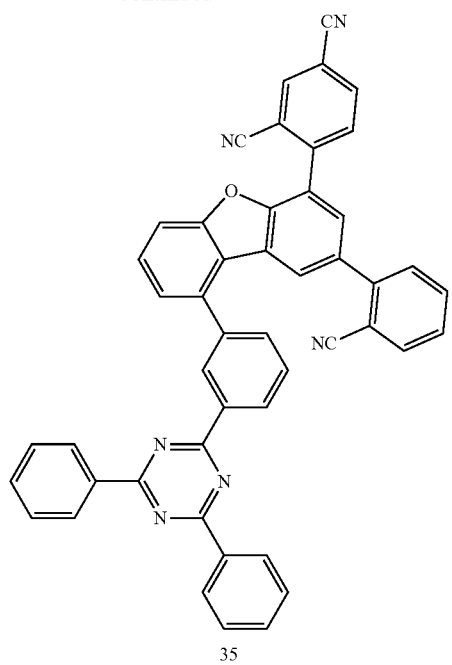
35
Example 35 (3 g, 26%) was prepared in the same manner as in Example 28, except that the material reacting with Compound 28-2 was changed as in the above Reaction Scheme.
MS: [M+H]$^+$=677
Example 36
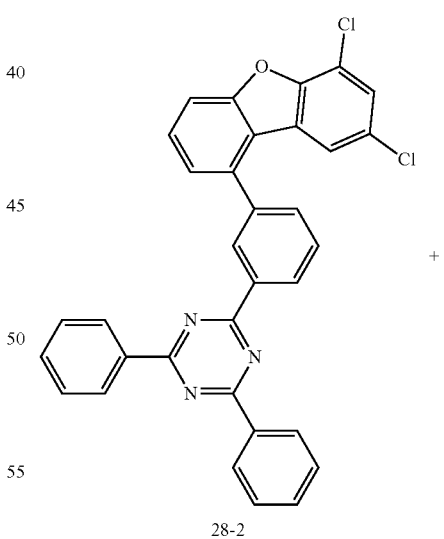
28-2
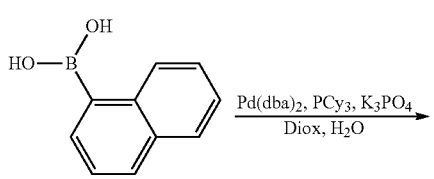

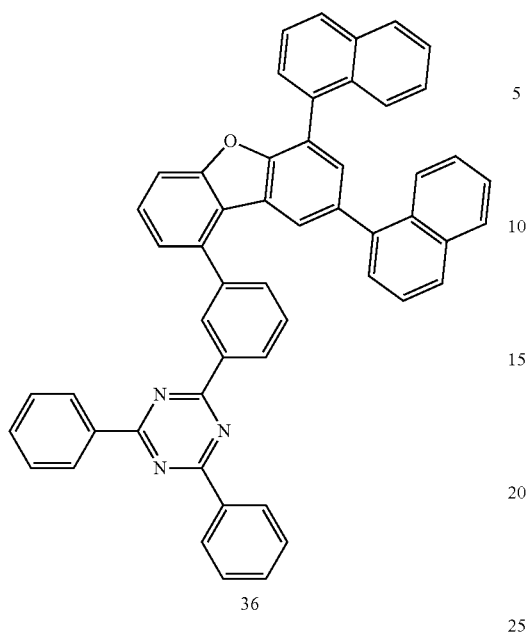
36
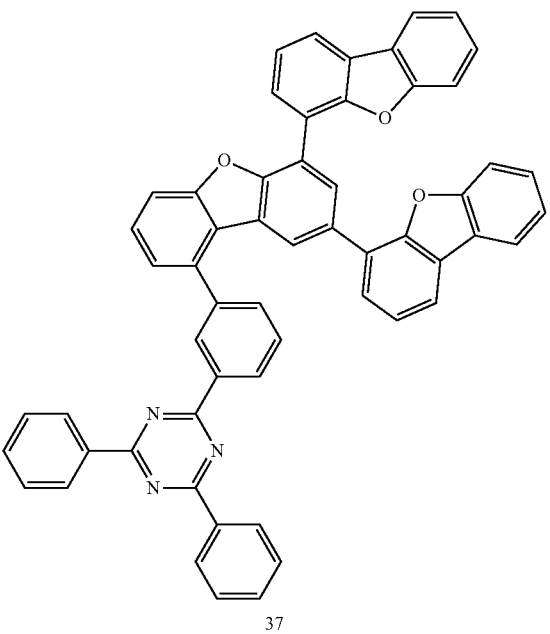
37
Example 36 (9 g, 60%) was prepared in the same manner as in Example 28, except that the material reacting with Compound 28-2 was changed as in the above Reaction Scheme.
MS: [M+H]⁺=677
Example 37 (10 g, 59%) was prepared in the same manner as in Example 28, except that the material reacting with Compound 28-2 was changed as in the above Reaction Scheme.
MS: [M+H]⁺=807
Example 37
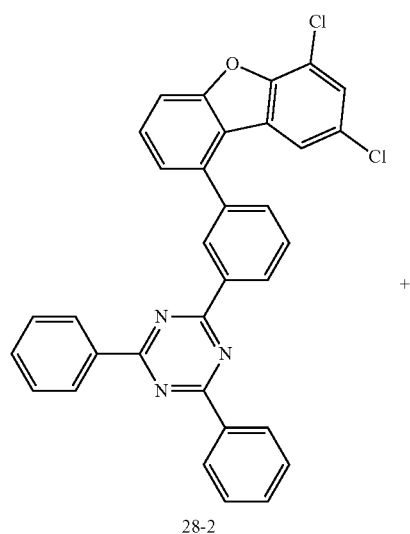
28-2
Example 38
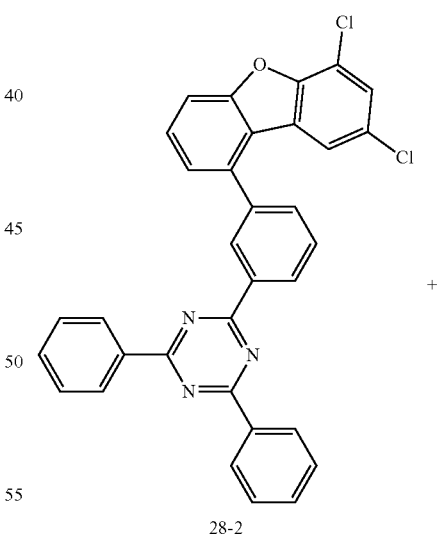
28-2
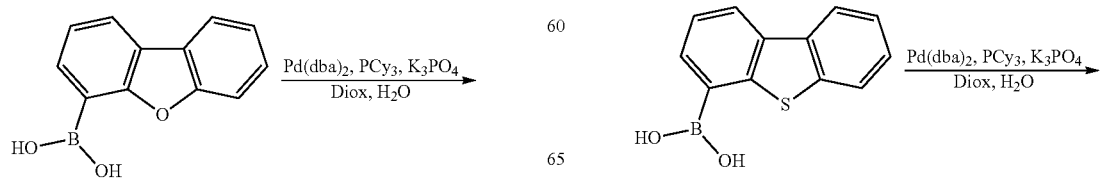

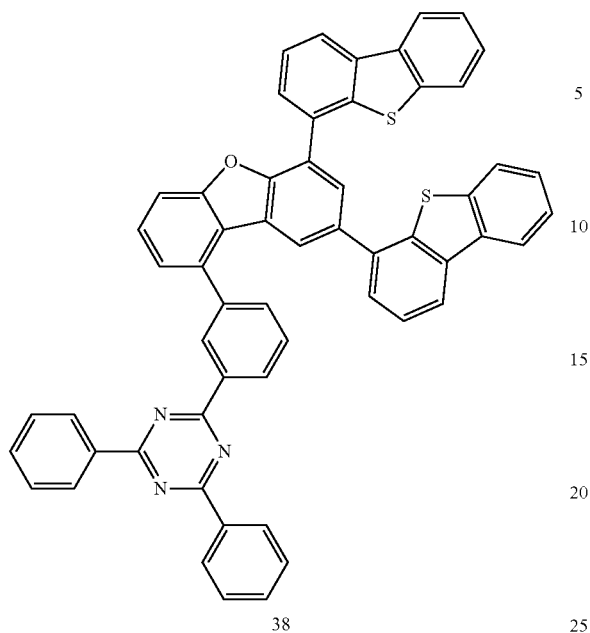

38

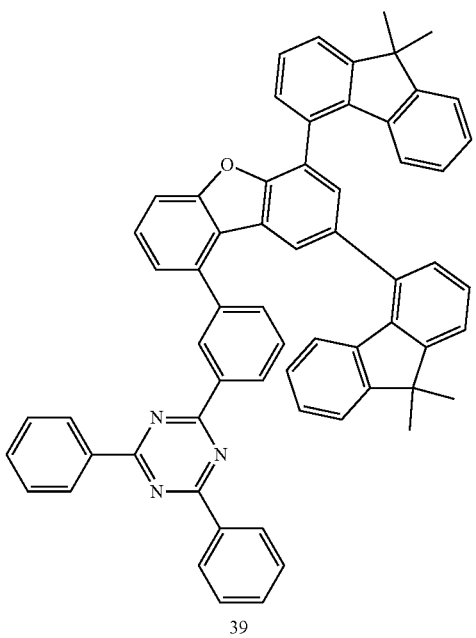

39

Example 38 (14 g, 78%) was prepared in the same manner as in Example 28, except that the material reacting with Compound 28-2 was changed as in the above Reaction Scheme.

MS: [M+H]$^+$=839

Example 39 (8 g, 41%) was prepared in the same manner as in Example 28, except that the material reacting with Compound 28-2 was changed as in the above Reaction Scheme.

MS: [M+H]$^+$=859

Comparative Example

In the comparative example, the following compounds were used.

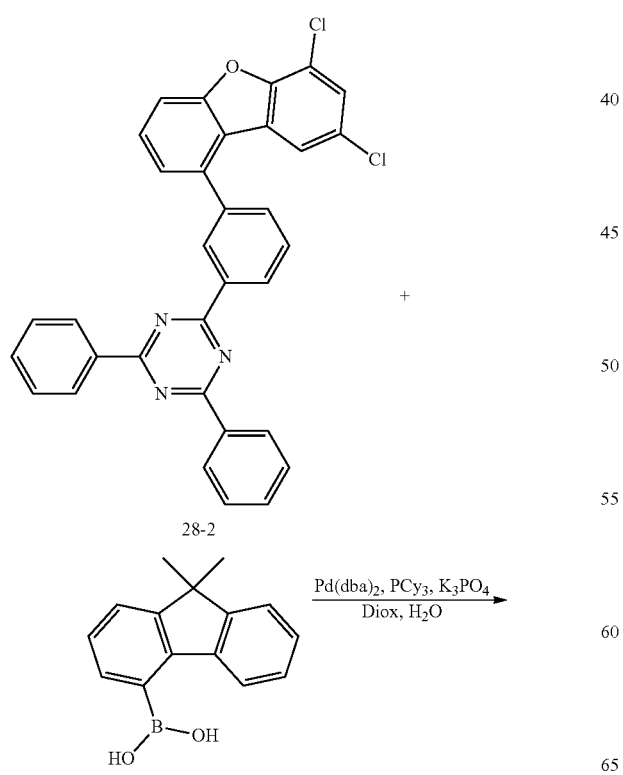

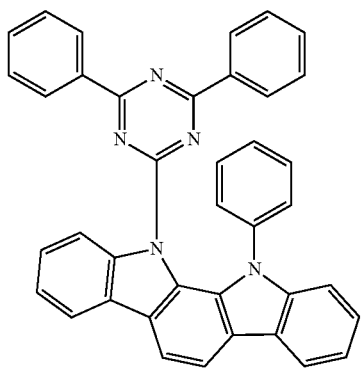

C.EX.1

C.EX.2
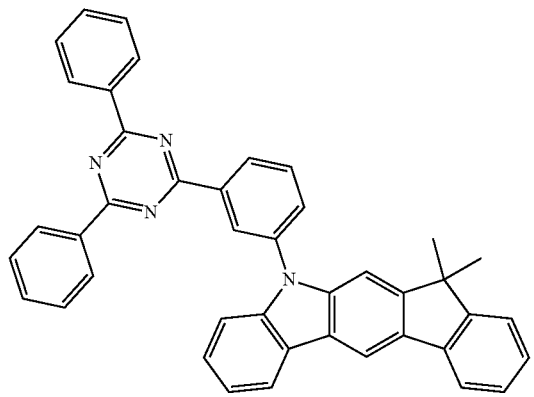
C.EX.6
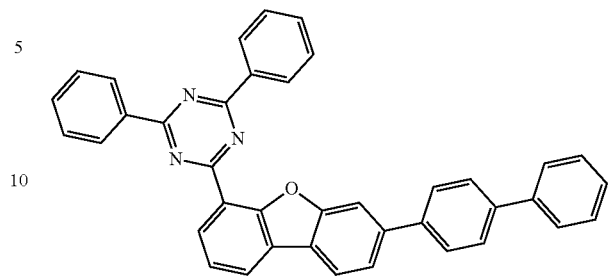
C.EX.3
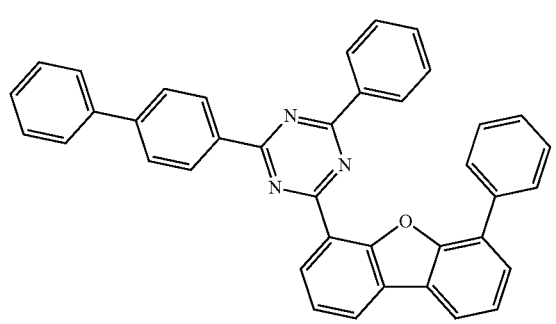
C.EX.7
C.EX.4
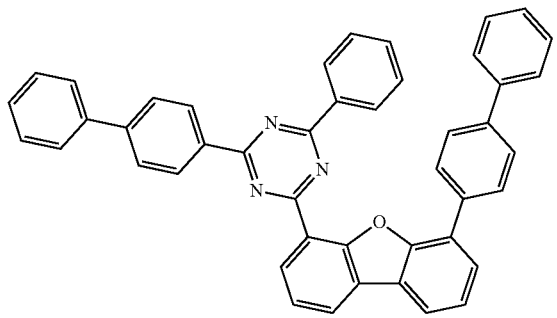
C.EX.5
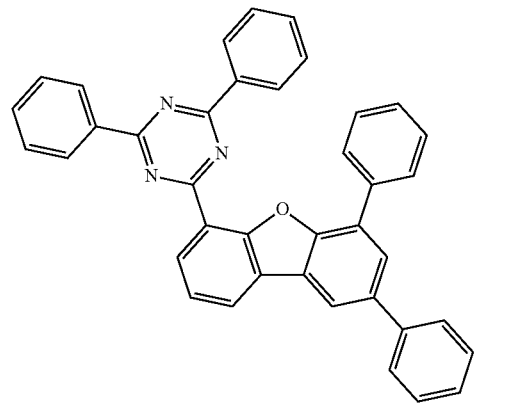
C.EX.8
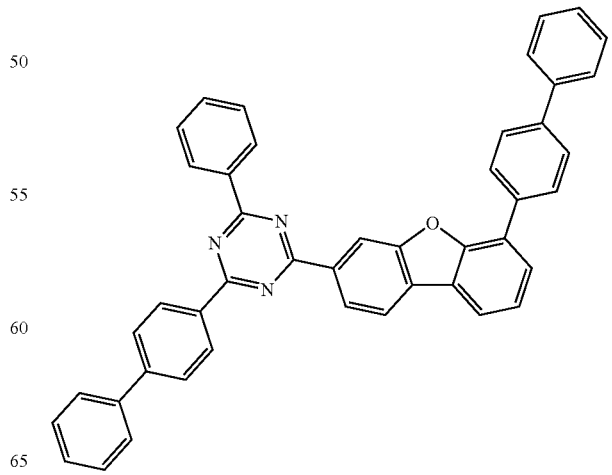

-continued
C.EX.9
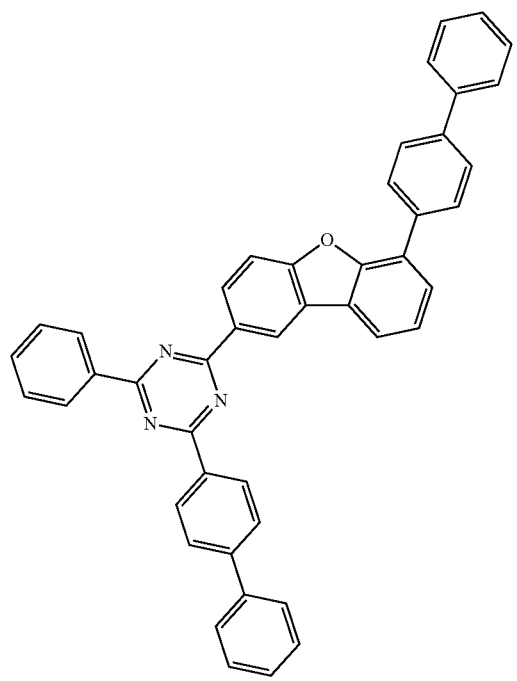
C.EX.10
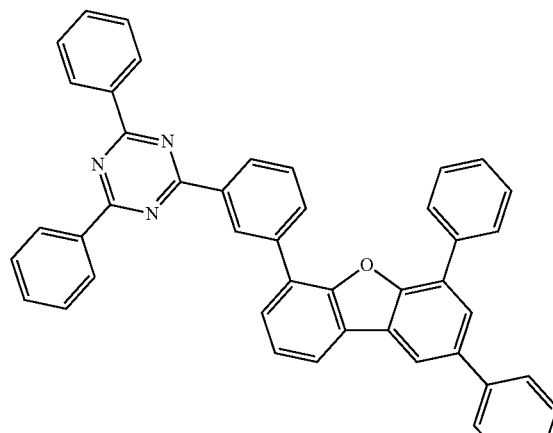
C.EX.11
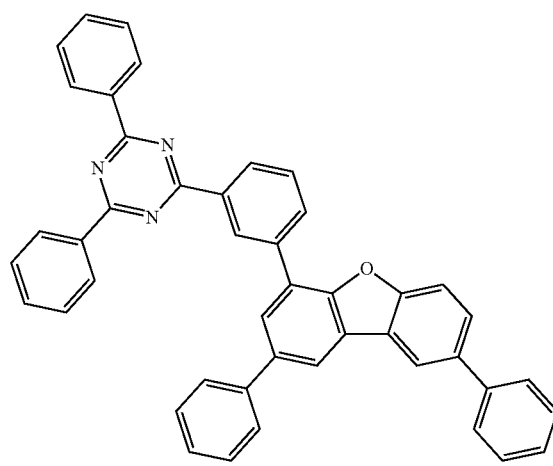
-continued
C.EX.12
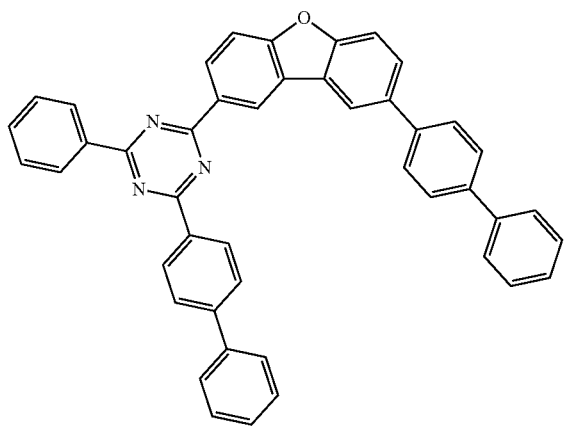
C.EX.13
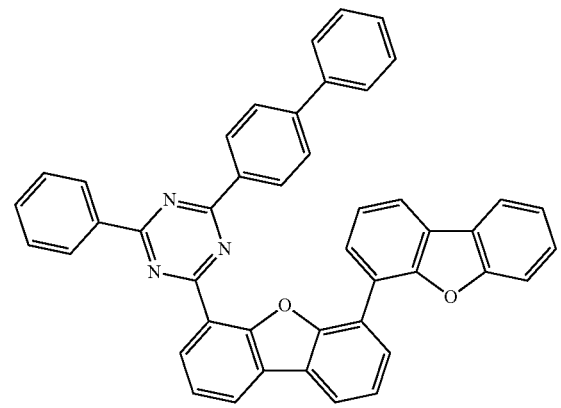
C.EX.14
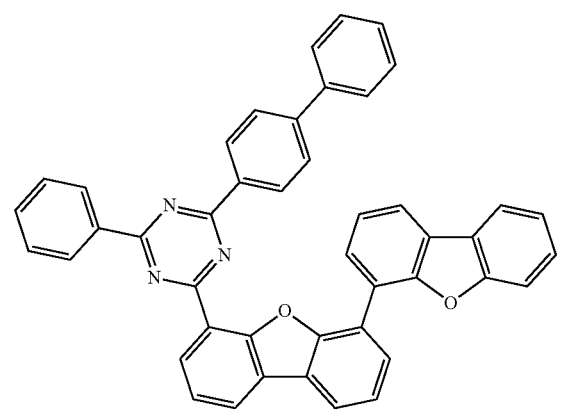

-continued
C.EX.15
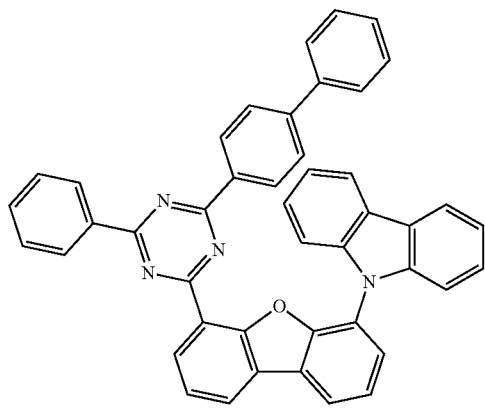
C.EX.16
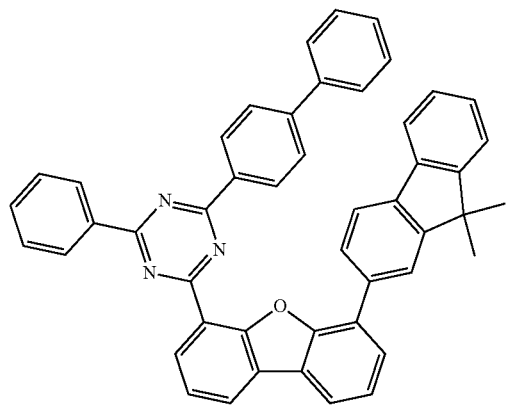
C.EX.17
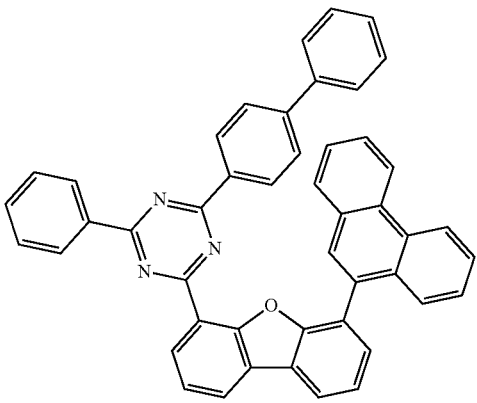
-continued
C.EX.18
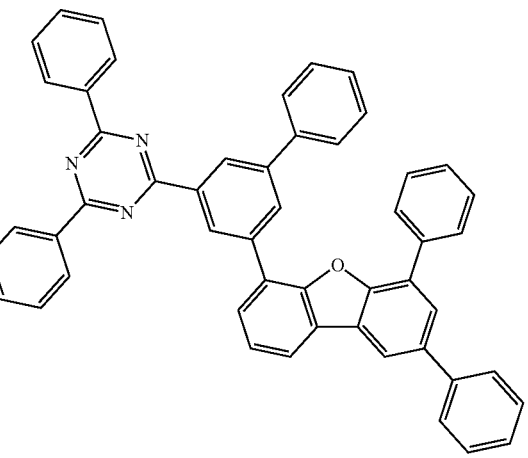
C.EX.19
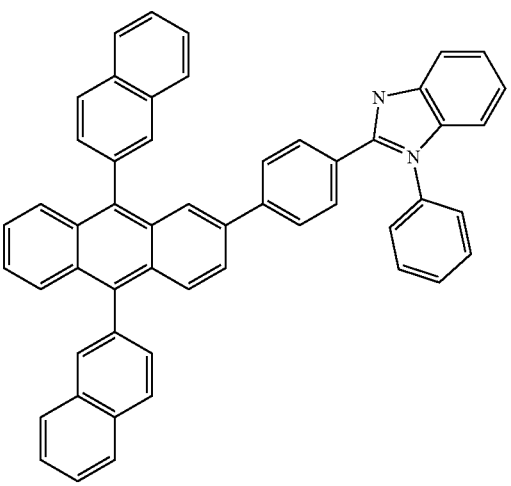
C.EX.20
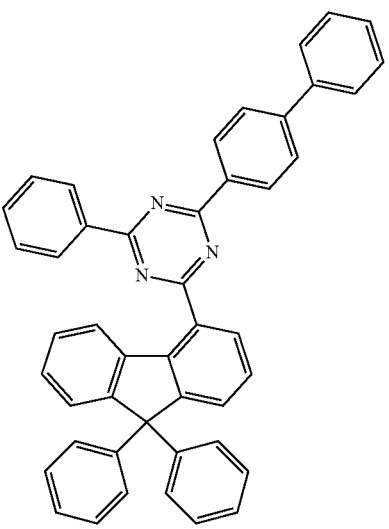

Experimental Example 1: Preparation of Organic Emitting Device

Experimental Example 1-1

A glass substrate on which a thin film of ITO (indium tin oxide) was coated in a thickness of 1,300 Å was put into distilled water containing the detergent dissolved therein and washed by the ultrasonic wave. The detergent used herein was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound of HI-1 as described below was thermally deposited under vacuum to a thicknesses of 50 Å to form the hole injection layer. On the hole injection layer, the compound of HT-1 was thermally deposited under vacuum to a thicknesses of 250 Å to form a hole transport layer, and a compound of HT-2 was deposited under vacuum to a thickness of 50 Å on the HT-1 vapor deposited layer to form an electron blocking layer.

On the HT-2 vapor deposited layer, the compound of Example 1 and a phosphorescent dopant YGD-1 were co-deposited at the weight ratio of 88:12 to form a light emitting layer having a thickness of 400 Å.

On the light emitting layer, a material of ET-1 was deposited under vacuum to a thickness of 250 Å, and additionally a material of ET-2 was co-deposited with 2% by weight of Li to a thickness of 100 Å to form an electron transport layer and an electron injection layer. Aluminum was deposited on the electron injection layer to a thickness of 1000 Å to form a cathode.

In the above process, the vapor deposition rate of the organic material was maintained at 0.4 to 0.7 Å/sec, the deposition rate of aluminum was maintained at 2 Å/sec, and the degree of vacuum during vapor deposition was maintained at $1\times10^{-7} \sim 5\times10^{-8}$ torr.

HI-1

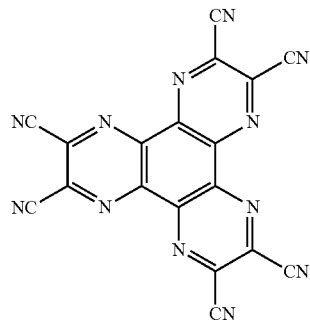

HT-1

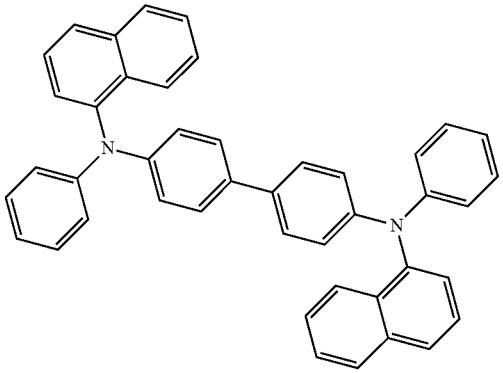

HT-2

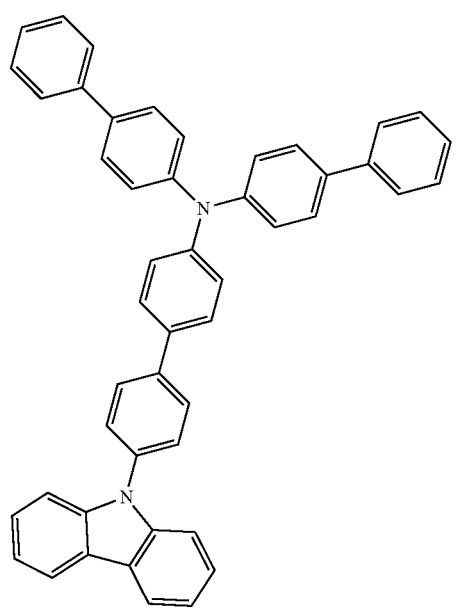

YGD-1

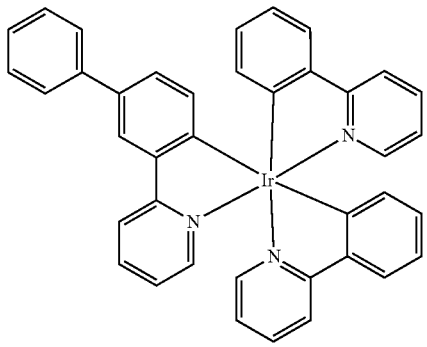

YGH-1

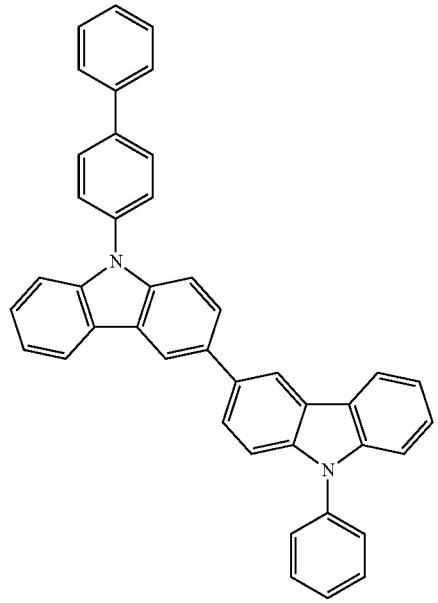

ET-1

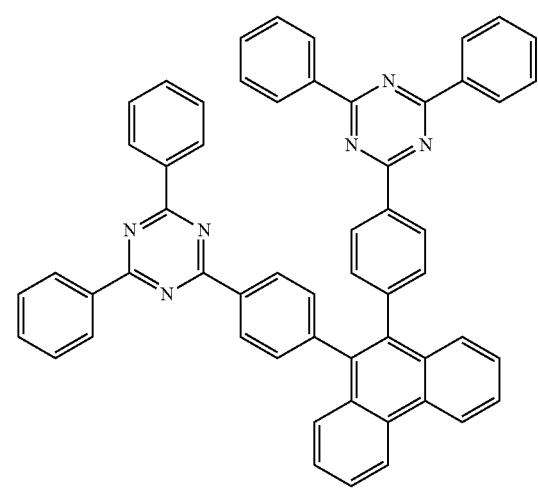

ET-2

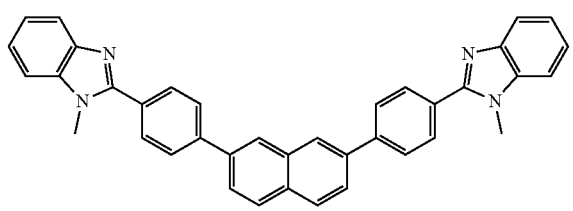

Experimental Examples 1-2 to 1-26

An organic light emitting device was fabricated in the same manner as in Experimental Example 1-1, except that the compound described in Table 1 below was used instead of the compound of Example 1 in Experimental Example 1.

Experimental Examples 1-27

An organic light emitting device was fabricated in the same manner as in Experimental Example 1-1, except that the compound of Example 1, the compound of YGH-1 and the dopant of YGD-1 were co-deposited at the weight of 44:44:12 to form a light emitting layer having a thickness of 400 Å.

Experimental Examples 1-28 to 1-52

An organic light emitting device was fabricated in the same manner as in Experimental Example 1-27, except that the compound described in Table 1 below was used instead of the compound of Example 1 in Experimental Example 1-27.

Comparative Experimental Examples 1-1 to 1-18

An organic light emitting device was fabricated in the same manner as in Experimental Example 1-1, except that the compound described in Table 2 below was used instead of the compound of Example 1 in Experimental Example 1-1.

Comparative Experimental Examples 1-19 to 1-36

An organic light emitting device was fabricated in the same manner as in Experimental Example 1-27, except that the compound described in Table 2 below was used instead of the compound of Example 1 in Experimental Example 1-27.

The driving voltage and the luminous efficiency of the organic light emitting devices fabricated in Experimental Examples 1-1 to 1-52 and Comparative Experimental Examples 1-1 to 1-36 were measured at a current density of 10 mA/cm². The time (LT95) taken to reach 95% relative to the initial luminance at the current density of 50 mA/cm² was measured. The results are shown in Tables 1 and 2 below.

TABLE 1

| Experimental Example No. | Compound | Voltage (V) (@ 10 mA/cm²) | Efficiency (Cd/A) (@ 10 mA/cm²) | Color coordinate (x, y) | Lifetime (h) T95 at 50 mA/cm² |
|---|---|---|---|---|---|
| 1-1 | Example 1 | 3.5 | 66 | 0.46, 0.53 | 101 |
| 1-2 | Example 2 | 3.4 | 73 | 0.46, 0.52 | 71 |
| 1-3 | Example 3 | 3.4 | 75 | 0.46, 0.53 | 72 |
| 1-4 | Example 4 | 3.4 | 80 | 0.47, 0.52 | 84 |
| 1-5 | Example 5 | 3.5 | 74 | 0.46, 0.52 | 91 |
| 1-6 | Example 6 | 3.7 | 64 | 0.46, 0.54 | 70 |

TABLE 1-continued

| Experimental Example No. | Compound | Voltage (V) (@ 10 mA/cm$^2$) | Efficiency (Cd/A) (@ 10 mA/cm$^2$) | Color coordinate (x, y) | Lifetime (h) T95 at 50 mA/cm$^2$ |
|---|---|---|---|---|---|
| 1-7 | Example 7 | 3.6 | 60 | 0.46, 0.53 | 80 |
| 1-8 | Example 8 | 3.7 | 74 | 0.46, 0.54 | 85 |
| 1-9 | Example 9 | 3.5 | 72 | 0.46, 0.52 | 67 |
| 1-10 | Example 10 | 3.5 | 73 | 0.46, 0.53 | 71 |
| 1-11 | Example 11 | 3.6 | 58 | 0.46, 0.53 | 70 |
| 1-12 | Example 12 | 3.4 | 70 | 0.46, 0.52 | 71 |
| 1-13 | Example 13 | 3.5 | 72 | 0.46, 0.53 | 72 |
| 1-14 | Example 14 | 3.6 | 70 | 0.46, 0.53 | 64 |
| 1-15 | Example 15 | 3.5 | 72 | 0.46, 0.53 | 60 |
| 1-16 | Example 16 | 3.5 | 67 | 0.44, 0.55 | 65 |
| 1-17 | Example 17 | 3.8 | 70 | 0.46, 0.52 | 71 |
| 1-18 | Example 18 | 3.7 | 70 | 0.46, 0.53 | 74 |
| 1-19 | Example 19 | 3.9 | 72 | 0.46, 0.54 | 60 |
| 1-20 | Example 20 | 3.5 | 67 | 0.46, 0.52 | 66 |
| 1-21 | Example 21 | 3.5 | 67 | 0.46, 0.52 | 65 |
| 1-22 | Example 22 | 3.5 | 67 | 0.46, 0.52 | 66 |
| 1-23 | Example 23 | 3.7 | 64 | 0.46, 0.54 | 67 |
| 1-24 | Example 24 | 3.5 | 67 | 0.44, 0.55 | 69 |
| 1-25 | Example 25 | 3.7 | 74 | 0.46, 0.54 | 65 |
| 1-26 | Example 27 | 3.6 | 70 | 0.46, 0.53 | 64 |

TABLE 2

| Experimental Example No. | Compound | Voltage (V) (@ 10 mA/cm$^2$) | Efficiency (Cd/A) (@ 10 mA/cm$^2$) | Color coordinate (x, y) | Lifetime (h) T95 at 50 mA/cm$^2$ |
|---|---|---|---|---|---|
| 1-27 | Example 1 | 3.8 | 73 | 0.46, 0.54 | 294 |
| 1-28 | Example 2 | 3.7 | 75 | 0.46, 0.54 | 121 |
| 1-29 | Example 3 | 3.6 | 80 | 0.46, 0.53 | 183 |
| 1-30 | Example 4 | 3.9 | 74 | 0.46, 0.53 | 160 |
| 1-31 | Example 5 | 4.0 | 60 | 0.46, 0.52 | 321 |
| 1-32 | Example 6 | 3.9 | 74 | 0.46, 0.54 | 202 |
| 1-33 | Example 7 | 3.8 | 68 | 0.46, 0.53 | 211 |
| 1-34 | Example 8 | 4.0 | 70 | 0.46, 0.52 | 217 |
| 1-35 | Example 9 | 3.8 | 72 | 0.46, 0.53 | 197 |
| 1-36 | Example 10 | 3.7 | 73 | 0.46, 0.54 | 241 |
| 1-37 | Example 11 | 3.7 | 66 | 0.46, 0.53 | 172 |
| 1-38 | Example 12 | 3.6 | 78 | 0.46, 0.54 | 145 |
| 1-39 | Example 13 | 3.6 | 74 | 0.46, 0.54 | 132 |
| 1-40 | Example 14 | 3.7 | 77 | 0.46, 0.53 | 141 |
| 1-41 | Example 15 | 3.7 | 80 | 0.46, 0.53 | 183 |
| 1-42 | Example 16 | 3.8 | 76 | 0.45, 0.54 | 212 |
| 1-43 | Example 17 | 4.2 | 60 | 0.46, 0.54 | 290 |
| 1-44 | Example 18 | 4.0 | 70 | 0.46, 0.54 | 248 |
| 1-45 | Example 19 | 3.8 | 71 | 0.46, 0.53 | 160 |
| 1-46 | Example 20 | 3.8 | 76 | 0.46, 0.53 | 190 |
| 1-47 | Example 21 | 3.8 | 76 | 0.46, 0.52 | 195 |
| 1-48 | Example 22 | 3.8 | 76 | 0.46, 0.54 | 199 |
| 1-49 | Example 23 | 3.9 | 74 | 0.46, 0.53 | 218 |
| 1-50 | Example 24 | 3.7 | 66 | 0.46, 0.52 | 175 |
| 1-51 | Example 25 | 3.7 | 73 | 0.46, 0.53 | 200 |
| 1-52 | Example 27 | 3.8 | 70 | 0.46, 0.54 | 125 |

TABLE 3

| Comparative Experimental Example No. | Compound | Voltage (V) (@ 10 mA/cm$^2$) | Efficiency (Cd/A) (@ 10 mA/cm$^2$) | Color coordinate (x, y) | Lifetime (h) T95 at 50 mA/cm$^2$ |
|---|---|---|---|---|---|
| 1-1 | Comparative Example 1 | 3.3 | 67 | 0.46, 0.54 | 40 |
| 1-2 | Comparative Example 2 | 3.0 | 60 | 0.46, 0.53 | 30 |
| 1-3 | Comparative Example 3 | 3.3 | 72 | 0.46, 0.54 | 23 |
| 1-4 | Comparative Example 4 | 3.3 | 73 | 0.46, 0.54 | 31 |

TABLE 3-continued

| Comparative Experimental Example No. | Compound | Voltage (V) (@ 10 mA/cm²) | Efficiency (Cd/A) (@ 10 mA/cm²) | Color coordinate (x, y) | Lifetime (h) T95 at 50 mA/cm² |
|---|---|---|---|---|---|
| 1-5 | Comparative Example 5 | 3.2 | 74 | 0.46, 0.53 | 44 |
| 1-6 | Comparative Example 6 | 3.2 | 72 | 0.46, 0.54 | 24 |
| 1-7 | Comparative Example 7 | 3.3 | 73 | 0.46, 0.52 | 32 |
| 1-8 | Comparative Example 8 | 3.4 | 74 | 0.46, 0.53 | 22 |
| 1-9 | Comparative Example 9 | 3.2 | 72 | 0.46, 0.54 | 21 |
| 1-10 | Comparative Example 10 | 3.1 | 73 | 0.46, 0.53 | 42 |
| 1-11 | Comparative Example 11 | 3.3 | 69 | 0.46, 0.52 | 47 |
| 1-12 | Comparative Example 12 | 3.3 | 64 | 0.46, 0.53 | 21 |
| 1-13 | Comparative Example 13 | 3.4 | 69 | 0.46, 0.54 | 32 |
| 1-14 | Comparative Example 14 | 3.1 | 72 | 0.46, 0.53 | 31 |
| 1-15 | Comparative Example 15 | 3.1 | 73 | 0.46, 0.54 | 41 |
| 1-16 | Comparative Example 16 | 3.3 | 73 | 0.46, 0.54 | 32 |
| 1-17 | Comparative Example 17 | 3.0 | 70 | 0.46, 0.53 | 23 |
| 1-18 | Comparative Example 18 | 3.2 | 69 | 0.46, 0.53 | 21 |
| 1-19 | Comparative Example 19 | 3.6 | 74 | 0.45, 0.54 | 111 |
| 1-20 | Comparative Example 20 | 3.5 | 68 | 0.45, 0.54 | 90 |
| 1-21 | Comparative Example 21 | 4.2 | 70 | 0.46, 0.54 | 77 |
| 1-22 | Comparative Example 22 | 4.0 | 72 | 0.46, 0.53 | 97 |
| 1-23 | Comparative Example 23 | 4.0 | 73 | 0.46, 0.54 | 95 |
| 1-24 | Comparative Example 24 | 3.8 | 74 | 0.46, 0.54 | 60 |
| 1-25 | Comparative Example 25 | 3.7 | 60 | 0.46, 0.53 | 92 |
| 1-26 | Comparative Example 26 | 3.8 | 74 | 0.46, 0.54 | 71 |
| 1-27 | Comparative Example 27 | 3.8 | 68 | 0.46, 0.52 | 61 |
| 1-28 | Comparative Example 28 | 3.7 | 70 | 0.46, 0.53 | 81 |
| 1-29 | Comparative Example 29 | 4.0 | 72 | 0.46, 0.54 | 82 |
| 1-30 | Comparative Example 30 | 3.8 | 73 | 0.46, 0.53 | 75 |
| 1-31 | Comparative Example 31 | 3.7 | 66 | 0.46, 0.52 | 75 |
| 1-32 | Comparative Example 32 | 3.7 | 71 | 0.46, 0.53 | 71 |
| 1-33 | Comparative Example 33 | 3.7 | 74 | 0.46, 0.54 | 11 |
| 1-34 | Comparative Example 34 | 3.8 | 71 | 0.46, 0.53 | 68 |
| 1-35 | Comparative Example 35 | 3.9 | 70 | 0.46, 0.53 | 61 |
| 1-36 | Comparative Example 36 | 3.8 | 65 | 0.45, 0.54 | 69 |

As shown in Tables 1 and 2 above, when the compound of the present invention was used as a light emitting layer, it exhibited excellent effects in terms of voltage, efficiency, and lifetime. In particular, when the compound of the present invention was used together with the compound of YGH1 (Experimental Examples 1-27 to 1-52), it was confirmed that the lifetime was remarkably improved.

In addition, it was confirmed that the compounds of Example 1 and Examples 2 to 4 exhibited a difference in lifetime depending on the substitution positions of dibenzofuran and that the lifetime was improved at a specific position. This tendency was confirmed even in the compounds of Examples 12 to 18. Further, when comparing Examples 1, 5, 8, 7, 8, 9, 10, 11, 18, and 19, it could be seen that they exhibited the difference in efficiency characteristics depending on the substituent types and substitution positions of R in the Chemical Formula 1, and that they were materials superior in terms of the efficiency, voltage and lifetime.

Further, when comparing Examples 8, 8, 10, and 18 with Examples 20 to 25, it could be seen that there was no significant difference in element voltage, efficiency, and lifetime characteristics depending on deuterium substitution.

On the other hand, when comparing Comparative Examples 3 to 5, it could be seen that they exhibited the difference in efficiency and lifetime depending on the number of R and the bond length of R, When comparing the Comparative Examples 6 to 12 and 18, it could be confirmed that the characteristics were also varied depending on this tendency and the difference in the state of bonding with the electron deficient group. Further, when comparing Comparative Examples 13 to 17, it was confirmed that even when one substituent was present, the efficiency, lifetime and the like were varied depending on the type of the substituent.

As described above, it was confirmed that the compounds of the present invention exhibited excellent properties in terms of efficiency and lifetime due to the difference in the number of substituents and the degree of bonding, as compared with the compounds of the Comparative Examples.

Experimental Example 2: Preparation of Organic Emitting Device

Experimental Example 2-1

A glass substrate on which a thin film of ITO (indium tin oxide) was coated in a thickness of 1,300 Å was put into distilled water containing the detergent dissolved therein and washed by the ultrasonic wave. The detergent used herein was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound of HI-1 as described below was thermally deposited under vacuum to a thicknesses of 50 Å to form the hole injection layer. On the hole injection layer, the compound of HT-1 was thermally deposited under vacuum to a thicknesses of 800 Å and a compound of HT-3 was sequentially vacuum-deposited thereon to a thickness of 500 Å to form a hole transport layer.

Then, on the hole transport layer, the compound of Example 1, GH1 and a phosphorescent dopant GD-1 were co-deposited at the weight ratio of 47.5:47.5:5 to form a light emitting layer having a thickness of 400 Å.

On the light emitting layer, a material of ET-3 was vacuum-deposited to a thickness of 50 Å to form a hole blocking layer. On the hole blocking layer, a material of ET-4 and LiQ were co-deposited at the weight ratio of 1:1 to form an electron transport layer having a thickness of 250 Å. On the electron transport layer, sequentially lithium fluoride (LiF) was deposited to a thickness of 10 Å, and aluminum was deposited thereon to a thickness of 1000 Å to form a cathode.

In the above process, the vapor deposition rate of the organic material was maintained at 0.4 to 0.7 Å/sec, the deposition rate of the lithium fluoride of the cathode was maintained at 0.3 Å/sec and that of aluminum was maintained at 2 Å/sec, and the degree of vacuum during vapor deposition was maintained at $1 \times 10^{-7} \sim 5 \times 10^{-8}$ torr.

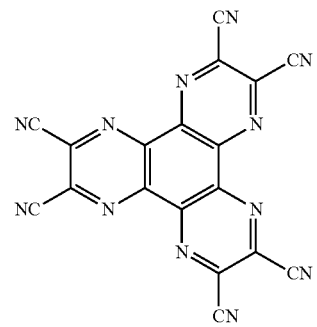

HI-1

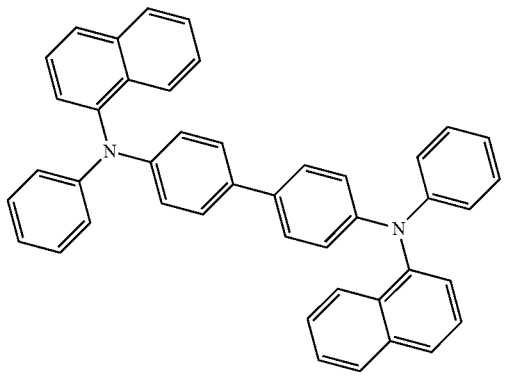

HT-1

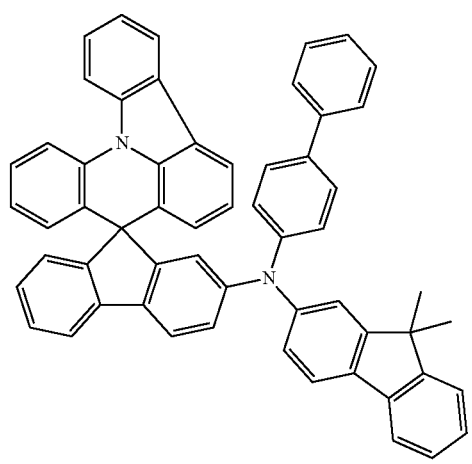

HT-3

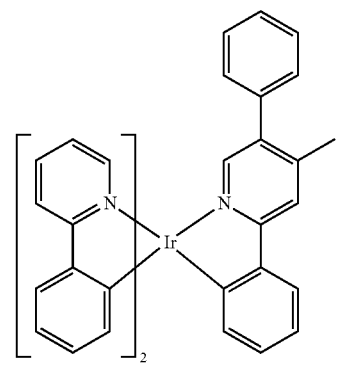

GD-1

GH-1

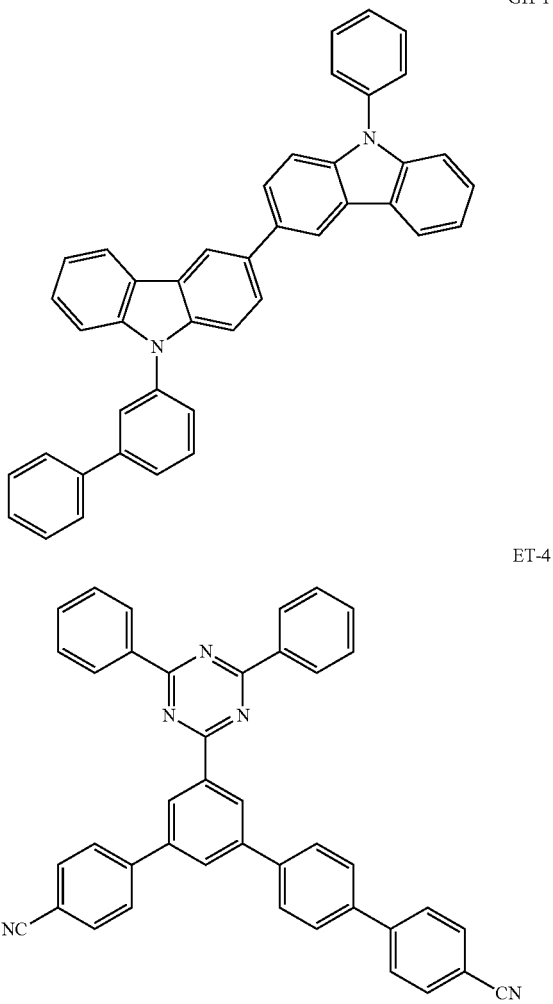

ET-4

ET-3

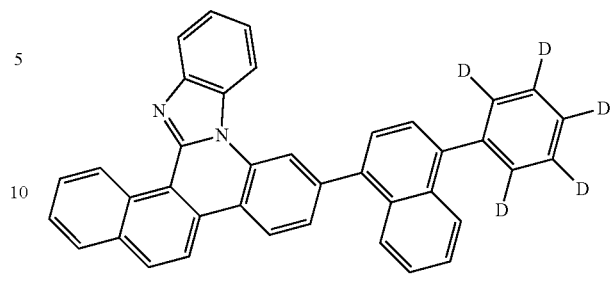

Experimental Examples 2-2 to 2-26

An organic light emitting device was fabricated in the same manner as in Experimental Example 2-1, except that the compound described in Table 4 below was used instead of the compound of Example 1 in Experimental Example 2-1.

Comparative Experimental Examples 2-1 to 2-9

An organic light emitting device was fabricated in the same manner as in Experimental Example 2-1, except that the compound described in Table 5 below was used instead of the compound of Example 1 in Experimental Example 2-1.

The driving voltage and the luminous efficiency of the organic light emitting devices fabricated in Experimental Examples 2-1 to 2-26 and Comparative Experimental Examples 2-1 to 2-9 were measured at a current density of 10 mA/cm$^2$. The time (LT95) taken to reach 95% relative to the initial luminance at the current density of 50 mA/cm$^2$ was measured. The results are shown in Tables 4 and 5 below.

TABLE 4

| Experimental Example No. | Compound | Voltage (V) (@ 10 mA/cm$^2$) | Efficiency (Cd/A) (@ 10 mA/cm$^2$) | Color coordinate (x, y) | Lifetime (h) T95 at 50 mA/cm$^2$ |
|---|---|---|---|---|---|
| 2-1 | Example 1 | 4.4 | 64 | 0.34, 0.61 | 241 |
| 2-2 | Example 2 | 4.3 | 65 | 0.33, 0.63 | 155 |
| 2-3 | Example 3 | 4.2 | 66 | 0.34, 0.62 | 103 |
| 2-4 | Example 4 | 4.4 | 63 | 0.34, 0.63 | 181 |
| 2-5 | Example 5 | 4.8 | 50 | 0.37, 0.67 | 241 |
| 2-6 | Example 6 | 4.6 | 67 | 0.34, 0.61 | 191 |
| 2-7 | Example 7 | 4.4 | 59 | 0.34, 0.60 | 118 |
| 2-8 | Example 8 | 4.2 | 64 | 0.35, 0.61 | 101 |
| 2-9 | Example 9 | 4.3 | 65 | 0.34, 0.61 | 117 |
| 2-10 | Example 10 | 4.4 | 65 | 0.35, 0.62 | 197 |
| 2-11 | Example 11 | 4.3 | 61 | 0.33, 0.62 | 142 |
| 2-12 | Example 12 | 4.4 | 66 | 0.34, 0.62 | 129 |
| 2-13 | Example 13 | 4.3 | 67 | 0.33, 0.61 | 131 |
| 2-14 | Example 14 | 4.4 | 65 | 0.34, 0.62 | 133 |
| 2-15 | Example 15 | 4.3 | 64 | 0.31, 0.63 | 142 |
| 2-16 | Example 16 | 4.3 | 61 | 0.30, 0.64 | 160 |
| 2-17 | Example 17 | 4.4 | 62 | 0.33, 0.62 | 181 |
| 2-18 | Example 18 | 4.4 | 61 | 0.34, 0.63 | 197 |
| 2-19 | Example 19 | 4.5 | 63 | 0.34, 0.63 | 111 |
| 2-20 | Example 20 | 4.3 | 62 | 0.34, 0.63 | 138 |
| 2-21 | Example 21 | 4.3 | 61 | 0.34, 0.63 | 164 |
| 2-22 | Example 22 | 4.3 | 61 | 0.34, 0.63 | 170 |
| 2-23 | Example 23 | 4.6 | 65 | 0.34, 0.63 | 180 |
| 2-24 | Example 24 | 4.3 | 65 | 0.34, 0.63 | 140 |

TABLE 4-continued

| Experimental Example No. | Compound | Voltage (V) (@ 10 mA/cm²) | Efficiency (Cd/A) (@ 10 mA/cm²) | Color coordinate (x, y) | Lifetime (h) T95 at 50 mA/cm² |
|---|---|---|---|---|---|
| 2-25 | Example 25 | 4.2 | 64 | 0.34, 0.63 | 133 |
| 2-26 | Example 27 | 4.1 | 68 | 0.34, 0.63 | 134 |

TABLE 5

| Comparative Experimental No. | Compound | Voltage (V) (@ 10 mA/cm²) | Efficiency (Cd/A) (@ 10 mA/cm²) | Color coordinate (x, y) | Lifetime (h) T95 at 50 mA/cm² |
|---|---|---|---|---|---|
| 2-1 | Comparative Example 1 | 4.4 | 62 | 0.35, 0.62 | 99 |
| 2-2 | Comparative Example 2 | 4.2 | 55 | 0.35, 0.61 | 80 |
| 2-3 | Comparative Example 3 | 4.4 | 61 | 0.34, 0.63 | 28 |
| 2-4 | Comparative Example 4 | 4.3 | 60 | 0.34, 0.63 | 41 |
| 2-5 | Comparative Example 5 | 4.5 | 62 | 0.34, 0.63 | 57 |
| 2-6 | Comparative Example 10 | 4.3 | 60 | 0.34, 0.63 | 51 |
| 2-7 | Comparative Example 11 | 4.5 | 64 | 0.34, 0.63 | 33 |
| 2-8 | Comparative Example 13 | 4.4 | 61 | 0.34, 0.63 | 49 |
| 2-9 | Comparative Example 18 | 4.6 | 66 | 0.35, 0.62 | 30 |

As shown in Table 4 above, it could be seen that when the compounds of Examples 1 to 26 were used as materials of the light emitting layer, they exhibited excellent effects in terms of efficiency and stability similarly to those of Experimental Example 1, as compared with when the materials of Comparative Examples were used.

Experimental Example 3: Preparation of Organic Emitting Device

Experimental Example 3-1

A glass substrate on which a thin film of ITO (indium tin oxide) was coated in a thickness of 1,000 Å was put into distilled water containing a dispersant dissolved therein and washed by the ultrasonic wave. The detergent used herein was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was completed, the substrate was ultrasonically washed in the order of isopropyl alcohol, acetone, and methanol solvent, and dried, On the ITO transparent electrode thus prepared, a compound of HI-1 was thermally deposited under vacuum to a thicknesses of 500 Å to form the hole injection layer. On the hole injection layer, the compound of HT-1 was deposited under vacuum to a thicknesses of 400 Å to form a hole transport layer. As the light emitting layer, a material of H1 and a dopant D1 compound (2.5 wt %) was deposited under vacuum to a thickness of 300 Å. A compound of ET-A below was vacuum-deposited on the light emitting layer to a thickness of 50 Å to form an a-electron transport layer. On the a-electron transport layer, the compound of Example 1 and the LiQ (lithium fluoride) were vacuum-deposited at the weight ratio of 1:1 to form an electron injection and transport layer having a thickness of 350 Å. On the electron injection and transport layer, sequentially, lithium fluoride (LiF) was deposited to a thickness of 12 Å, and aluminum was deposited thereon to a thickness of 2000 Å to form a cathode.

In the above process, the vapor deposition rate of the organic material was maintained at 0.4 to 0.7 Å/sec, the deposition rate of the lithium fluoride of the cathode was maintained at 0.3 Å/sec and that of aluminum was maintained at 2 Å/sec, and the degree of vacuum during vapor deposition was maintained at $2 \times 10^{-7} \sim 5 \times 10^{-6}$ torr. Thereby, the light emitting device was prepared.

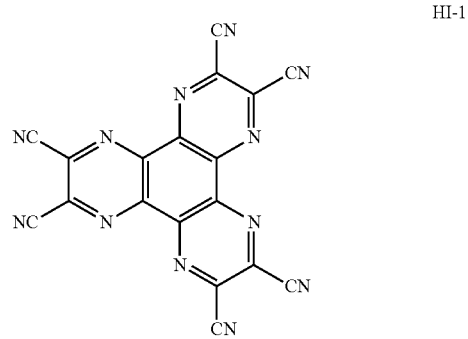

HI-1

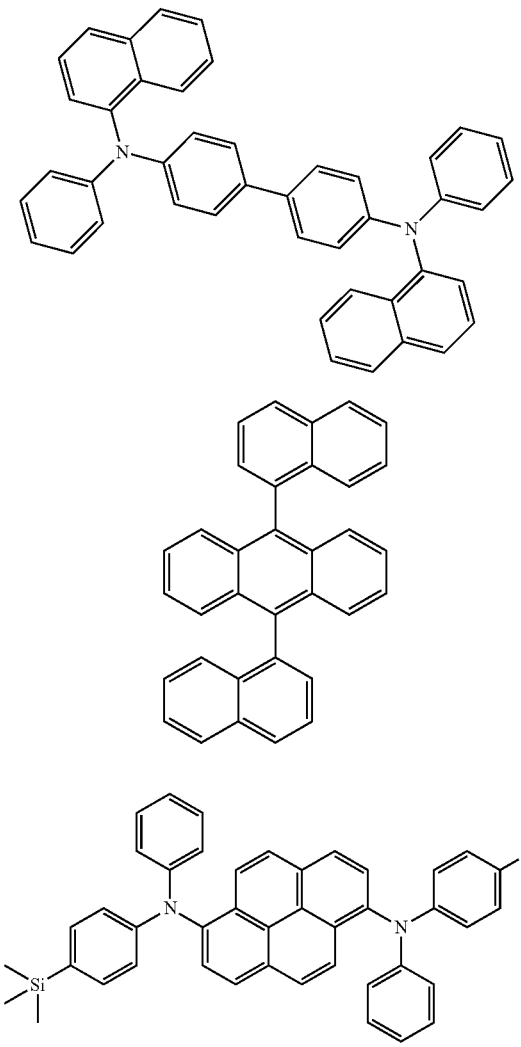

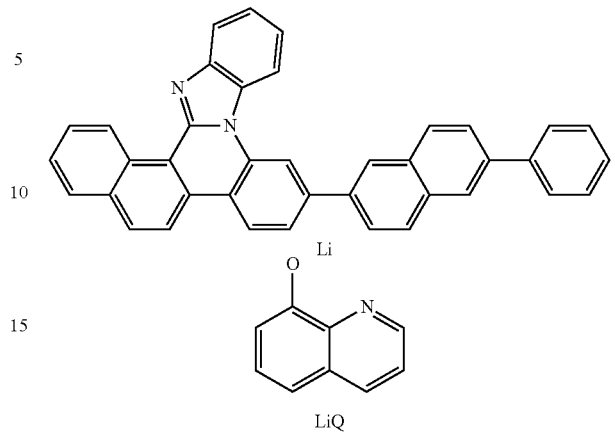

Experimental Examples 3-2 to 3-16

An organic light emitting device was fabricated in the same manner as in Experimental Example 3-1, except that the compound described in Table 6 below was used instead of the compound of Example 1 in Experimental Example 3-1.

Comparative Experimental Examples 3-1 and 3-2

An organic light emitting device was fabricated in the same manner as in Experimental Example 3-1, except that the compound described in Table 7 below was used instead of the compound of Example 1 in Experimental Example 3-1

The driving voltage and the luminous efficiency of the organic light emitting devices fabricated in Experimental Examples 3-1 to 3-16 and Comparative Experimental Examples 3-1 to 3-2 were measured at a current density of 10 mA/cm². The time (LT95) taken to reach 95% relative to the initial luminance at the current density of 50 mA/cm² was measured. The results are shown in Tables 6 and 7 below.

TABLE 6

| Experimental Example No. | Compound | Voltage (V) (@ 10 mA/cm²) | Efficiency (Cd/A) (@ 10 mA/cm²) | Color coordinate (x, y) | Lifetime (h) T95 at 50 mA/cm² |
|---|---|---|---|---|---|
| 3-1 | Example 1 | 4.31 | 4.95 | 0.134, 0.133 | 90 |
| 3-2 | Example 16 | 4.10 | 4.05 | 0.133, 0.133 | 80 |
| 3-3 | Example 17 | 3.99 | 4.95 | 0.134, 0.132 | 120 |
| 3-4 | Example 27 | 3.60 | 7.10 | 0.134, 0.132 | 75 |
| 3-5 | Example 28 | 3.64 | 7.22 | 0.134, 0.132 | 70 |
| 3-6 | Example 29 | 3.71 | 6.75 | 0.134, 0.133 | 70 |
| 3-7 | Example 30 | 3.70 | 7.10 | 0.133, 0.133 | 160 |
| 3-8 | Example 31 | 3.81 | 6.90 | 0.134, 0.132 | 140 |
| 3-9 | Example 32 | 3.87 | 6.75 | 0.134, 0.132 | 77 |
| 3-10 | Example 33 | 3.71 | 6.20 | 0.134, 0.132 | 190 |
| 3-11 | Example 34 | 3.70 | 6.48 | 0.134, 0.133 | 120 |
| 3-12 | Example 35 | 3.70 | 7.10 | 0.132, 0.134 | 75 |
| 3-13 | Example 36 | 3.60 | 7.20 | 0.133, 0.135 | 70 |
| 3-14 | Example 37 | 3.69 | 7.00 | 0.134, 0.133 | 75 |
| 3-15 | Example 38 | 3.72 | 6.87 | 0.134, 0.133 | 90 |
| 3-16 | Example 39 | 3.72 | 7.10 | 0.134, 0.133 | 73 |

TABLE 7

| Comparative Example No. | Compound | Voltage (V) (@ 10 mA/cm$^2$) | Efficiency (Cd/A) (@ 10 mA/cm$^2$) | Color coordinate (x, y) | Lifetime (h) T95 at 50 mA/cm$^2$ |
|---|---|---|---|---|---|
| 3-1 | Comparative Example 1 | 3.60 | 5.80 | 0.133, 0.133 | 50 |
| 3-2 | Comparative Example 2 | 3.90 | 6.81 | 0.134, 0.132 | 40 |

As shown in Tables 6 and 7 above, it could be seen that when the compounds of the present invention (Examples 1, 18 and 28-39) were used as materials of the electron transport layer, it was confirmed that they exhibited excellent effects in terms of stability as compared with when the materials of Comparative Examples 1 and 2 were used.

Experimental Example 4: Evaluation of Material Co-Deposition

Experimental Example 4-1

A preliminary mixture was prepared by using Example 18 and CoH1 compound at a weight ratio of 5:5, and then these were physically mixed, pulverized and then loaded in an evaporation source. The premixed composition was thermally co-evaporated at a rate of 2 Å/sec in a vacuum chamber under a pressure of less than 10$^{-7}$ torr and deposited on a glass substrate. While the evaporation and cooling of the source were not stopped, the substrate was successively replaced after deposition of a film having a thickness of 500 Å. The composition of the film was analyzed by high performance liquid chromatography (HPLC), and the results are shown in Table 8 below.

Experimental Examples 4-2 and 4-4

The experiment was carried out in the same manner as in Experimental Example 4-1, except that the compound described in Table 8 was used instead of the compound of Experimental Example 4-1 in Experimental Example 4-1.

TABLE 8

| Experimental Example No. | Compound | Component (%) Compound | CoH1 |
|---|---|---|---|
| Experimental Example 4-1 | Example 16 | 48.7 | 51.3 |
| Experimental Example 4-2 | Example 20 | 50.1 | 49.9 |
| Experimental Example 4-3 | Example 21 | 49.7 | 50.3 |
| Experimental Example 4-4 | Example 22 | 51.1 | 48.9 |

As shown in Table 8, the deposition rate of the composition could be varied upon co-deposition with deuterium.

EXPLANATION OF SIGN

1: substrate
2: anode
3: light emitting layer
4: cathode
5: hole injection layer
6: hole transport layer
7: light emitting layer
8: electron transport layer

The invention claimed is:
1. A compound represented by the following Chemical Formula 1, Chemical Formula 2, or Chemical Formula 3:

[Chemical Formula 1]

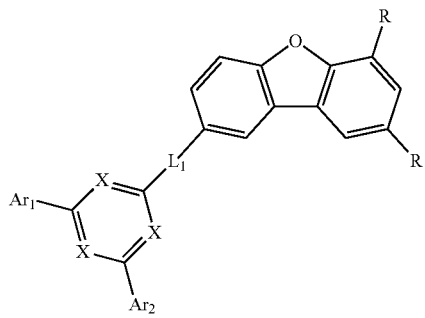

[Chemical Formula 2]

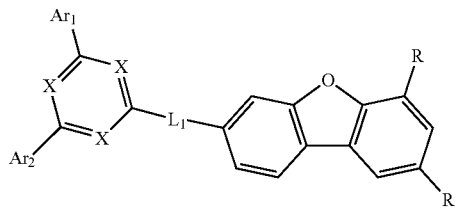

[Chemical Formula 3]

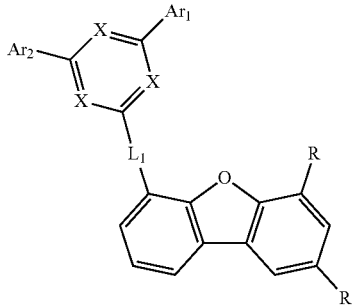

in Chemical Formulas 1 to 3,
X is each independently N or CH,
L$_1$ is a single bond; or a substituted or unsubstituted C$_{6-60}$ arylene,
Ar$_1$ and Ar$_2$ are each independently a substituted or unsubstituted C$_{6-60}$ aryl; or a substituted or unsubstituted C$_{2-60}$ heteroaryl containing at least one heteroatom selected from the group consisting of N, O, S and Si, and
each R is identical to each other and is phenyl substituted with cyano, biphenylyl unsubstituted or substituted with one to five deuterium, naphthyl, phenanthrenyl unsubstituted or substituted with one to five deuterium, benzofuranyl substituted with one to five deuterium, benzothiophenyl, carbazolyl, pyridinephenyl, 9,9-dimethyl-xanthenyl, or 9,9-dimethyl-thioxanthenyl.

2. The compound of claim 1, wherein each X is N.
3. The compound of claim 1, wherein $L_1$ is a single bond or phenylene.
4. The compound of claim 1, wherein $Ar_1$ and $Ar_2$ are each independently phenyl or biphenylyl.
5. The compound of claim 1, wherein the compound represented by Chemical Formula 1, 2 or 3 is selected from the following compounds:
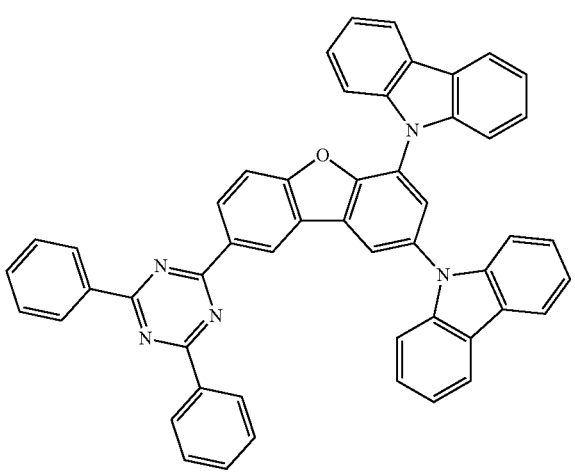
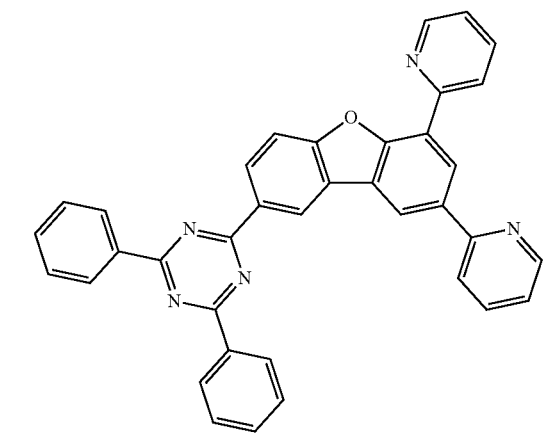
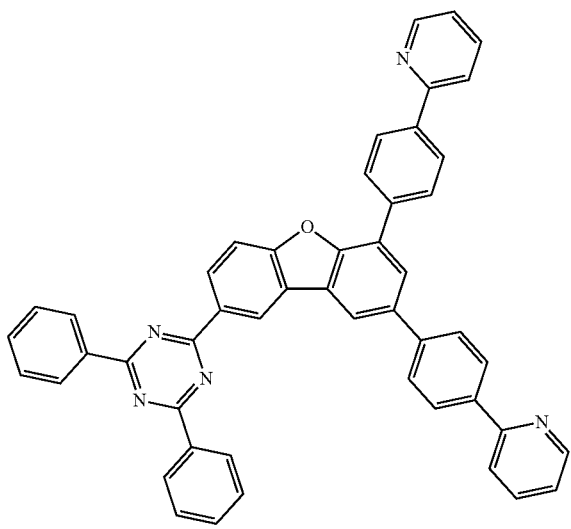
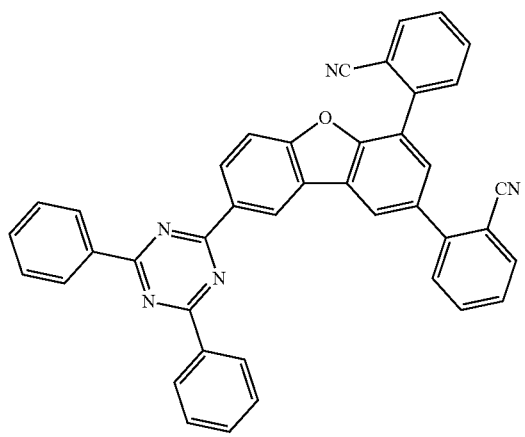
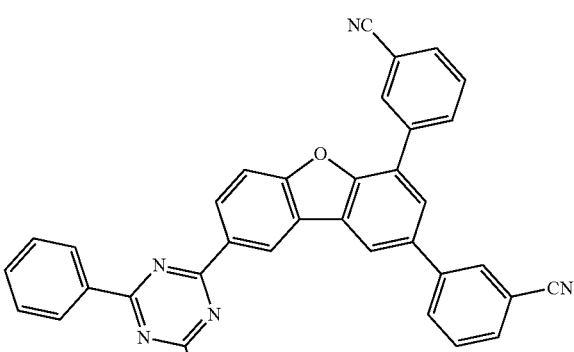
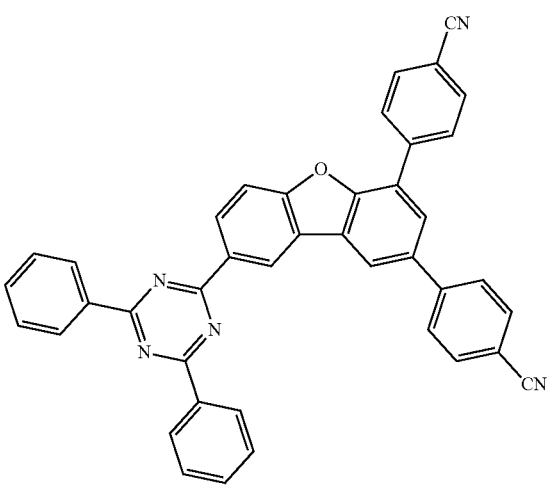

149
-continued
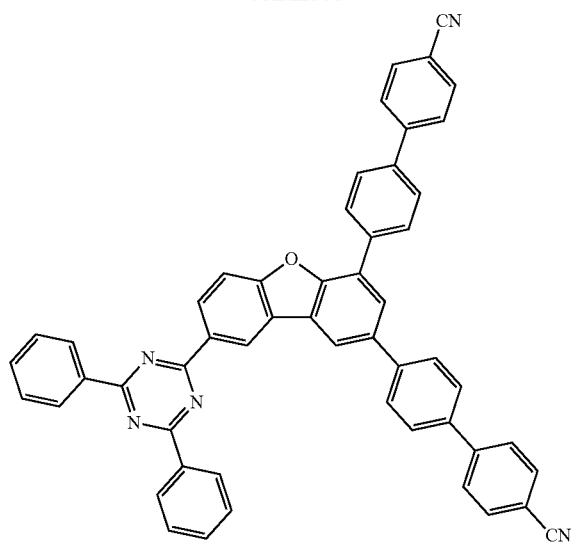
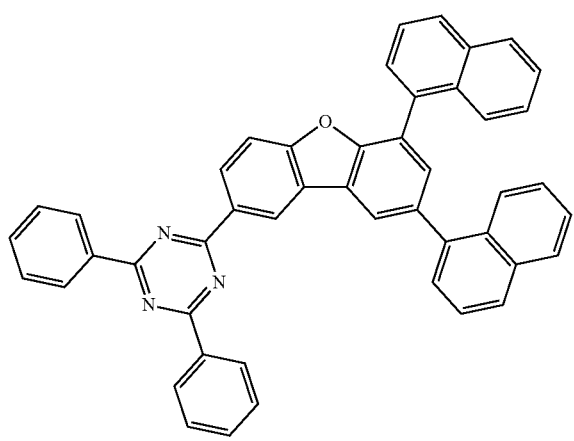
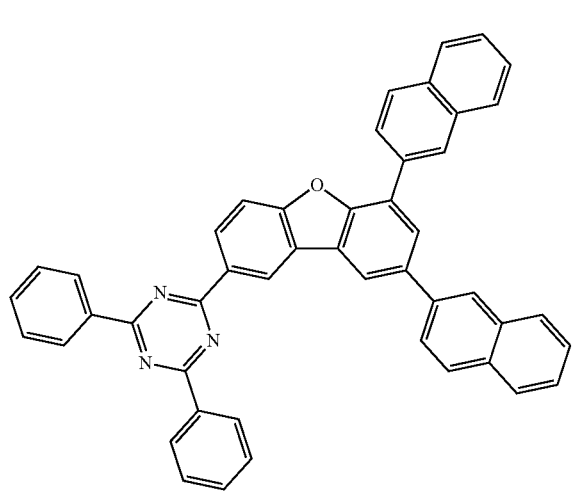
150
-continued
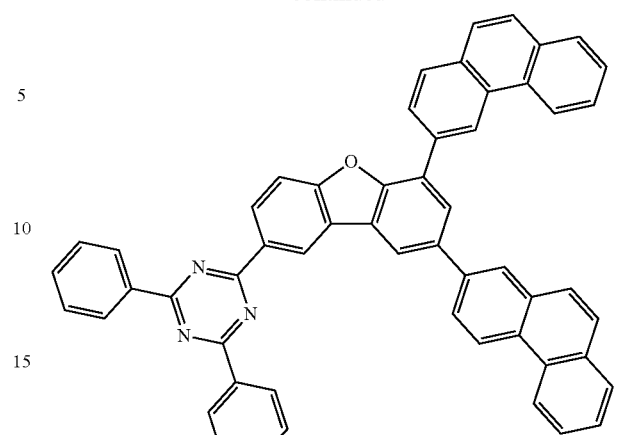
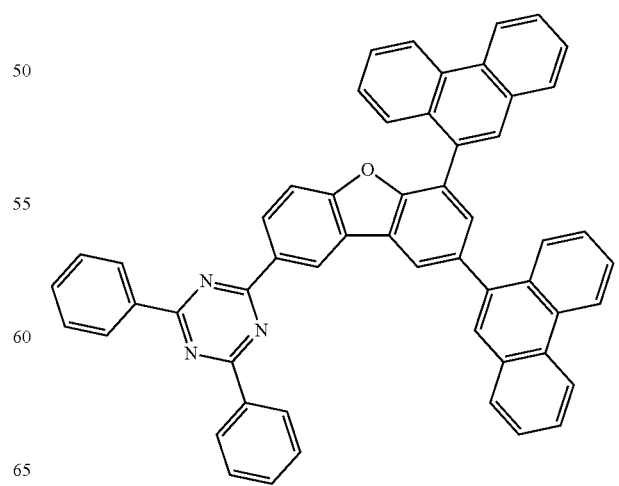

151
-continued
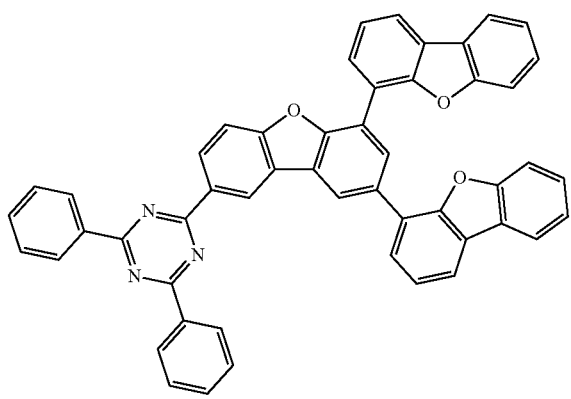
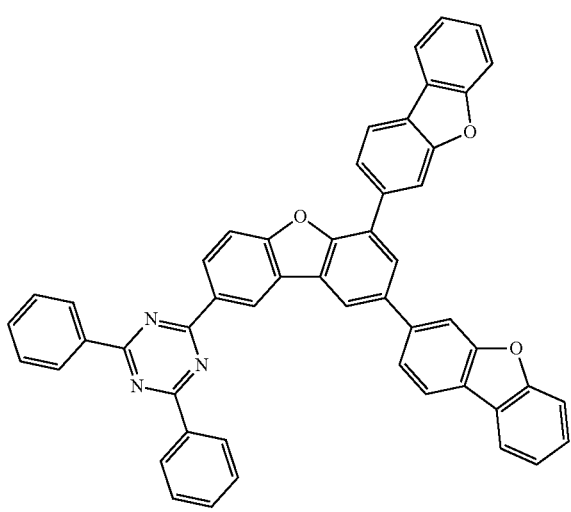
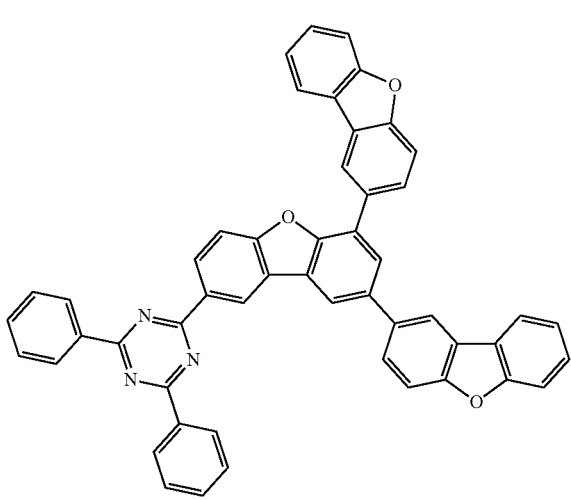
152
-continued
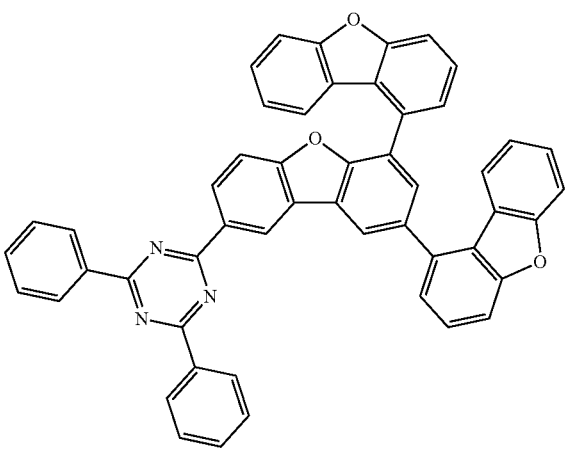
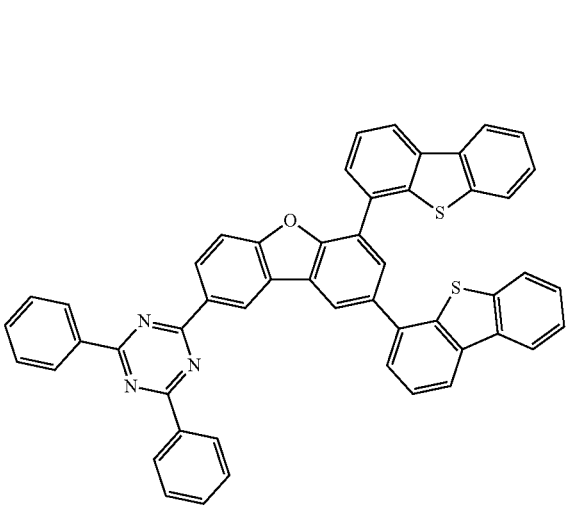

153
-continued
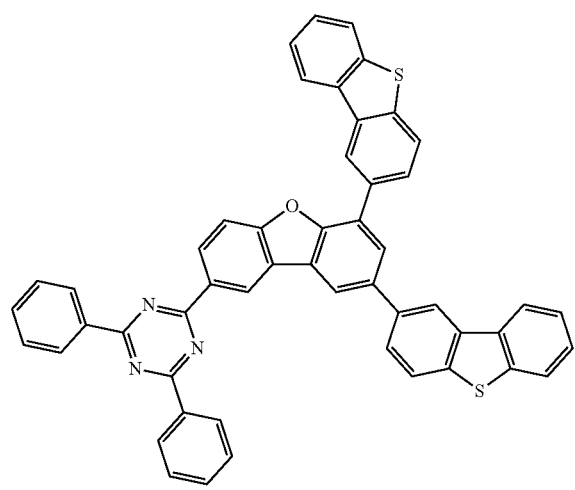
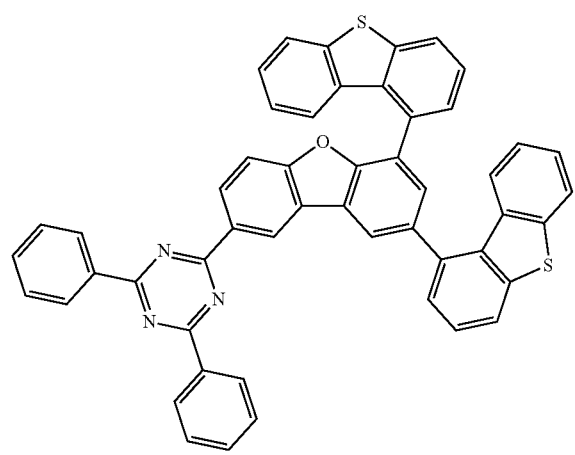
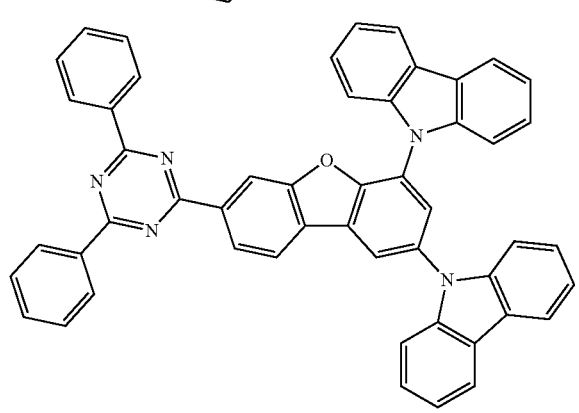
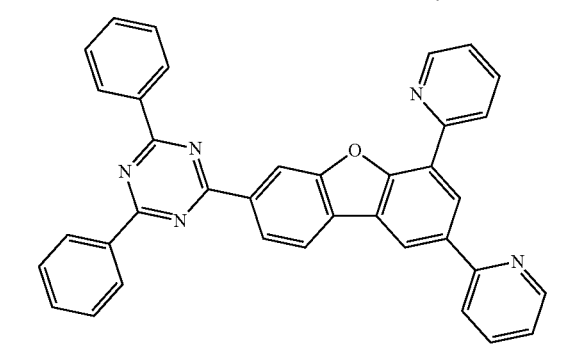
154
-continued
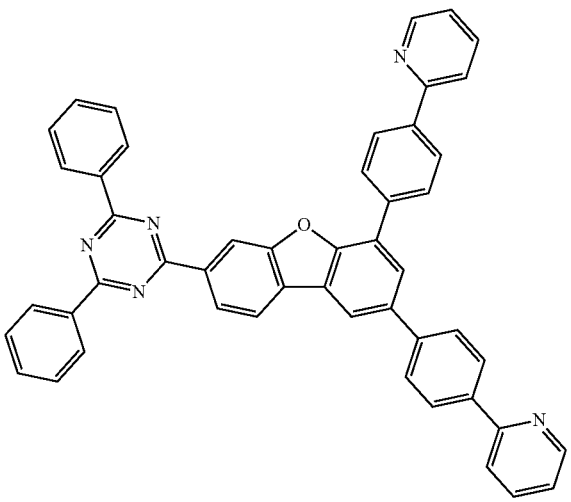
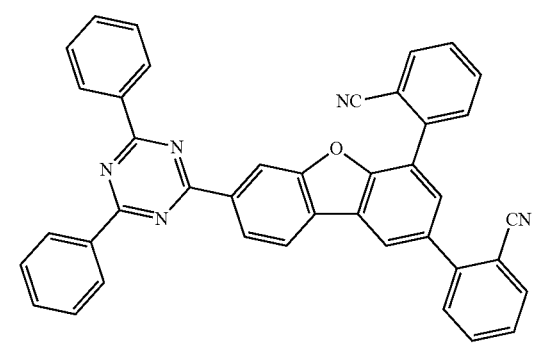
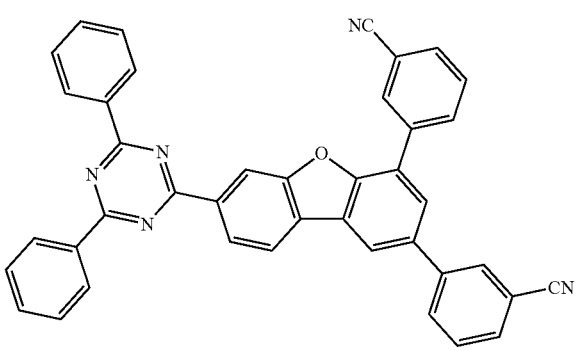
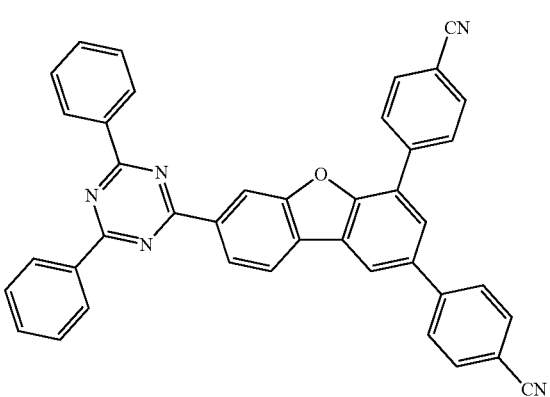

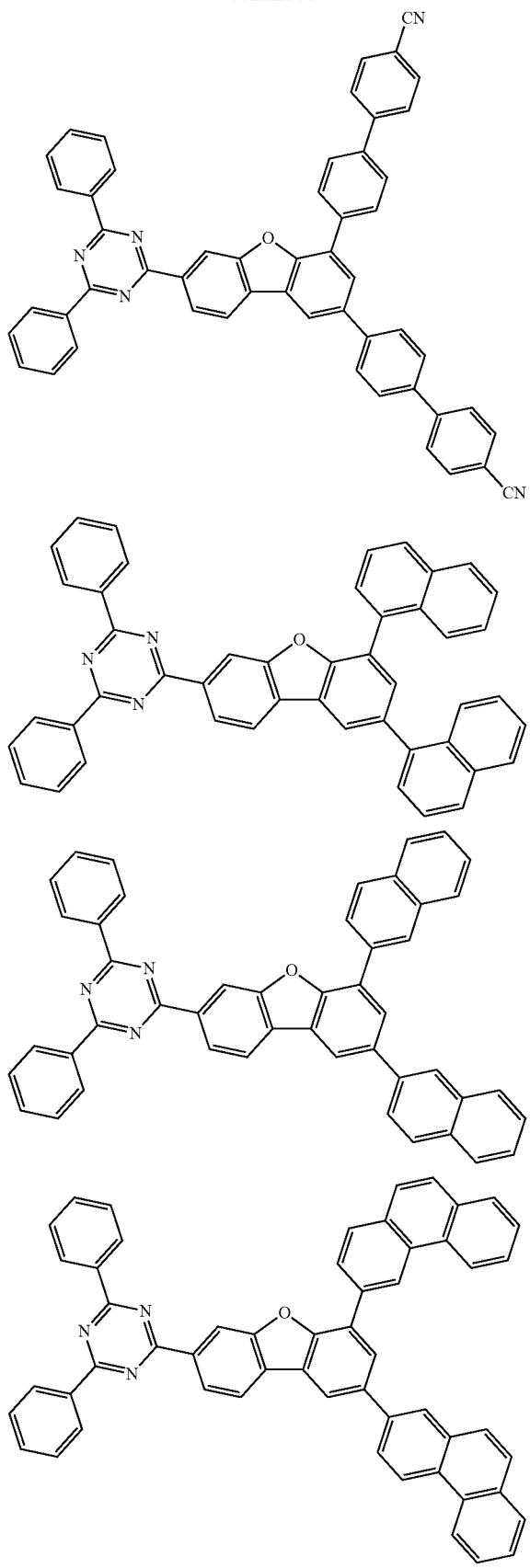
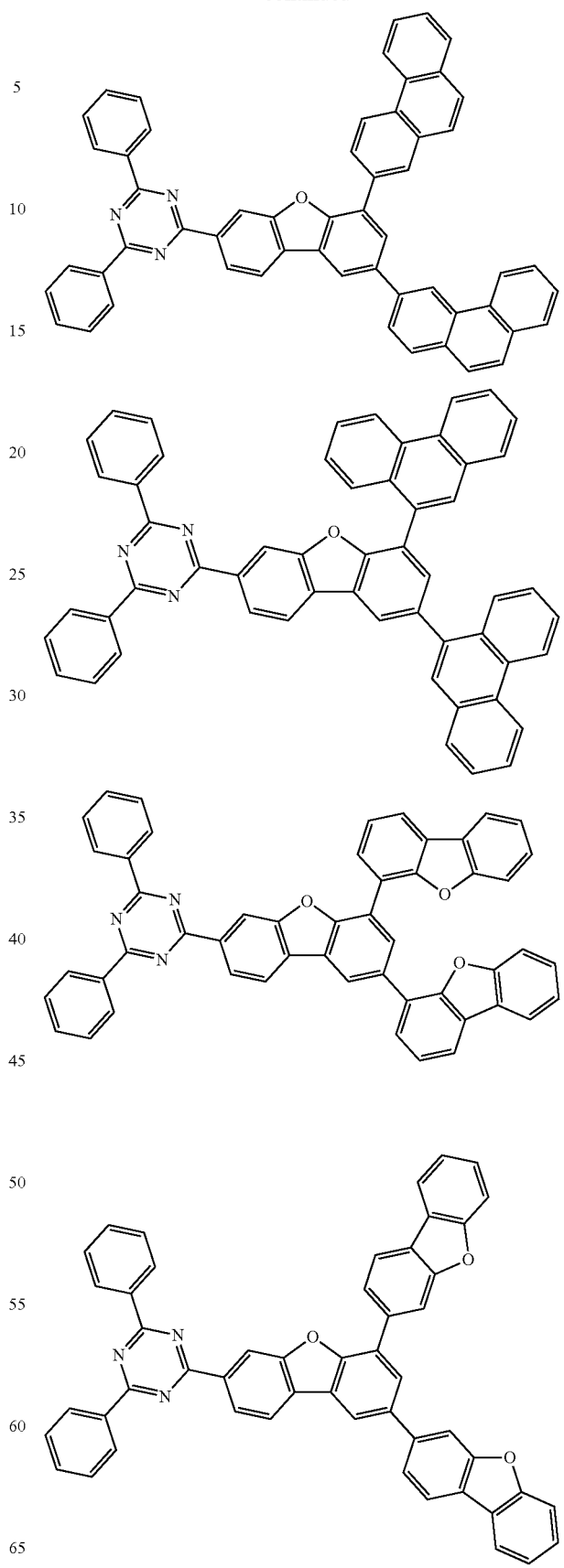

157
-continued
158
-continued
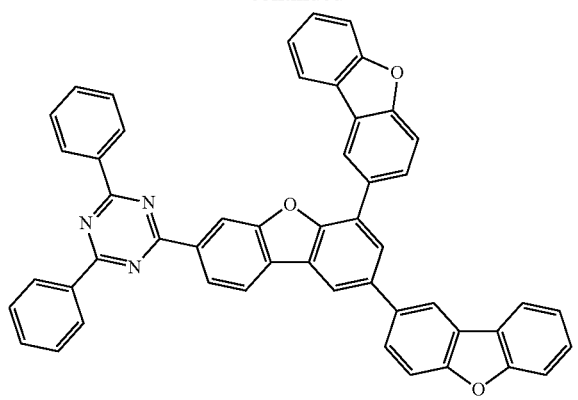
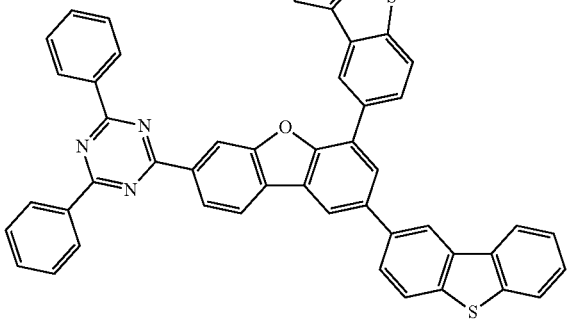
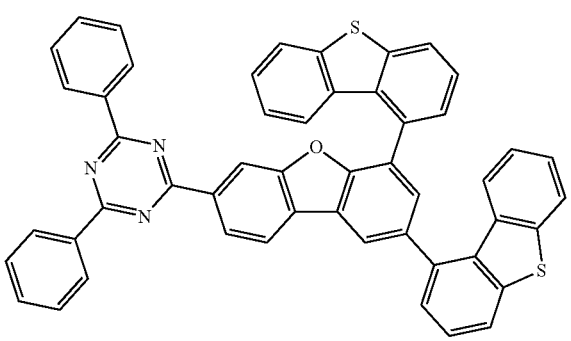
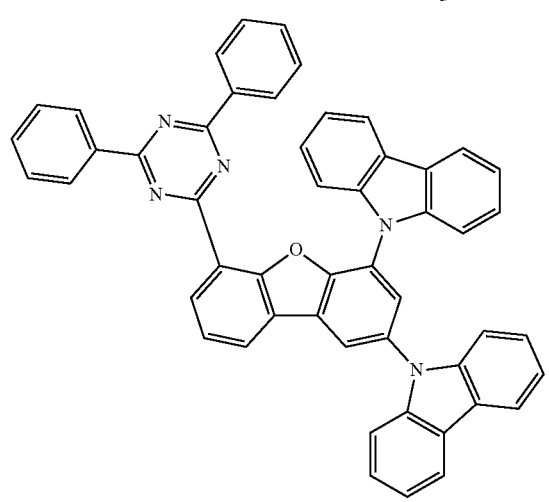
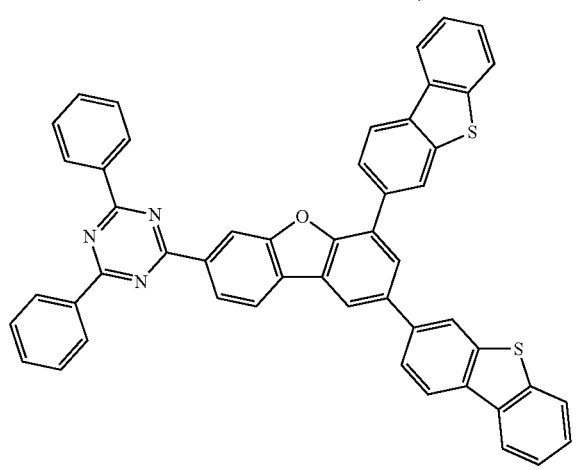
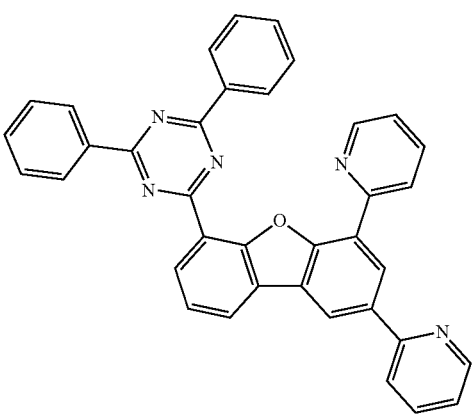

159
-continued
160
-continued
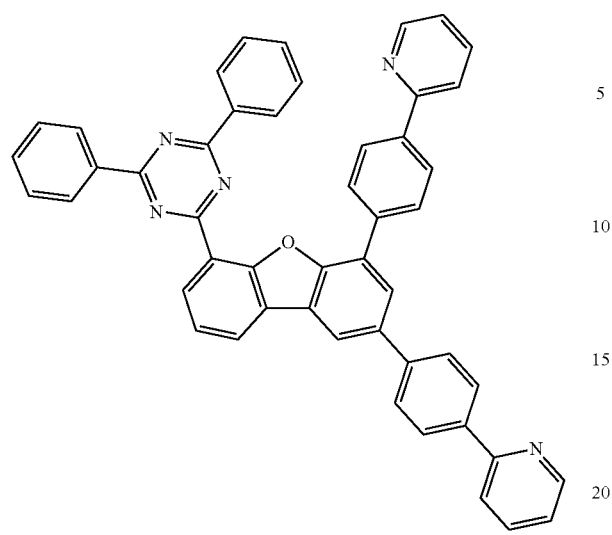
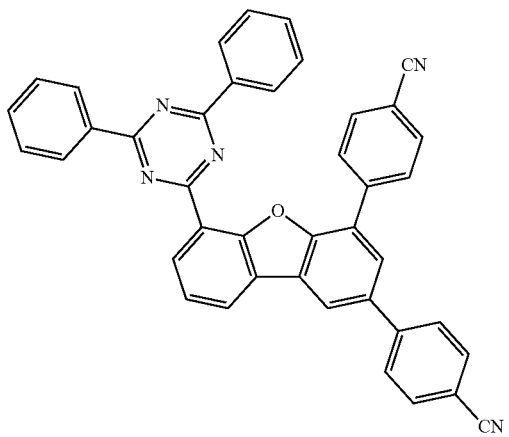
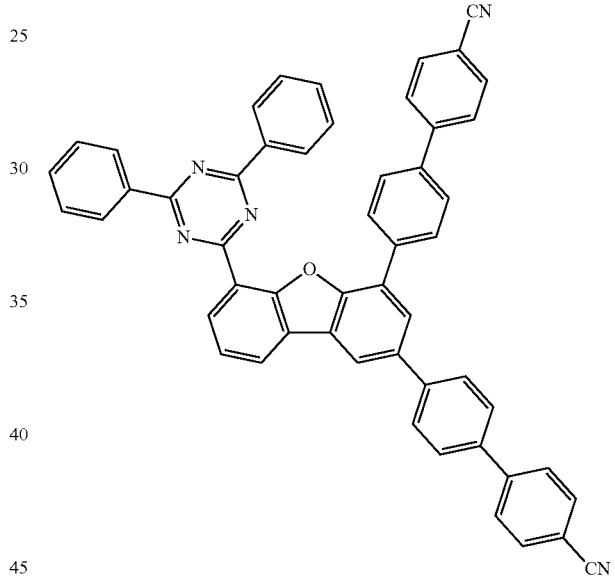
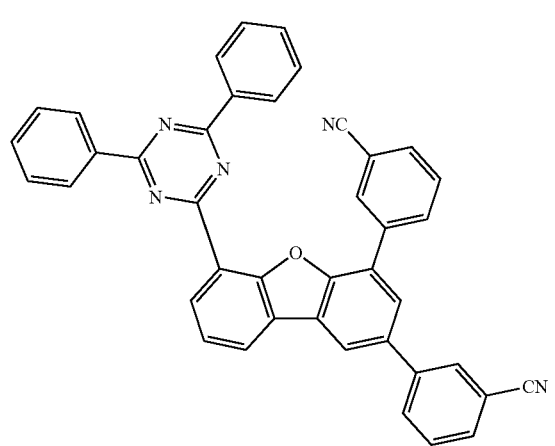
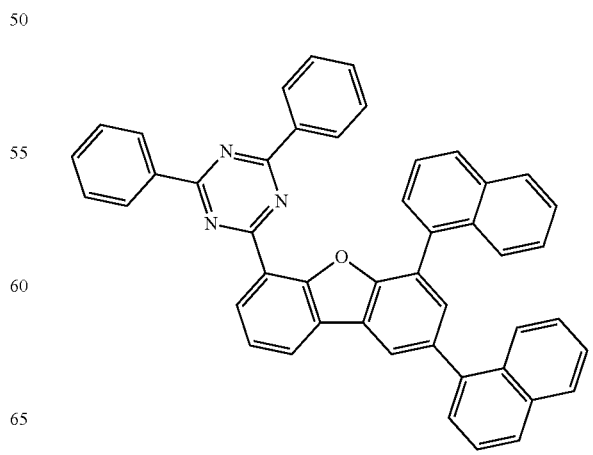

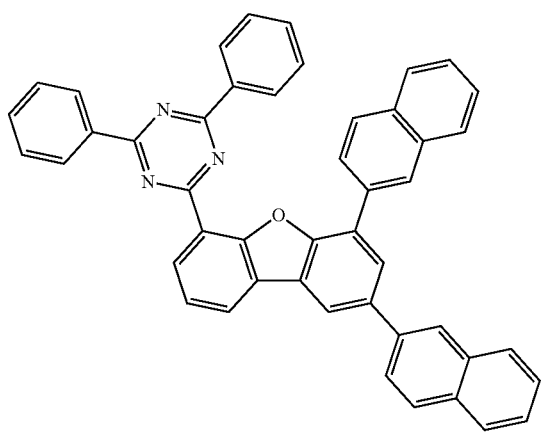
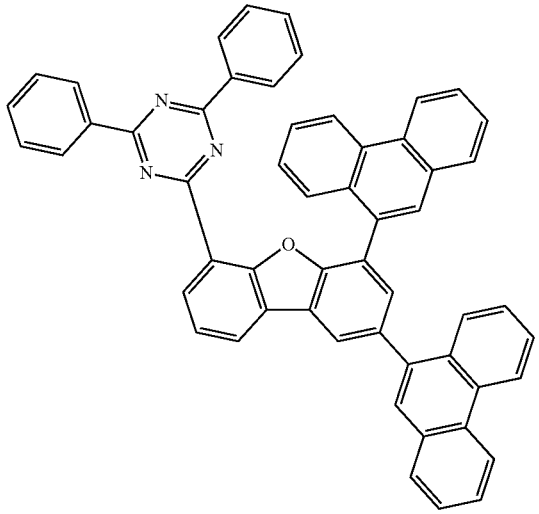
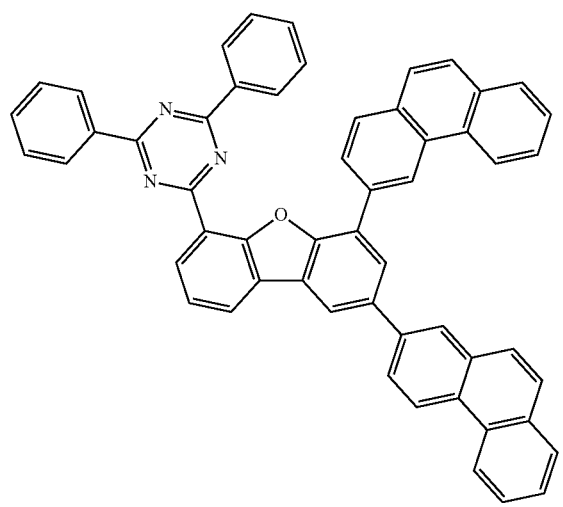
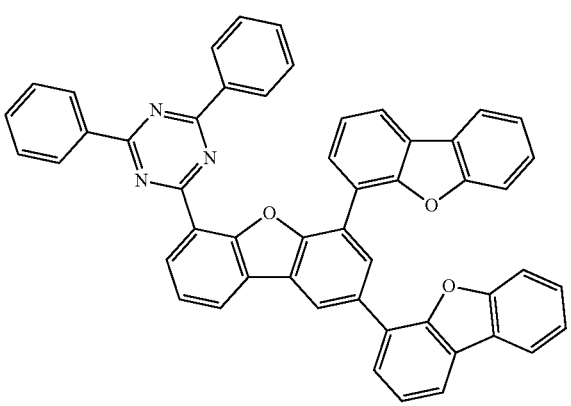
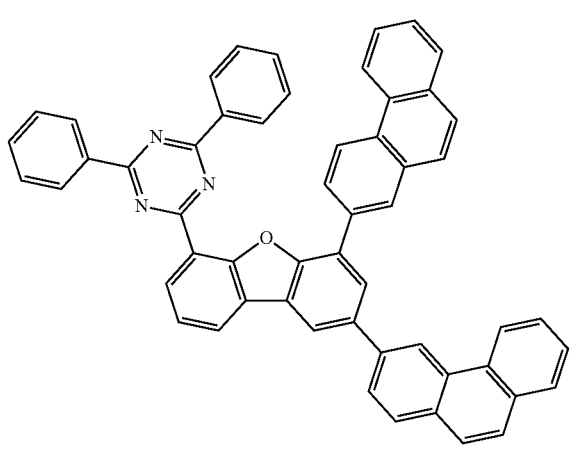
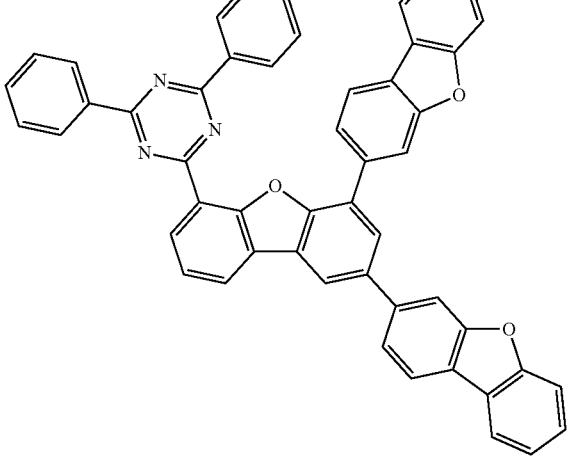

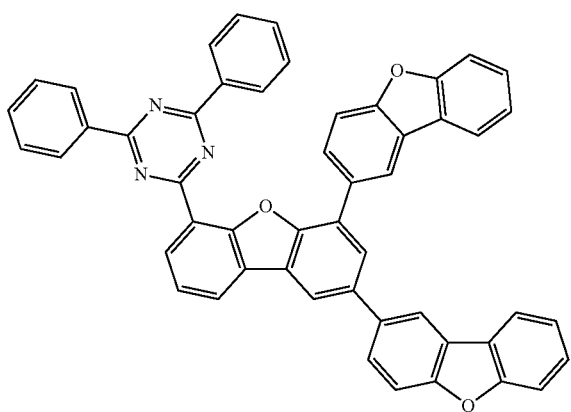
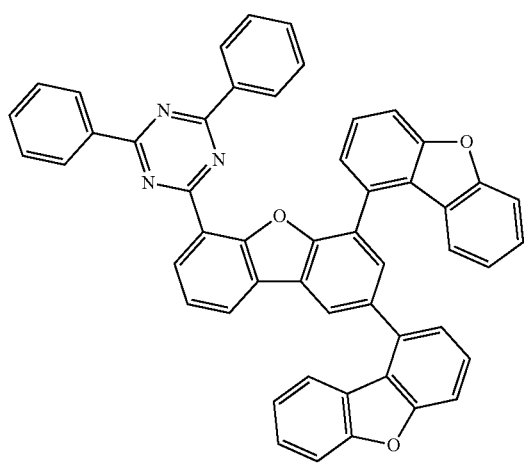
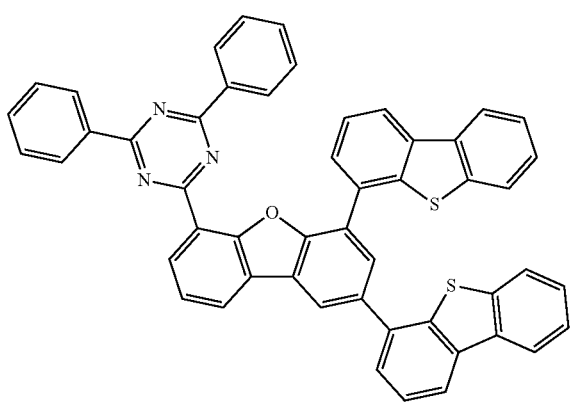
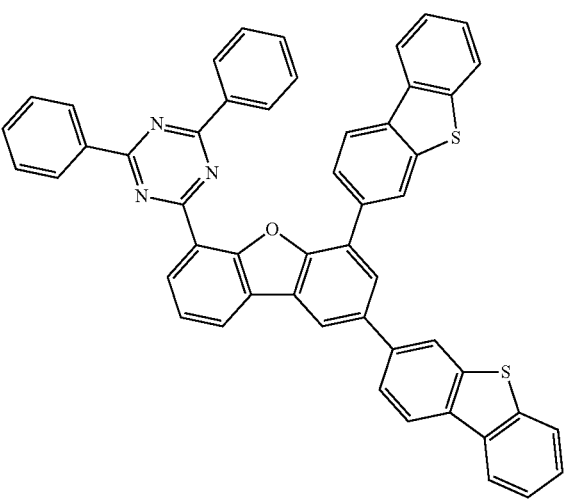

165
-continued
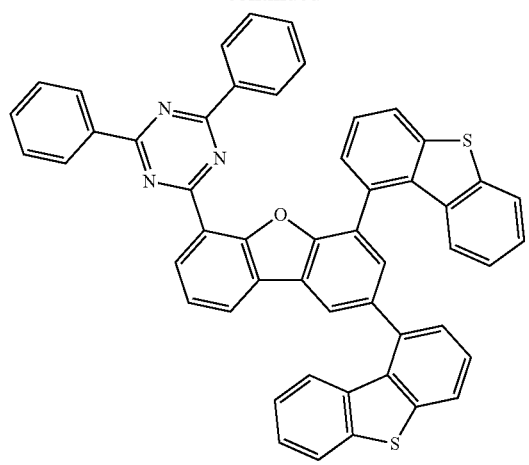
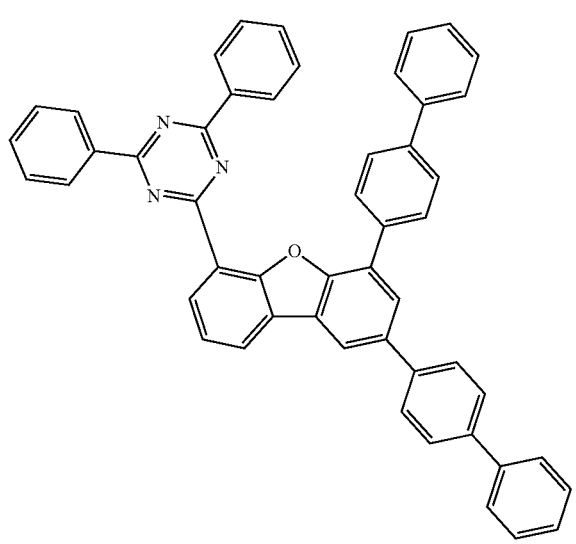
166
-continued
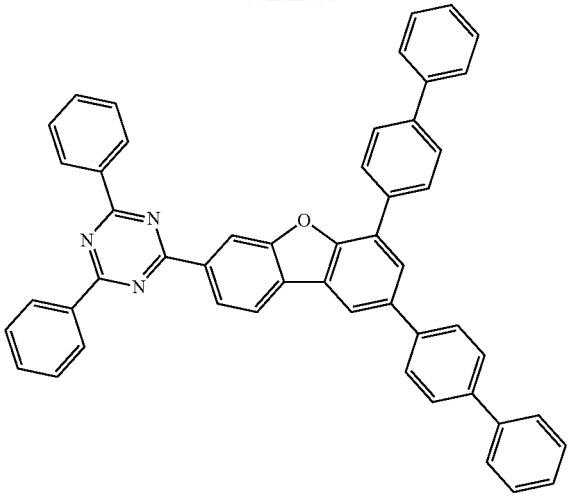
6. An organic light emitting device comprising a first electrode; a second electrode provided to face the first electrode; and one or more organic material layers provided between the first electrode and the second electrode, wherein one or more of the organic material layers comprises a compound according to claim 1.
* * * * *